(12) United States Patent
Vallier et al.

(10) Patent No.: US 12,203,099 B2
(45) Date of Patent: Jan. 21, 2025

(54) METHODS OF EXPANDING CHOLANGIOCYTES

(71) Applicant: Cambridge Enterprise Limited, Cambridge (GB)

(72) Inventors: Ludovic Vallier, Cambridge (GB); Nicholas Hannan, Cambridge (GB); Kourosh Saeb-Parsy, Cambridge (GB); Fotios Sampaziotis, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 795 days.

(21) Appl. No.: 16/623,701

(22) PCT Filed: Jun. 19, 2018

(86) PCT No.: PCT/EP2018/066295
§ 371 (c)(1),
(2) Date: Dec. 17, 2019

(87) PCT Pub. No.: WO2018/234323
PCT Pub. Date: Dec. 27, 2018

(65) Prior Publication Data
US 2021/0139856 A1 May 13, 2021

(30) Foreign Application Priority Data
Jun. 19, 2017 (GB) .................................. 1709704

(51) Int. Cl.
*C12N 5/071* (2010.01)
*A61K 35/413* (2015.01)
*A61P 1/16* (2006.01)

(52) U.S. Cl.
CPC .......... *C12N 5/0679* (2013.01); *A61K 35/413* (2013.01); *A61P 1/16* (2018.01); *C12N 2501/11* (2013.01); *C12N 2501/415* (2013.01); *C12N 2513/00* (2013.01); *G01N 2800/52* (2013.01)

(58) Field of Classification Search
CPC .............. C12N 5/0679; C12N 2501/11; C12N 2501/415; C12N 2513/00; A61P 1/16; A61K 35/413; G01N 2800/52
See application file for complete search history.

(56) References Cited

U.S. PATENT DOCUMENTS

| | | |
|---|---|---|
| 2014/0243227 A1 | 8/2014 | Clevers et al. |
| 2016/0376557 A1 | 12/2016 | Dubart et al. |
| 2020/0345867 A1 | 11/2020 | Selaru et al. |
| 2024/0122991 A1 | 4/2024 | Sampaziotis et al. |

FOREIGN PATENT DOCUMENTS

| | | | |
|---|---|---|---|
| TW | 201444972 | A | 12/2014 |
| WO | 2014/124527 | A1 | 8/2014 |
| WO | 2014/143632 | A1 | 9/2014 |
| WO | 2016/200340 | A1 | 12/2016 |
| WO | 2016/207621 | A1 | 12/2016 |
| WO | 2017/048193 | A1 | 3/2017 |
| WO | 2018/234323 | A1 | 12/2018 |
| WO | 2020/130615 | A1 | 6/2020 |
| WO | 2022/175342 | A1 | 8/2022 |
| WO | 2022/175373 | A1 | 8/2022 |

OTHER PUBLICATIONS

Lugli et al., R-spondin 1 and noggin facilitate expansion of resident stem cells from non-damaged gallbladders, EMBO reports, 17(5 ): 769-779. (Year: 2016).*
Shih et al., Pigment epithelium-derived factor (PEDF) peptide promotes the expansion of hepatic stem/progenitor cells via ERK and STAT3-dependent signaling, 9(3): 1114-1126. (Year: 2017).*
Gregory et al., The Wnt signaling inhibitor Dickkopf-1 is required for reentry into the cell cycle of human adult stem cells from bone marrow, 278(3): 28067-28078. (Year: 2003).*
Qin et al., Proliferation and migration mediated by Dkk-1/Wnt/beta-catenin cascade in a model of hepatocellular carcinoma cells, Translational Research, p. 281-294. (Year: 2007).*
Niehrs et al., The complex world of WNT receptor signalling, Nature Reviews, 13: 767-779 (Year: 2012).*
Hutch et al., EMBO Journal, Unlimited in vitro expansion of adult bi-potent pancreas progenitors through the Lgr5/R-spondin axis, 32: 2708-2721. (Year: 2013).*
Nikaido et al., A systemic survey of expression and function of zebrafish frizzled genes, PLoS ONE, 8(1): 1-15 (Year: 2013).*
Hutch et al., Long-term culture of genome-stable bipotent stem cells from adult human liver, Cell, 160: 299-312. (Year: 2015).*
Pettinato, Scalable differentiation of human iPSCs in a multicellular spheroid-based 3D culture into hepatocyte-like cells through direct Wnt/beta-catenin pathway inhibition, Nature Scientific Nature, 6: 1-17. (Year: 2016).*
Tocci et al., R-spondin-mediated WNT signaling potentiation in mammary and breast cancer development, IUBMB, p. 1546-1559 (Year: 2020).*
Song et al., New insights into the regulation of Axin function in canonical Wnt signaling pathway, Ptotein Cell, 5(3): 186-193. (Year: 2014).*
Chen et al., Development of small molecules targeting the Wnt pathway for the treatment of colon cancer: a high-throughput screening approach, Am J Physio Liver Physiol, 299: G292-G300. (Year: 2010).*

(Continued)

*Primary Examiner* — Arthur S Leonard
*Assistant Examiner* — Joseph Paul Miano
(74) *Attorney, Agent, or Firm* — HAMILTON, BROOK, SMITH & REYNOLDS, P.C.

(57) ABSTRACT

This invention relates to the expansion of primary cholangiocytes in the form of cholangiocyte organoids (COs) using culture conditions in which canonical Wnt signalling is inhibited and non-canonical Wnt/PCP signalling is potentiated. Methods of expanding primary cholangiocytes, expanded populations of cholangiocytes and medical applications of expanded cholangiocytes are provided.

9 Claims, 33 Drawing Sheets

(56) References Cited

OTHER PUBLICATIONS

Xiao et al., Importance of WNT-dependent signaling for derivation and maintenance of primed pluripotent bovine embryonic stem cells, Biology of Reproduction, 105(1): 52-63. (Year: 2021).*
Wang et al., Human Cholangiocytes Form a Polarized and Functional Bile Duct on Hollow Fiber Membranes, Frontiers in Bioengineering and Biotechnology, 19: 1-10. (Year: 2022).*
Merino-Azpitarte wt al., SOX17 regulates cholangiocyte differentiation and acts as a tumor suppressor in cholangiocarcinoma, Journal of Hepatology, 67: 72-83. (Year: 2017).*
Sigma-Aldrich, Mammalian Cell Culture, retrieved online Mar. 1, 2024. (Year: 2024).*
Bayramov, et al., "Novel Functions of Noggin Proteins: Inhibition of Activin/Nodal and Wnt Signaling," Development, vol. 138, No. 24, pp. 5345-5356 (Nov. 9, 2011).
Huch, et al., "In vitro expansion of single Lgr5+ liver stem cells induced by Wnt-driven regeneration," Nature, vol. 494, No. 7436, pp. 247-250 (Jan. 1, 2013).
Sampaziotis, et al., "Cholangiocytes derived from human induced pluripotent stem cells for disease modeling and drug validation," Nature Biotechnology, vol. 33, No. 8, whole document (Jul. 13, 2015).
Tanimizu, et al., "Hepatic biliary epithelial cells acquire epithelial integrity but lose plasticity to differentiate into hepatocytes in vitro during development," Journal of Cell Science, vol. 126, No. 22, pp. 5239-5246 (Sep. 17, 2013).
Notification of Transmittal of the International Search Report and The Written Opinion of the International Searching Authority, or the Declaration, and accompanying International Search Report and Written Opinion, for International Application No. PCT/EP2018/066295, entitled "Methods of Expanding Cholangiocytes," dated Oct. 26, 2018.
International Preliminary Report on Patentability for International Application No. PCT/EP2018/066295, entitled "Methods of Expanding Cholangiocytes," date Dec. 24, 2019.
Chen et al. "Small molecule-mediated disruption of Wnt-dependent signaling in tissue regeneration and cancer" Nat Chem Biol. Feb. 2009 ; 5(2): 100-107.
Bafico et al. "Novel mechanism of Wnt signalling inhibition mediated by Dickkopf-1 interaction with LRP6/Arrow" Nature Cell Biology vol. 3 Jul. 2001, 683-686.
Klaus et al. "Wnt signalling and its impact on development and cancer" Nat Rev Cancer. May 2008;8(5):387-98.
Moon et al. "Wnt and β-Catenin Signalling: Diseases and Therapies" Nat Rev Genet. Sep. 2004;5 (9):689-699.
Kazanskaya et al. "R-Spondin2 Is a Secreted Activator of Wnt/β-Catenin Signaling and Is Required for Xenopus Myogenesis" Developmental Cell, vol. 7, 525-534, Oct. 2004.
Lin et al. "The cysteine-rich frizzled domain of Frzb-1 is required and sufficient for modulation of Wnt signaling" Proc. Natl. Acad. Sci. USA vol. 94, pp. 11196-11200, Oct. 1997 Biochemistry.
Lu et al. "Structure/Activity Relationship Studies of Small-Molecule Inhibitors of Wnt Response" Bioorg Med Chem Lett. Jul. 15, 2009; 19(14): 3825-3827.
NIEHRS "The complex world of WNT receptor signalling" Nat Rev Mol Cell Biol. Dec. 2012; 13(12):767-79.
Sampaziotis et al. "Reconstruction of the mouse extrahepatic biliary tree using primary human extrahepatic cholangiocyte organoids" Nat Med. Aug. 2017;23(8):954-963 (Including Online Methods).
Sampaziotis et al. "Supplementary Data" (for "Reconstruction of the mouse extrahepatic biliary tree using primary human extrahepatic cholangiocyte organoids") Nat Med. Aug. 2017;23(8).
Kim et al. "Mitogenic Influence of Human R-Spondin1 on the Intestinal Epithelium" Science. Aug. 19, 2005;309 (5738):1256-59.
Semënov et al. "DKK1 Antagonizes Wnt Signaling without Promotion of LRP6 Internalization and Degradation" The Journal of Biological Chemistry vol. 283, No. 31, pp. 21427-21432, Aug. 1, 2008.
Tanimizu et al. "Liver Progenitor Cells Develop Cholangiocyte-Type Epithelial Polarity in Three-dimensional Culture" Molecular Biology of the Cell vol. 18, 1472-1479, Apr. 2007.
Tüysüz et al. "Lipid-mediated Wnt protein stabilization enables serum-free culture of human organ stem cells" Nat Commun 8, 14578 (2017).
European Examination Report dated Jun. 11, 2021 for European Application No. EP 18733834.8, entitled "Methods of Expanding Cholangiocytes".
Bertero, et al., Activin/Nodal signaling and NANOG orchestrate human embryonic stem cell fate decisions by controlling the H3K4me3 chromatin mark, Genes Dev. 29 (2015), 702-17.
Campos, et al., Chromosomal Spread Preparation of Human Embryonic Stem Cells for Karyotyping, JoVE. 31 (2009), 4-7.
Du, et al., lumi: a pipeline for processing Illumina microarray, Bioinformatics (2008), 1547-8, 24(13).
Enestvedt, et al., Biliary Complications Adversely Affect Patient and Graft Survival After Liver Retransplantation, Liver Transplantation (2013), 965-972, 19.
Farin, et al., Redundant Sources of Wnt Regulate Intestinal Stem Cells and Promote Formation of Paneth Cells, Gastroenterology (2012), 1518-1529, 143(6).
Felder, et al., Hepaticojejunostomy Using Short-Limb Roux-en-Y Reconstruction, JAMA Surg. (2013), 253-7, 148(3).
Gallo, et al., Current options for management of biliary atresia, Pediatr. Transplant. 17 (2013), 95-98.
Kanno, et al., Functional Heterogeneity of the Intrahepatic Biliary Epithelium, Hepatology 31 (2000), 555-61.
Koo, et al., Retroviral Gene Expression Control in Primary Organoid Cultures, Curr. Protoc. Stem Cell Biol. (2013), 5A.6.1-5A.6.8.
Koo, et al., Reviews in Basic and Clinical Gastroenterology and Hepatology, Gastroenterology (2014), 289-302, 147(2).
LeSage, et al., Regulation of cholangiocyte proliferation, Liver 21 (2001), 73-80.
Lin, et al., Model-based variance-stabilizing transformation for Illumina microarray data, Jan. 4, 2008, Nucleic Acids Research, 1-9, 36(2).
Murray, et al., AASLD Practice Guidelines: Evaluation of the Patient for Liver Transplantation, Hepatology 41 (2005), 1407-1432.
Perkins, J. D., Are we reporting the same thing?: Comments, Liver Transplant. 13 (2007), 463-467.
Sampaziotis, et al., Potential of human Induced Pluripotent Stem Cells in studies of liver disease, Hepatology 62 (2015).
Shultz, et al., Human Lymphoid and Myeloid Cell Development in NOD/LtSz-scid IL2Rnull Mice Engrafted with Mobilized Human Hemopoietic Stem Cells, The Journal of Immunology (2005), 6477-6489, 174(10).
Skaro, et al., The Impact of Ischemic Cholangiopathy following Donation after Cardiac Death Liver Transplantation—The Untold Story, Surgery. Oct. 2009, 543-553, 146(4).
Smyth, Linear Models and Empirical Bayes Methods for Assessing Differential Expression in Microarray Experiments, Statistical Applications in Genetics and Molecular Biology (2004), 1-26, 3(1).
Abenavoli, L. et al., "Primary Biliary Cholangitis and Bile Acid Farnesoid X Receptor Agonists," Diseases, vol. 8, No. 2, 12 pages (2020).
Brevini, T. et al., "Tissue engineering of the biliary tract and modelling of cholestatic disorders," Journal of Hepatology, 73: 918-932 (2020).
Chen, Chen et al, "Bioengineered bile ducts recapitulate key cholangiocyte functions", Biofabrication, vol. 69, Jun. 12, 2018, p. 7-54 (2018).
Dianat, Noushin et al, "Generation of functional cholangiocyte-like cells from human pluripotent stem cells and HepaRG cells", Hepatology, John Wiley & Sons, Inc, US, vol. 60, No. 2, Jun. 20, 2014, p. 700-714 (2014).
Great Britain Search Report Under Section 17 for GB Application No. GB2102232.2, Date of Search: Dec. 31, 2021.
International Search Report and Written Opinion received for PCT Patent Application No. PCT/EP2022/053842, mailed on Jul. 5, 2022, 13 pages.

(56) References Cited

OTHER PUBLICATIONS

International Search Report and Written Opinion received for PCT Patent Application No. PCT/EP2022/053910, mailed on Aug. 2, 2022, 10 pages.

Merino-Azpitarte et al., "SOX17 regulates cholangiocyte differentiation and acts as a tumor suppressor in cholangiocarcinoma" Journal of Hepatology, 67: 72-83. (Year: 2017).

Sampaziotis, Foti Os et al., "Cholangiocyte organoids can repair bile ducts after transplantation in the human liver", Science, vol. 371, No. 6531, Feb. 19, 2021, p. 839-846 (2021).

Sampaziotis, Foti Os et al, "Directed differentiation of human induced pluripotent stem cells into functional cholangiocyte-like cells", Nature Protocols, vol. 12, No. 4, Mar. 23, 2017, p. 814-827 (2017).

Smith, D.L.H. et al., "Sodium taurocholate inhibits intestinal adenoma formation in APCMin/+ mice, potentially through activation of the farnesoid X receptor," Carcinogenesis, vol. 31, No. 6: 1100-1109 (2010).

Tysoe, Olivia C. et al, "Isolation and propagation of primary human cholangiocyte organoids for the generation of bioengineered biliary tissue", Nature Protocols, vol. 14, No. 6, May 20, 2019, p. 1884-1925 (2019).

Hu, H., et al., "Long-Term Expansion of Functional Mouse and Human Hepatocytes as 3D Organoids", Cell, vol. 175, Nov. 29, 2018, pp. 1591-1606.

Inada, H., et al., "Direct reprogramming of human umbilical veinand peripheral blood-derived endothelial cells into hepatic progenitor cells", nature communications, vol. 11, Article No. 5292, 2020, 17 pages.

Lewis, P. L., et al., "Complex bile duct network formation within liver decellularized extracellular matrix hydrogels", Scientific Reports, vol. 8, Article No. 12220, 2018, 14 pages.

Semeraro, R., et al., "Multipotent stem/progenitor cells in the human foetal biliary tree", Journal of Hepatology, vol. 57, No. 5, Nov. 2012, pp. 987-994.

\* cited by examiner

METHODS OF EXPANDING CHOLANGIOCYTES

This application is the U.S. National Stage of International Application No. PCT/EP2018/066295, filed Jun. 19, 2018, which designates the U.S., published in English, and claims priority under 35 U.S.C. § 119 or 365 (c) to GB Application No. 1709704.9, filed Jun. 19, 2017. The entire teachings of the above applications are incorporated herein by reference.

FUNDING

The work leading to this invention has received funding from the European Research Council under the European Union's Seventh Framework Programme (FP7/2007-2013) ERC grant agreement number 281335 and from a MRC—Sparks Clinical Research Training Fellowship (MR/L016761/1).

FIELD

This invention relates to the isolation and propagation of primary adult or paediatric human cholangiocytes, for example for use in disease modelling, drug screening and regenerative medicine.

BACKGROUND

Disorders of the extrahepatic bile ducts carry considerable morbidity and mortality. Indeed, 70% of pediatric liver transplantations are performed to treat biliary atresia (Murray K. F. & Carithers R. L., Hepatology 2005, 41:1407-1432). Primary Sclerosing Cholangitis (PSC) alone accounts for 5% of US liver transplantations (Perkins J. D., Liver Transplant 2007, 13, 465-466) and biliary complications are the leading cause of graft failure following deceased liver transplantation (Skaro A. I. et al., Surgery 2009, 146:543-553; Enestvedt C. K. et al., Liver Transpl. 2013, 19:965-72). However, studies of the extrahepatic biliary epithelium have been limited by technical challenges in long-term culture and large-scale expansion of primary cholangiocytes. These challenges have so far precluded large scale experiments for drug screening and cells based therapy targeting PSC and other cholangiopathies. Furthermore, treatment options remain limited (Gallo A. & Esquivel C. O, Pediatr. Transplant. 2013, 17:95-98; Felder S. I. et al., JAMA Surg 2013, 148:253-7-8) due to the lack of healthy donor tissue that can be used to reconstruct and replace diseased bile ducts and/or gall bladders.

In vitro expansion of native cholangiocytes could address this challenge and provide cells suitable for tissue engineering applications such as biliary reconstruction. However, the culture of primary biliary epithelium remains problematic (Sampaziotis, F et al., Hepaology 2015, 62:303-311). The derivation of primary hepatic stem cells using an organoid culture system has been reported previously (Huch Metal.; Cell 2014 160:299-312). However, the capacity of the resulting cells to differentiate into functional cholangiocytes and populate the biliary tree in vivo remains to be demonstrated. Furthermore, in vivo applications of such platforms are restricted by contaminating stem cells with a capacity to proliferate inappropriately after transplantation and/or differentiate into non-biliary cell types. Limited access to human tissue constitutes a considerable obstacle for systems based on primary cells.

SUMMARY

The present inventors have recognised that culture conditions in which canonical Wnt signalling is inhibited and non-canonical Wnt/PCP signalling is potentiated unexpectedly allow the efficient expansion of primary cholangiocytes in the form of cholangiocyte organoids (COs). Populations of primary cholangiocytes expanded as described herein may be useful for example in regenerative medicine.

An aspect of the invention provides a method of expanding primary cholangiocytes in vitro comprising:
  (i) providing a population of isolated primary cholangiocytes and;
  (ii) culturing the population in an expansion medium comprising epidermal growth factor (EGF), a canonical Wnt signalling inhibitor and a non-canonical Wnt signalling potentiator, to produce an expanded population.

The cholangiocytes may form organoids in the expansion medium.

The non-canonical Wnt signalling potentiator may be a potentiator of canonical and non-canonical Wnt signalling, preferably R-spondin.

The canonical Wnt signalling inhibitor may be Dickkopf-related protein 1 (DKK-1).

Preferably, the primary cholangiocytes are cultured in three-dimensional culture in the expansion medium.

In some embodiments, the method may further comprise disrupting the organoids to produce a population of isolated cholangiocytes. The isolated cholangiocytes may be further cultured in the expansion medium to expand or propagate the population.

Another aspect of the invention provides a population of isolated cholangiocytes produced by a method described herein. The cholangiocytes may be in the form of organoids, sub-organoid assemblies or individual cells.

Preferably, the cholangiocytes are extrahepatic cholangiocytes.

Another aspect of the invention provides a scaffold comprising cholangiocytes produced by a method described herein.

Another aspect of the invention provides a method of treatment of a biliary disorder comprising administering a population of isolated cholangiocytes produced as described herein to an individual in need thereof.

Another aspect of the invention provides a method of screening a compound comprising;
  contacting a population of the cholangiocytes produced as described herein with a test compound, and;
  determining the effect of the test compound on the cholangiocytes and/or the effect of the cholangiocytes on the test compound.

Preferably, the cholangiocytes are contacted with the test compound are in the form of organoids (COs).

Another aspect of the invention provides a kit for production of cholangiocytes comprising an expansion medium comprising epidermal growth factor (EGF), a canonical Wnt signalling inhibitor and a non-canonical Wnt/PCP signalling potentiator.

Another aspect of the invention provides a method for in vitro modelling of a biliary disorder comprising;
  (i) providing a population of isolated primary cholangiocytes from an individual with a biliary disorder and;
  (ii) culturing the population in an expansion medium comprising epidermal growth factor (EGF), a canonical Wnt signalling inhibitor and a non-canonical Wnt signalling potentiator, to produce an expanded population of cholangiocytes displaying a biliary disorder genotype or phenotype.

Another aspect of the invention provides a method of testing an individual for a biliary disorder comprising;

providing a population of isolated primary cholangiocytes from the individual, expanding the population of cholangiocytes using a method of an aspect of the invention set out above; and determining the phenotype of the cholangiocytes.

Aspects and embodiments of the invention are described in more detail below.

DETAILED DESCRIPTION

Figure 1:
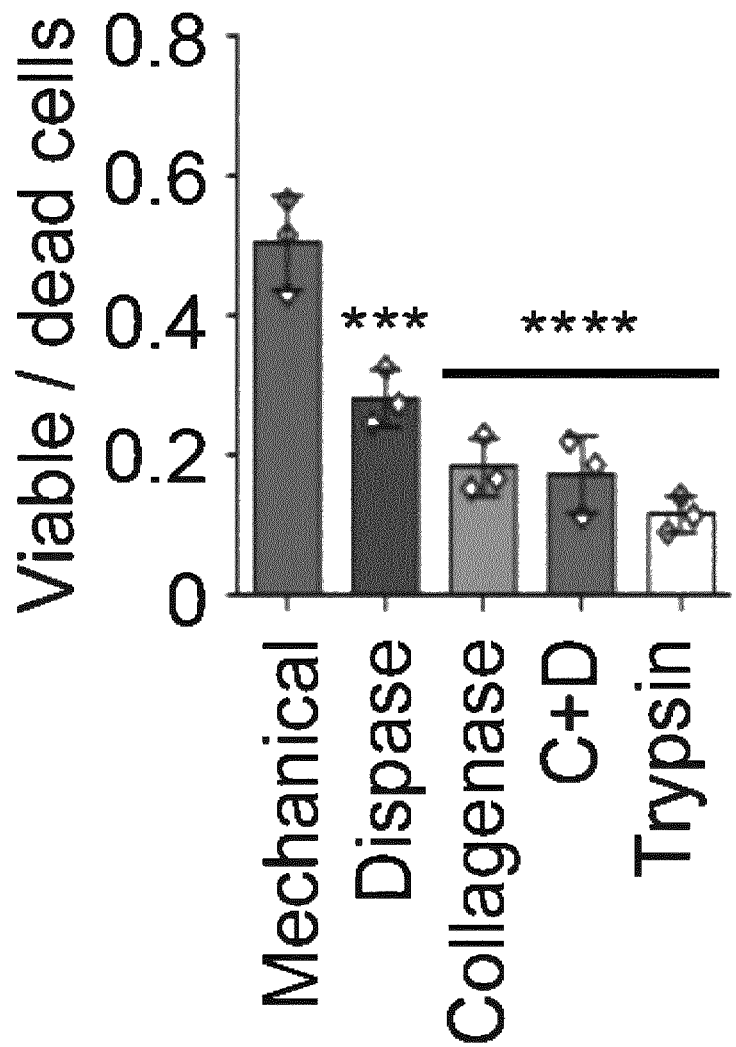
FIG. 1 shows the mean viability ratio following isolation of primary cholangiocytes with different methods. C+D: Collagenase+Dispase. Error bars show standard deviation; n=3. Asterisks represent statistically significant differences in viability ratio between mechanical dissociation and other isolation methods; *P<0.001, **P<0.0001 (one-way ANOVA with Dunnett correction for multiple comparisons)

This invention relates to the in vitro expansion of primary cholangiocytes using a cell culture medium (termed "expansion medium") comprising epidermal growth factor (EGF), a canonical Wnt signalling inhibitor and a non-canonical Wnt signalling potentiator. Cholangiocytes expanded as described herein may be useful for example in regenerative medicine and screening.

Cholangiocytes are cells from the epithelium of biliary tissue, which is a monolayer covering the luminal surface of the biliary tree. Cholangiocytes play important roles in bile secretion and electrolyte transport in vivo.

Primary cholangiocytes are isolated directly from the epithelium of intra- or extrahepatic biliary tissue, such as the bile duct or gall bladder and are distinct from continuous (artificially immortalized) biliary cell lines. Primary cholangiocytes may be intra- or extrahepatic cholangiocytes.

Primary cholangiocytes for use as described herein are mammalian, preferably human. Primary cholangiocytes may be obtained from adult or paediatric donors.

The population of primary cholangiocytes does not contain stem cells or other pluripotent or multipotent cells. The differentiation capacity of the primary cholangiocytes in the population is limited to their lineage of origin and they are not able to differentiate into cells of other lineages, such as hepatic or pancreatic cells (i.e. the population consists of cholangiocytes and cholangiocyte precursors).

In some embodiments, the primary cholangiocytes may be cancerous cells, which may be useful for example in drug screening.

Primary cholangiocytes may be obtained or isolated from primary bile tissue in the methods described herein or may have previously been obtained from primary bile tissue. Suitable bile tissue may include the gallbladder and bile ducts from any part of the hepatopancreatobiliary (HPB), pancreatobiliary (PB) or biliary system, including the common bile duct (CBD), cystic duct, common hepatic duct, right hepatic duct, left hepatic duct, intrahepatic ducts and pancreatic duct. Primary bile tissue may for example be obtained from liver explants, liver tissue, liver biopsy, bile duct excision, cholecystectomy or pancreatic resections.

In some preferred embodiments, the cholangiocytes are extrahepatic cholangiocytes. Extrahepatic cholangiocytes originate from the biliary epithelium of the extrahepatic biliary tree and may be obtained from extrahepatic bile tissue, such as the gall bladder, cystic bile duct, common bile duct or common hepatic duct.

In other embodiments, the cholangiocytes are intrahepatic cholangiocytes. Intrahepatic cholangiocytes originate from the biliary epithelium of the intrahepatic biliary tree.

The primary bile tissue from which the cholangiocytes are obtained may be in situ in a donor individual or may be a tissue sample previously obtained from a donor individual, for example after an operation or dissection, such as bile duct excision, liver resection or transplantation, pancreatic resection, cholangioscopy or cholecystectomy. Suitable tissue may be stored in preservation solution before use.

Populations of cholangiocytes may be obtained from primary bile tissue by any convenient technique. In some embodiments, peri-operative techniques may be employed, such as mechanical dissociation of the primary bile tissue for example by brushing or scraping, to dislodge a population of primary cholangiocytes. In other embodiments, minimally invasive techniques, such as Endoscopic Retrograde Cholangio-Pancreatography (ERCP) brushing, may be used.

In some embodiments, populations of cholangiocytes may be obtained by the mechanical dissociation of liver biopsies or explant tissues, for example by plating small (e.g. sub-millimetre) sections of tissue in the culture conditions described herein, with or without the addition of factors such as HGF and forskolin. Alternatively, liver tissue, gallbladder and bile duct explants may be dissociated to single primary cells or small clumps using a combination of mechanical dissociation (scrapping/dicing) and enzymatic digestion using a matrix digesting enzyme, such as liberase, collagenase, or hyalouronidase. Single primary cells may be subsequently be labelled with antibodies for biliary markers, such as EPCAM and isolated with immune isolation methods, such as Magnetic or Fluorescent associated Cell Sorting (MACS or FACS).

Figure 28:
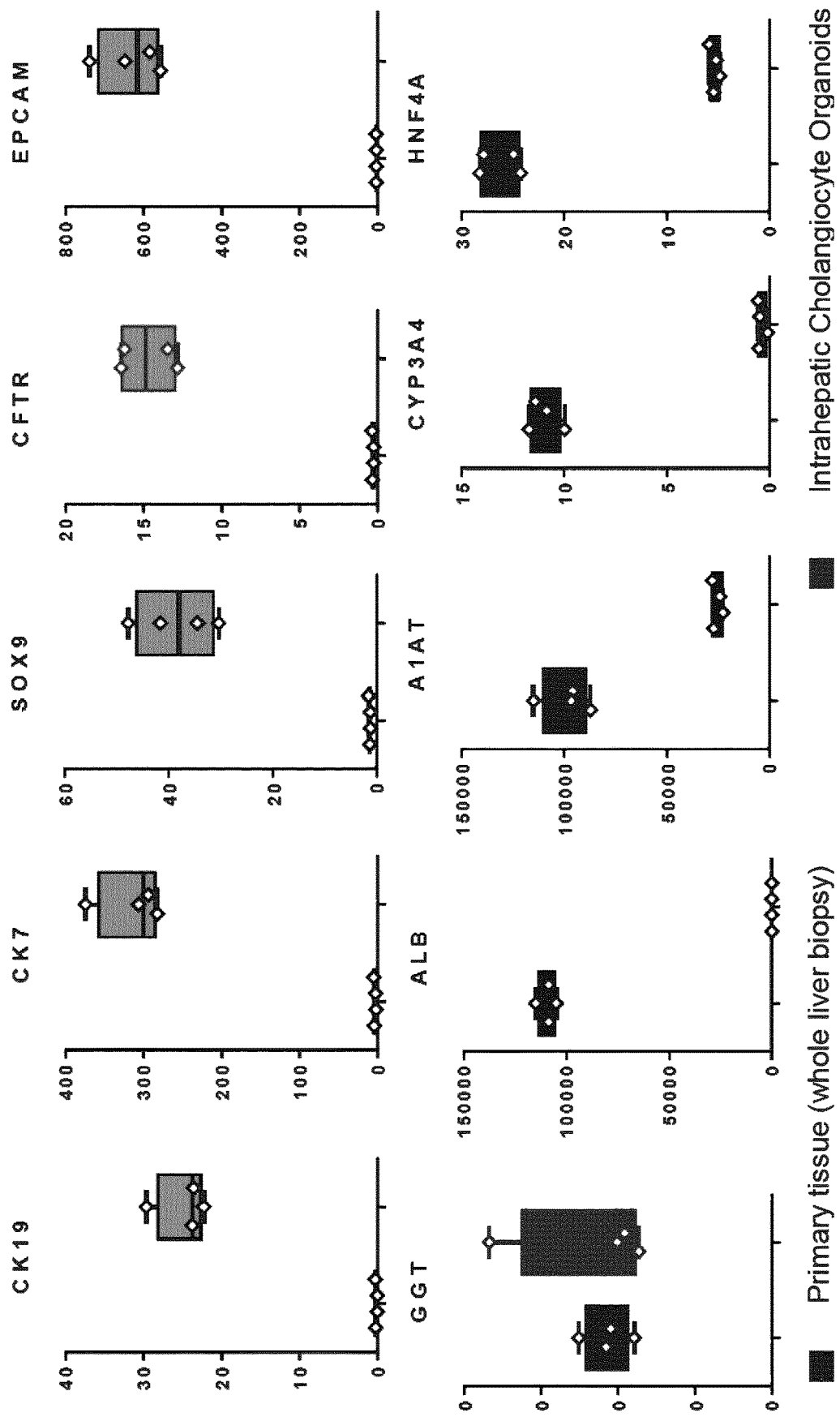
FIG. 28 shows QPCR analysis demonstrating the expression of key biliary markers in the absence of hepatic lineage markers by ICOs thereby confirming that this population is homogenous. The fold change over housekeeping gene expression is shown for markers CK19, CK7, SOX9, CFTR, EPCAM, GGT, ALB, A1AT, and HNF4A.

Isolated single cells may be plated using the 3D culture conditions described herein or processed for single cell RNA sequencing. The data herein shows that the 3D culture conditions described herein selectively expand cholangiocyte organoids. Other liver cell types, such as hepatocytes, are not propagated in these conditions. This may be shown for example, by the downregulation of hepatic markers (FIG. 28).

The primary bile tissue may be derived from heathy individuals or from patients with known pathology to enable disease modelling.

Cholangiocytes derived from an individual with a biliary disorder may be used to generate expanded populations which display a genotype or phenotype associated with a biliary disorder. A method of producing cholangiocytes with a biliary disorder-associated genotype or phenotype may comprise;

providing a population of primary cholangiocytes from an individual with a biliary disorder, expanding the primary cholangiocytes as described herein, thereby producing a population of cholangiocytes with a biliary disorder-associated genotype or phenotype.

An expanded population with a biliary disorder-associated phenotype may display one or more features of the biliary disorder. In some embodiments, the one or more features of the biliary disorder may be displayed in response specific conditions or treatments. For example, the cholangiocytes may be co-cultured with one or more other cell types to elicit a biliary disorder-associated phenotype. For example, the cholangiocytes may be co-cultured with immune cells, such as T-cells, to elicit a phenotype associated with an autoimmune biliary disorder, such as Primary Biliary Cirrhosis (PBC).

Once produced, cholangiocytes with the biliary disorder-associated phenotype may be cultured, expanded and maintained, for example for use in screening.

Cholangiocytes with a biliary disorder-associated phenotype may display one or more properties, features or pathologies characteristic of the biliary disorder.

The expansion medium is a cell culture medium that supports the proliferation of extrahepatic cholangiocytes in the form of organoids (cholangiocyte organoids).

The expansion medium is a nutrient medium which comprises EGF, a canonical Wnt inhibitor and a non-canonical Wnt potentiator.

A non-canonical Wnt signalling potentiator is a compound that stimulates, promotes or increases the activity of the non-canonical Wnt signalling pathway.

The non-canonical Wnt signalling pathway is a β-catenin-independent pathway involved in tissue polarity and morphogenetic processes in vertebrates (Komiya, Y. & Habas, R. *Organogenesis* 4,68-75 (2008); Patel, V. et al. *Hum. Mol. Genet.* 17,1578-1590 (2008); Strazzabosco, M. & Somlo, S. *Gastroenterology* 140, (2011).)

Components of the non-canonical Wnt signalling pathway include Wnt4, Wnt5a, Wnt11, LRPS/6, Dsh, Fz, Daam1, Rho, Rac, Prickle and Strabismus. Suitable methods for determining the activity of the non-canonical Wnt/PCP signalling pathway are well known in the art and include ATF-2-based reporter assays (Ohkawara et al (2011) Dev Dyn 240 (1) 188-194) and Rho-associated protein kinase (ROCK)-based assays.

A non-canonical Wnt signalling potentiator may selectively potentiate non-canonical Wnt signalling or more preferably, may potentiate both the non-canonical Wnt signalling and the canonical Wnt signalling pathway (i.e. a Wnt signalling agonist).

Preferred non-canonical Wnt signalling potentiators include the Wnt signalling agonist R-spondin.

R-spondin is a secreted activator protein with two cysteine-rich, furin-like domains and one thrombospondin type 1 domain that positively regulates Wnt signalling pathways. Preferably, R-spondin is human R-spondin.

R-spondin may include RSPO1 (GeneID 284654 nucleic acid sequence reference NM_001038633.3, amino acid sequence reference NP_001033722.1), RSPO2 (GeneID 340419 nucleic acid sequence reference NM_001282863.1, amino acid sequence reference NP_001269792.1), RSPO3 (GeneID 84870, nucleic acid sequence reference NM_032784.4, amino acid sequence reference NP_116173.2) or RSPO4 (GeneID 343637, nucleic acid sequence reference NM_001029871.3, amino acid sequence reference NP_001025042.2).

R-spondin is readily available from commercial sources (e.g. R&D Systems, Minneapolis, Minn.). Suitable concentrations of R-spondin for expanding cholangiocytes as described herein may be readily determined using standard techniques. For example, the expansion medium may comprise 50 ng/ml to 5 µg/ml R-spondin, preferably about 500 ng/ml.

A canonical Wnt signalling inhibitor is a compound that inhibits, blocks or reduces the activity of the canonical Wnt signalling pathway.

The canonical Wnt signalling pathway is a β-catenin-dependent pathway involved in the regulation of gene expression (Klaus et al Nat. Rev. Cancer (2008) 8 387-398; Moon et al (2004) Nat. Rev. Genet. 5 691-701; Niehrs et al Nat Rev Mol. Cell Biol. (2012) 13 763-779) Suitable methods for determining the activity of the canonical Wnt signalling pathway are well known in the art and include the TOP-flash assay (Molenaar et al Cell. 1996 Aug. 9; 86(3): 391-9) and assays for β-catenin.

Suitable canonical Wnt signalling inhibitors include Dickkopf-related proteins 1-4 (DKKs 1-4), Soggy-1/Dkkl1, secreted Frizzled related proteins 1-5 (sFRP1-5), Wnt inhibitory factor-1 (WIF-1), draxin, SOST/sclerostin, IGFBP-4, USAG1 and Notum.

Preferably, the canonical Wnt signalling inhibitor is DKK-1. DKK-1 (GeneID 22943 nucleic acid sequence reference NM_012242.2, amino acid sequence reference NP_036374.1) is a secreted protein with two cysteine rich regions that plays a role in embryogenesis. DKK-1 is readily available from commercial sources (e.g. R&D Systems, Minneapolis, Minn.). Suitable concentrations of DKK-1 for expanding cholangiocyte organoids as described herein may be readily determined using standard techniques. For example, the expansion medium may comprise 10 ng/ml to 1 µg/ml DKK-1, for example about 100 ng/ml.

Epidermal Growth Factor (EGF; NCBI GeneID: 1950, nucleic acid sequence NM_001178130.1 GI: 296011012; amino acid sequence NP_001171601.1 GI: 296011013) is a protein factor which stimulates cellular growth, proliferation and cellular differentiation by binding to an epidermal growth factor receptor (EGFR). EGF may be produced using routine recombinant techniques or obtained from commercial suppliers (e.g. R&D Systems, Minneapolis, Minn.; Stemgent Inc, USA). Suitable concentrations of EGF for expanding cholangiocyte organoids as described herein may be readily determined using standard techniques. For example, the expansion medium may comprise 2 to 500 ng/ml EGF, preferably about 20 ng/ml.

Preferably, the primary cholangiocytes are cultured in the expansion medium in three-dimensional culture. For three-dimensional culture, the expansion medium further comprises a scaffold matrix which supports the growth and proliferation of cells in 3-dimensions and allows the cholangiocytes to assemble into organoids.

Suitable scaffold matrices are well-known in the art and include hydrogels, such as collagen, collagen/laminin, compressed collagen (e.g. RAFT™, TAP Biosystems), alginate, agarose, complex protein hydrogels, such as Base Membrane Extracts, and synthetic polymer hydrogels (Gjorevski et al Nature (2016) 539 560-564), such as polyglycolic acid (PGA) hydrogels and crosslinked dextran and PVA hydrogels (e.g. Cellendes Gmbh, Reutlingen DE), inert matrices, such as porous polystyrene, and isolated natural ECM scaffolds (Engitix Ltd, London UK).

The scaffold matrix may be chemically defined, for example a collagen or densified collagen hydrogel, or non-chemically defined, for example a complex protein hydrogel. Preferably, the scaffold matrix in the expansion medium is a complex protein hydrogel. Suitable complex protein hydrogels may comprise extracellular matrix components, such as laminin, collagen IV, enactin and heparin sulphate proteoglycans. Complex protein hydrogels may also include hydrogels of extracellular matrix proteins from Engelbreth-Holm-Swarm (EHS) mouse sarcoma cells. Suitable complex protein hydrogels are available from commercial sources and include Matrigel™ (Corning Life Sciences) or Cultrex™ BME 2 RGF (Amsbio™ Inc). For example, the expansion medium may comprise 66% Matrigel™.

The expansion medium may comprise or consist of a scaffold matrix and a nutrient medium supplemented with (i) EGF, (ii) a canonical Wnt inhibitor, such as DKK-1 and (iii) a non-canonical Wnt potentiator, such as R-spondin.

A nutrient medium may comprise a basal medium. Suitable basal media include Iscove's Modified Dulbecco's Medium (IMDM), Ham's F12, Advanced Dulbecco's modified eagle medium (DMEM) or DMEM/F12 (Price et al Focus (2003), 25 3-6), Williams E (Williams, G.M. et al Exp. Cell Research, 89, 139-142 (1974)), and RPMI-1640 (Moore, G. E. and Woods L. K., (1976) Tissue Culture Association Manual. 3, 503-508. In some embodiments, Williams E medium may be preferred for example 33% Williams E medium.

The basal medium may be supplemented with a media supplement and/or one or more additional components, for example transferrin, 1-thioglycerol, lipids, L-glutamine or substitutes, such as L-alanyl-L-glutamine (e.g. Gluta-max™), nicotinamide, linoleic acid and selenous acid (e.g. ITS+ premix), dexamethasone, selenium, pyruvate, buffers, such as HEPES, sodium bicarbonate, phospho-L-ascorbic acid trisodium salt, glucose and antibiotics such as penicillin and streptomycin and optionally polyvinyl alcohol; polyvinyl alcohol and insulin; serum albumin; or serum albumin and insulin.

For example, the basal medium may be supplemented with 10 mM nicotinamide, 17 mM sodium bicarbonate, 0.2 mM 2-phospho-L-ascorbic acid trisodium salt, 6.3 mM sodium pyruvate, 14 mM glucose, 20 mM HEPES, 6 µg/ml insulin, human 6 µg/ml transferrin, 6 ng/ml selenous acid, 5 µg/ml linoleic acid, 0.1 uM dexamethasone, 2 mM L-alanyl-L-glutamine, 100 U/ml penicillin, 100 µg/ml streptomycin.

The nutrient medium may be a chemically defined basal nutrient medium. A chemically defined medium is a nutritive solution for culturing cells which contains only specified components, preferably components of known chemical structure. A chemically defined medium is devoid of undefined components or constituents which include undefined components, such as feeder cells, stromal cells, serum, serum albumin and complex extracellular matrices, such as Matrigel™. A chemically defined medium may be humanised. A humanised chemically defined medium is devoid of components or supplements derived or isolated from non-human animals, such as Foetal Bovine Serum (FBS) and Bovine Serum Albumin (BSA), and mouse feeder cells. Conditioned medium includes undefined components from cultured cells and is not chemically defined.

Suitable chemically defined nutrient media are well-known in the art and include William's E medium supplemented with nicotinamide, sodium bicarbonate, 2-phospho-L-ascorbic acid trisodium salt, sodium pyruvate, glucose, HEPES, ITS+ premix (insulin, transferrin, selenous acid, and linoleic acid), dexamethasone, glutamax, penicillin and streptomycin.

The cholangiocytes may be cultured in the expansion medium for multiple passages. For example, the cholangiocytes may be cultured for 10 or more, 20 or more, 30 or more, 40 or more or 50 or more passages. A passage may take 2-8 days, preferably about 5 days.

The cholangiocytes may be passaged by digesting the scaffold matrix, harvesting cholangiocyte organoids by centrifugation and disrupting the organoids into individual cholangiocytes. The cholangiocytes may be re-suspended and cultured as described above in the expansion medium where they reform into organoids.

Suitable techniques for cell culture are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430) Basic Cell Culture Protocols' by J. Pollard and J. M. Walker (1997), 'Mammalian Cell Culture: Essential Techniques' by A. Doyle and J. B. Griffiths (1997), 'Human Embryonic Stem Cells' by A. Chiu and M. Rao (2003), Stem Cells: From Bench to Bedside' by A. Bongso (2005), Peterson & Loring (2012) Human Stem Cell Manual: A Laboratory Guide Academic Press and 'Human Embryonic Stem Cell Protocols' by K. Turksen (2006). Media and ingredients thereof may be obtained from commercial sources (e.g. Gibco, Roche, Sigma, Europa bioproducts, R&D Systems). Standard mammalian cell culture conditions may be employed for the above culture steps, for example 37° C., 21% Oxygen, 5% Carbon Dioxide. Media is preferably changed every two days and cells allowed to settle by gravity The population of cholangiocytes may be expanded $10^5$ fold or more, $10^{10}$ fold or more, $10^{15}$ fold or more, $10^{20}$ fold or $10^{30}$ fold or more as organoids in the expansion medium as described herein.

The population of primary cholangiocytes proliferates in the expansion medium and assembles into organoids (COs). Cholangiocyte organoids are three-dimensional multicellular assemblies or cysts that comprise a layer of cholangiocytes linked by tight junctions which surrounds an interior lumen and separates it from the external environment. The cholangiocytes may display polarised expression of markers, such as CFTR.

The organoids formed by the cholangiocytes in the expansion medium may display the morphology or physical characteristics of cholangiocytes, for example extrahepatic cholangiocytes, such as CBD cholangiocytes. Organoids may for example comprise cilia. Tight junctions, microvilli, exosomes and/or tubular structures. The morphology and physical characteristics of organoids may be determined by standard microscopic procedures.

The expanded population of cholangiocytes, whether in the form of organoids or individual cells, may be free or substantially free from other cell types i.e. the population of cholangiocytes may be homogeneous or substantially homogeneous. For example, the population may contain, 80% or more, 90% or more, 95% or more, 98% or more or 99% or more cholangiocytes, following culture in the medium. Preferably, the population of cholangiocytes is sufficiently free of other cell types that no purification is required.

The cholangiocytes may express one or more biliary markers. For example, the cholangiocytes may express Cytokeratin 7 (KRT7 or CK7), Cytokeratin 19 (KRT19 or CK19), Gamma Glutamyl-Transferase (GGT), Hepatocyte Nuclear Factor 1 beta (HNF1B), Secretin Receptor (SCTR), Sodium-dependent Bile Acid Transporter 1 (ASBT/SLC10A2), SRY-box 9 (SOX9) Jagged 1 (JAG1), NOTCH2, SCR, SSTR2, Apical Salt and Bile Transporter (ASBT), Aquaporin 1 and Anion Exchanger and Cystic Fibrosis Transmembrane Conductance Regulator (CFTR). Typically, at least 98% of the cholangiocytes in the population may co-express CK7 and CK19 following 20 passages in the expansion medium as described herein.

Preferably, the cholangiocytes express mature biliary markers at levels corresponding to primary common bile duct (CBD) cholangiocytes. The cholangiocytes may be mature cholangiocytes and may lack foetal characteristics.

In contrast to primary cholangiocytes, the cholangiocytes in the expanded population may lack expression of MHC class 1 or class 2 proteins, for example HLA proteins such as HLA-E or HLA-DRB1. In addition, the cholangiocytes may lack expression of genes that are characteristic of the regional identity of primary cholangiocytes, for example genes induced by inflammation or bile acid gradient. Since they are proliferative and display low or absent immune profile markers, cholangiocytes produced as described herein are distinct from primary cholangiocytes, which do not proliferate and have high immune profile markers.

The population of cholangiocytes is devoid of stem cells or other pluripotent or multipotent cells. The cholangiocytes display no expression or low expression of stem cell markers, such as POU5F1, OCT4, NANOG, prominin 1 (PROM1), a leucine 4 rich repeat containing G protein-coupled receptor (LGR), such as LGR-4, 5, or 6, Sox2, SSEA-3, SSEA-4, Tra-1-60, KLF-4 and c-myc, relative to control cells. In some preferred embodiments, the cholangiocytes express high levels of biliary markers, low levels of stem cell markers, such as LGR5 and PROM1 and no expression of pluripotency markers, such as Oct4, NANOG and Sox2.

The population of cholangiocytes is devoid of non-cholangiocyte cells, such as hepatic or pancreatic cells. The cholangiocytes do not express markers of non-biliary lineages, such as hepatocyte or pancreatic markers. For example, the cholangiocytes may lack expression of albumin (ALB), a1-antitrypsin (SERPINA1 or 6 A1AT), pancreatic and duodenal homeobox 1 (PDX1), insulin (INS), glucagon (GCG) and hepatoblast fetal markers, such as AFP.

The population of cholangiocytes do not express epithelial-mesenchymal transition (EMT) markers. For example, the cholangiocytes may lack expression of vimentin (VIM), snail family transcriptional repressor 1 (SNAI1) and/or S100 calcium binding protein 9 A4 (S100A4).

The expression of one or more biliary markers and the absence of expression of one or more non-biliary markers may be monitored and/or detected in the expanded population of cholangiocytes. For example, the expression or production of one or more of the mature biliary markers set out above in the expanded population of cholangiocytes may be determined. This allows the homogeneity of the expanded population of cholangiocytes to be determined and/or monitored.

The expanded population of cholangiocytes produced as described herein may display in vitro one or more functional properties of primary cholangiocytes, for example, extrahepatic cholangiocytes, such as primary common bile duct (CBD) cholangiocytes. For example, the cholangiocytes may assemble into organoids that display one or more, preferably all of the properties described below.

The cholangiocyte organoids may display bile acid transfer, alkaline phosphatase (ALP) activity and/or Gamma-Glutamyl-Transpeptidase (GGT) activity. The amount of ALP and GGT activity may correspond to the amount of ALP and GGT activity displayed by primary common bile duct (CBD) cholangiocytes. ALP and GGT activity may be determined, for example, as described herein.

The cholangiocyte organoids may display active secretion, for example, secretion mediated by multidrug resistance protein-1 (MDR1). This may be determined by measuring the accumulation of a fluorescent MDR1 substrate, such as Rhodamine123, in the lumen of cholangiocyte organoids in the presence and absence of MDR1 inhibitor verapamil, as described herein.

The cholangiocyte organoids may display responses to secretin and somatostatin. For example, the cholangiocyte organoids may display increased secretory activity in response to secretin and decreased activity in response to somatostatin. This may be determined by measuring changes in organoid size. For example, secretin may increase and somatostatin may decrease the size of cholangiocyte organoids.

The cholangiocyte organoids may display active transfer of bile acids, for example transfer mediated by Apical Salt and Bile Transporter (ASBT). Bile acid transfer activity may be determined, for example, by measuring the active transfer of a fluorescent bile salt, such as CLF, relative to another fluorescent compound, such as FITC, as described herein.

The cholangiocyte organoids may display Cystic Fibrosis Transmembrane Conductance Regulator (CFTR) activity. CTFR activity may be determined by measuring intracellular and intraluminal chloride concentrations in response to media with varying chloride concentrations, for example, the fluorescent chloride indicator N-(6-methoxyquinolyl) acetoethyl ester (MQAE), as described herein.

The cholangiocyte organoids may display responses to ATP and acetylcholine. For example, intracellular $Ca^{2+}$ levels may increase in the cholangiocyte organoids in response to ATP or acetylcholine. Intracellular $Ca^{2+}$ levels may be determined using standard techniques.

The cholangiocyte organoids may display responses to Vascular Endothelial Growth Factor (VEGF), Mitogens such as IL6, and oestrogens. For example, the cholangiocyte organoids may display increased proliferation in response to VEGF.

The cholangiocyte organoids may display responses to drugs, such as lumacaftor (VX809). For example, size, CFTR activity and/or intraluminal fluid secretion may increase in response to lumacaftor in cholangiocyte organoids expanded from primary cholangiocytes obtained from a donor individual with cystic fibrosis. Suitable methods for determining responses to lumacaftor are described below.

The amount of response and/or activity of the cholangiocyte organoids produced by the claimed methods may correspond to the amount of response and/or activity displayed by primary cholangiocytes, preferably primary intrahepatic cholangiocytes or primary extrahepatic cholangiocytes, such as common bile duct (CBD) cholangiocytes.

Following the expansion in expansion medium, as described above, cholangiocyte organoids may be dissociated or disrupted to generate individual cholangiocytes.

Suitable methods of dissociating organoids into individual constituent cells are well-known in the art. For example, the cholangiocyte organoids may be harvested from the expansion medium using a dispase or non-enzymatic recovery solution, such as Cell Recovery Solution™ (Corning) and dissociated using a protease, such as trypsin. Suitable reagents are commercially available and include TrypLE™ Express (ThermoFisher Scientific).

The ability of cholangiocytes expanded as described herein to perform one or more cholangiocyte functions may be monitored and/or determined. For example, the ability of the cells to assemble into organoids, and/or perform one or more of MDR1 function; bile acid transfer; VEGF, acetylcholine or ATP responses; CFTR mediated chloride transport; or secretin or somatostatin responses may be monitored and/or determined.

Cholangiocytes produced as described herein may be expanded as described herein or cultured or maintained using standard mammalian cell culture techniques or subjected to further manipulation or processing. In some embodiments, the cholangiocyte populations produced as described herein may be stored, for example by lyophilisation and/or cryopreservation. The cholangiocytes may be stored as organoids, sub-organoid assemblies or individual cells. Suitable storage methods are well known in the art. For example, the cholangiocytes may be suspended in a cryopreservation medium (for example, Cellbanker™ (AMS Biotechnology Ltd, UK) and frozen, for example at −70° C. or below.

The population of cholangiocytes may be admixed with other reagents, such as buffers, carriers, diluents, preservatives, and/or pharmaceutically acceptable excipients. Suitable reagents are described in more detail below. A method described herein may comprise admixing the population of cholangiocytes with a therapeutically acceptable excipient to produce a therapeutic composition. The admixed cholangiocytes may be in the form of organoids, sub-organoid assemblies or individual cells.

In some embodiments, the cholangiocytes may be useful in therapy. For therapeutic applications, the cholangiocytes are preferably clinical grade cells. Populations of cholangiocytes for use in treatment are preferably produced from primary cholangiocytes as described herein using a chemically defined expansion medium. The cholangiocytes may be in the form of organoids, sub-organoid assemblies or individual cells, depending on the specific application.

The expanded population of cholangiocytes may be transplanted, infused or otherwise administered into the individual. Suitable techniques are well known in the art.

The expanded population of cholangiocytes may be autologous i.e. the cholangiocytes were expanded from primary cholangiocytes originally obtained from the same individual to whom they are subsequently administered (i.e. the donor and recipient individual are the same). A suitable expanded population of cholangiocytes for administration to a recipient individual may be produced by a method comprising providing an initial population of primary cholangiocytes obtained from the individual and expanding the population of cholangiocytes as described above to produce an expanded population of cholangiocytes for administration.

The expanded population of cholangiocytes may be allogeneic i.e. the primary cholangiocytes were originally obtained from a different individual to the individual to whom the cholangiocytes are subsequently administered (i.e. the donor and recipient individual are different). The donor and recipient individuals may be HLA matched to avoid rejection and other undesirable immune effects. A suitable expanded population of cholangiocytes for administration to a recipient individual may be produced by a method comprising providing an initial population of primary cholangiocytes obtained from a donor individual, and expanding the population of cholangiocytes as described above to produce an expanded population of cholangiocytes for administration. In some embodiments, the expanded population may be engineered to reduce or inactivate the expression of immunogenic antigens, such as HLAs.

In some preferred embodiments, the expanded population of cholangiocytes may be admixed with a biocompatible scaffold.

A biocompatible scaffold may be seeded with cholangiocytes expanded as described above. For example, individual cholangiocytes or sub-organoid assemblies of cholangiocytes may be injected on or into a scaffold or mixing into the scaffold during the manufacturing process. The scaffold containing the cholangiocytes may then be cultured in expansion medium, such that the cholangiocytes populate the scaffold. The cholangiocytes may proliferate within the scaffold and assemble into organoids and then into a multilayered epithelium.

Suitable biocompatible scaffolds may include hydrogels, such as fibrin, chitosan, glycosaminoglycans, silk, fibrin, fibronectin, elastin, collagen, glycoproteins such as fibronectin, or polysaccharides such as chitin, or cellulose collagen, collagen/laminin, densified collagen, alginate, agarose, complex protein hydrogels, such as Base Membrane Extracts, bio-organic gels, and synthetic polymer hydrogels, such as polylactic acid (PLA) polyglycolic acid (PGA), polycapryolactone (PCL) hydrogels, crosslinked dextran and PVA hydrogels (e.g. Cellendes Gmbh, Reutlingen DE), inert matrices, such as porous polystyrene, polyester, soluble glass fibres porous polystyrene, and isolated natural ECM scaffolds, for example decellularized gall bladder and bile duct scaffolds (Engitix Ltd, London UK). The scaffold may be biodegradable.

The size or shape of the scaffold is dependent on the intended application. Suitable scaffold shapes may for example include patches, sheets and tubes, including straight and branched tubes, with diameters up to for example 10-12 mm.

Cholangiocytes produced as described herein that are cultured within a biocompatible scaffold organize into a functional biliary epithelium. The populated scaffold may display one or more properties of the biliary epithelium. For example, the populated scaffold may be bile resistant and may display one or more of the functional properties described above. A scaffold populated with cholangiocytes may be useful as artificial biliary epithelial tissue, for example for use in therapy or screening.

Another aspect of the invention provides a population of isolated cholangiocytes produced by a method described herein. The population may be in the form of organoids, sub-organoid assemblies or clusters or individual cells.

A population of cholangiocytes generated as described herein may be substantially free from other cell types. For example, the population may contain 70% or more, 80% or more, 85% or more, 90% or more, or 95% or more cholangiocytes, following culture in the expansion medium. The presence or proportion of cholangiocytes in the population may be determined through the expression of biliary markers as described above.

Preferably, the population of cholangiocytes is sufficiently free of other cell types that no purification is required. If required, the population of cholangiocytes or cholangiocyte organoids may be purified by any convenient technique, including FACS.

In some embodiments, the cholangiocytes may be engineered to express a heterologous protein, for example a marker protein, such as GFP, or an enzyme and/or to reduce or prevent expression of one or more endogenous protein, for example proteins associated with immunogenicity. For example, the cholangiocytes may be transfected with a vector comprising a nucleic acid encoding a heterologous protein; a suppressor RNA which suppresses the expression of an endogenous protein; or a site specific nuclease that inactivates an endogenous protein. In some embodiments, the cholangiocytes may be engineered to correct a genetic defect. For example, defects in the CFTR gene may be corrected in cholangiocytes derived from an individual with cystic fibrosis. In other embodiments, the cholangiocytes may be engineered to remove immunogenic antigens, such as human leukocyte antigens (HLA). This may be useful in generating low or non-immunogenic cells for allogenic use.

Another aspect of the invention provides a scaffold comprising cholangiocytes by a method described herein. Suitable scaffolds are described above.

Another aspect of the invention provides an artificial biliary epithelium tissue comprising a scaffold populated with cholangiocytes produced by a method described herein, for example for use in therapy. In addition to cholangiocytes, an artificial tissue may incorporate other cells, such as stromal and/or endothelial cells.

Aspects of the invention also extend to a pharmaceutical composition, medicament, drug or other composition comprising cholangiocytes produced as described herein in solution or in a biocompatible scaffold, and a method of making a pharmaceutical composition comprising admixing such cholangiocytes with a pharmaceutically acceptable excipient, vehicle, carrier or biodegradable scaffold, and optionally one or more other ingredients.

A pharmaceutical composition containing cholangiocytes expanded in accordance with the invention may comprise one or more additional components. Pharmaceutical compositions may comprise, in addition to the cholangiocytes, a pharmaceutically acceptable excipient, carrier, buffer, preservative, stabiliser, anti-oxidant, or other material well known to those skilled in the art. Such materials should be non-toxic and should not interfere with the activity of the cholangiocytes. The precise nature of the carrier or other material will depend on the route of administration.

Liquid pharmaceutical compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included.

The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using artificial cerebrospinal fluid.

Another aspect of the invention provides a method of treatment of a biliary disorder or a liver disease comprising administering a population of cholangiocytes produced as described herein to an individual in need thereof.

Another aspect of the invention provides a population of cholangiocytes produced as described herein for use in a method of treatment of a biliary disorder or a liver disease in an individual in need thereof comprising administering a the population to the individual.

Another aspect of the invention provides the use of a population of cholangiocytes produced as described herein in the manufacture of a medicament for use in the treatment of a biliary disorder or a liver disease.

The cholangiocytes may be in the form of organoids, sub-organoid assemblies or clusters or individual cells.

A biliary disorder is a condition in which the biliary tissue in an individual is damaged, defective or otherwise dysfunctional, for example, disorders characterised by damage to or destruction of bile ducts, aberrant bile ducts or the absence of bile ducts. Biliary disorders may include biliary tissue injury, ischaemic strictures, traumatic bile duct injury and cholangiopathies, for example inherited, developmental, autoimmune and environment-induced cholangiopathies, such as Cystic Fibrosis associated cholangiopathy, drug induced cholangiopathy, Alagille Syndrome, polycystic liver disease, primary biliary cirrhosis (PBC), primary sclerosing cholangitis (PSC), AIDS associated cholangiopathy, disappearing bile duct syndrome, biliary cancer, ductopenias such as adult idiopathic ductopenia, post-operative biliary complications, biliary atresia and other disorders of the extra- or intrahepatic bile ducts.

In some embodiments, an expanded population of cholangiocytes may be administered to the individual in solution. The administration of a population of cholangiocytes in solution may be useful for example in the treatment of liver disease, ductopenias, for example ischaemic ductopenia, congenital ductopenia, such as alagille syndrome, metabolic ductopenia, complex diseases, such as intrahepatic PSC and PBC, drug induced ductopenia, vanishing bile duct syndrome and conditions affecting the intrahepatic biliary tree In other embodiments, a population of cholangiocytes may be administered to the individual within a biocompatible scaffold. For example, a scaffold populated with cholangiocytes may be administered to the individual. The administration of a population of cholangiocytes in a scaffold may be useful for example in the treatment of biliary atresia, biliary strictures, traumatic or iatrogenic biliary injury and conditions affecting the extrahepatic biliary tree Cholangiocytes in solution or in scaffolds may be implanted into a patient by any technique known in the art (e.g. Lindvall, O. (1998) Mov. Disord. 13, Suppl. 1:83-7; Freed, C. R., et al., (1997) Cell Transplant, 6, 201-202; Kordower, et al., (1995) New England Journal of Medicine, 332, 1118-1124; Freed, C. R., (1992) New England Journal of Medicine, 327, 1549-1555, Le Blanc et al, Lancet 2004 May 1; 363(9419):1439-41). In particular, cell suspensions may be injected or infused into the bile duct, gallbladder, portal vein, liver parenchyma, peritoneal cavity or spleen of a patient. A cholangiocyte suspension may be administered intravenously, intraperitoneally or via an endoscopic retrograde cholangio-pancreatography (ERCP) or percutaneous cholangiography (PTC). A scaffold populated with cholangiocytes may be administered to the individual by surgical implantation.

Administration of a composition in accordance with the present invention is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors.

A composition comprising cholangiocytes may be administered alone or in combination with other treatments, either simultaneously or sequentially dependent upon the condition to be treated.

Other aspects of the invention relate to the use of cholangiocytes expanded as described herein to determine the susceptibility of a patient to a drug. A method may comprise
(i) providing a population of isolated primary cholangiocytes from an individual with a disease condition, such as a biliary disorder or liver disease and;
(ii) culturing the population in an expansion medium comprising epidermal growth factor (EGF), a canonical Wnt signalling inhibitor and a non-canonical Wnt/PCP signalling potentiator, to produce an expanded population of cholangiocytes displaying a disease phenotype,
(iii) contacting the expanded population of cholangiocytes produced by a method described herein with a therapeutic compound, and;
(iv) determining the effect of the therapeutic compound on said cholangiocytes,
wherein an amelioration of the disease phenotype of the cholangiocytes is indicative that the individual is susceptible to the therapeutic compound.

The proliferation, growth, viability or bile acid resistance of cholangiocytes, their ability to perform one or more cell or organoid functions as described below or their ability to perform one or more of (i) engraft to a non-human animal model following transplantation (ii) form bile ducts in vivo in a non-human animal model, (iii) rescue the disease phenotype in vivo in a non-human animal model (iv) prolong survival of a non-human animal model after transplantation, (v) maintain cell function in vivo in a non-human animal model, (vi) reverse ductopenia in vivo, and (vii) improve serum liver function markers following transplantation in a non-human animal model, may be determined in the presence relative to the absence of the therapeutic compound.

An increase in the ability of the expanded cholangiocytes with the disease phenotype to perform one or more of these functions in the presence relative to the absence of the therapeutic compound is indicative that the compound has a ameliorative effect on the disease in the individual.

Populations of isolated cholangiocytes produced as described above may be useful in modelling the interaction of test compounds with cholangiocytes, for example in toxicity screening, modelling biliary disorders or screening for compounds with potential therapeutic effects.

In some embodiments, cholangiocytes may be obtained from healthy primary tissue. In other embodiments, cholangiocytes may be obtained from primary tissue from a donor with a biliary disease and may display a disease phenotype.

Another aspect of the invention provides the use of a population of cholangiocytes derived from a normal patient or a patient with a biliary disorder for disease modelling and study of pathogenesis of biliary disorders.

Cholangiocytes for use in modelling and screening may be in the form of organoids (cholangiocyte organoids), sub-organoid clusters or individual cells (cholangiocytes) produced, for example by disruption of cholangiocyte organoids.

A method of screening a compound may comprise;
contacting a population of cholangiocytes produced by a method described herein with a test compound, and;
determining the effect of the test compound on said cholangiocytes and/or the effect of said the cholangiocytes on the test compound.

The proliferation, growth, viability or bile acid resistance of cholangiocytes, or their ability to perform one or more cell or organoid functions may be determined in the presence relative to the absence of the test compound.

A decrease in proliferation, growth, viability or ability to perform one or more cell or organoid functions is indicative that the compound has a toxic effect and an increase in growth, viability or ability to perform one or more cell or organoid functions is indicative that the compound has an ameliorative effect on the cholangiocytes.

In some embodiments, the cholangiocytes may be derived from biliary tumours and the effect of the test compound on the proliferation, growth, viability or ability to perform one or more cell or organoid functions of the tumour derived cells may be determined.

Gene expression may be determined in the presence relative to the absence of the test compound. For example, the expression of one or more biliary marker genes may be determined. Combined decrease in expression is indicative that the compound has a toxic effect or can modify the functional state of the cholangiocytes. Gene expression may be determined at the nucleic acid level, for example by RT-PCR, or at the protein level, for example, by immunological techniques, such as ELISA, or by activity assays. Cytochrome p450 assays, for example, luminescent, fluorescent or chromogenic assays are well known in the art and available from commercial suppliers.

In some embodiments, the expression of risk loci for a biliary disease or genes associated with a biliary disease, for example a disease described above, may be determined.

The metabolism, degradation, or breakdown of the test compound by the cholangiocytes may be determined. In some embodiments, changes in the amount or concentration of test compound and/or a metabolite of said test compound may be determined or measured over time, either continuously or at one or more time points. For example, decreases in the amount or concentration of test compound and/or increases in the amount or concentration of a metabolite of said test compound may be determined or measured. In some embodiments, the rate of change in the amount or concentration of test compound and/or metabolite may be determined. Suitable techniques for measuring the amount of test compound or metabolite include mass spectrometry.

This may be useful in determining the in vivo half-life, toxicity, efficacy or other in vivo properties of the test compound.

One or more functions of the cholangiocytes may be determined and/or measured in the presence relative to the absence of the test compound. For example, the ability of the cholangiocytes to perform one or more of MDR1 function; bile acid transfer; VEGF, acetylcholine or ATP responses; CFTR mediated chloride transport; GGT activity, ALP activity or secretin or somatostatin responses, forskolin-induced swelling (Dekkers et al Nat Med 2013; 19:939-45) bile resistance, bicarbonate secretion, lumen integrity (i.e. does the compound does the compound break tight junctions and collapse the lumen of an organoid), transfer of compound in and out of the organoid lumen and the presence or viability of bacteria in the lumen, may be determined and/or measured. The ability of the cholangiocytes to assemble into cholangiocyte organoids may also be determined.

A decrease in the ability of the cholangiocytes to perform one or more of these functions in the presence relative to the absence of the test compound is indicative that the compound has a toxic effect on the biliary epithelium. An increase in the ability of the cholangiocytes to perform one or more of these functions in the presence relative to the absence of the test compound is indicative that the compound has a pro-biliary effect (e.g. it promotes the activity of the biliary epithelium).

Another aspect of the invention provides a kit for production of cholangiocyte organoids comprising an expansion medium comprising epidermal growth factor (EGF), a non-canonical Wnt/PCP signalling potentiator and a canonical Wnt signalling inhibitor.

Suitable expansion media are described in more detail above.

The kit may further comprise a scaffold matrix, such as Matrigel™. The scaffold matrix may be provided as part of the expansion medium or may be provided separately.

The expansion medium may be formulated in deionized, distilled water. The expansion medium will typically be sterilized prior to use to prevent contamination, e.g. by ultraviolet light, heating, irradiation or filtration. The one or more media may be frozen (e.g. at −20° C. or −80° C.) for storage or transport. The one or more media may contain one or more antibiotics to prevent contamination.

The kit may further comprise a sampler, such as a brush or scrapper, for the isolation of primary cholangiocytes from primary bile tissue. The kit may further comprise plates or vessels for mechanical isolation of cholangiocytes from tissue samples and centrifuge tubes for separating cells from tissue debris.

The kit may further comprise a preservation medium to preserve the tissue before the extraction of the cells. Suitable media include UW solution (e.g. Vivaspin™) and William's E medium supplemented with pro-survival cytokines and/or Rock inhibitor.

The kit may further comprise a wash medium. Suitable wash media may include William's E medium supplemented with EGF and Rock inhibitor.

The kit may further comprise pro-survival cytokines such as ROCK-inhibitors

The kit may further comprise a plate heater.

The kit may further comprise cryopreservation solution. Suitable cryopreservation media are described above.

The one or more media may be a 1× formulation or a more concentrated formulation, e.g. a 2× to 250× concentrated medium formulation. In a 1× formulation each ingredient in the medium is at the concentration intended for cell culture, for example a concentration set out above. In a concentrated formulation one or more of the ingredients is present at a higher concentration than intended for cell culture. Concentrated culture media are well known in the art. Culture media can be concentrated using known methods e.g. salt precipitation or selective filtration. A concentrated medium may be diluted for use with water (preferably deionized and distilled) or any appropriate solution, e.g. an aqueous saline solution, an aqueous buffer or a culture medium.

The one or more media in the kit may be contained in hermetically-sealed vessels.

Hermetically-sealed vessels may be preferred for transport or storage of the culture media, to prevent contamination. The vessel may be any suitable vessel, such as a flask, a plate, a bottle, a jar, a vial or a bag.

Another aspect of the invention provides a use of an expansion medium for the in vitro expansion of primary cholangiocytes, wherein the expansion medium comprises epidermal growth factor (EGF), a non-canonical Wnt signalling potentiator and a canonical Wnt signalling inhibitor.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

Experiments

1. Methods 1.1 Primary Biliary Tissue

Primary biliary tissue (bile duct or gallbladder) was obtained from deceased organ donors from whom organs were being retrieved for transplantation. The gallbladder or a section of the bile duct was excised during the organ retrieval operation after obtaining informed consent from the donor's family (REC reference numbers: 12/EE/0253, NRES Committee East of England—Cambridge Central and 15/EE/0152 NRES Committee East of England—Cambridge South).

1.2 Isolation of Primary Cholangiocytes

Excised bile duct segments were placed in a 10 cm plate and washed once with William's E medium (Gibco, Life Technologies). A longitudinal incision was made along the wall of the excised bile duct segment exposing the lumen and 10-15 ml of William's E medium were added to cover the tissue. The luminal epithelium was scraped off using a surgical blade, while submerged in medium. The supernatant was collected and the tissue and plate were washed 2-3 times with William's E medium to harvest any remaining cells. The supernatant and washes were centrifuged at 444 g for 4 minutes. The pellet was washed with William's E, re-centrifuged and the supernatant was discarded.

Excised gallbladders were placed in a 15 cm plate, a longitudinal incision was made along the wall of the excised gallbladder and the lumen was washed once with William's E medium (Gibco, Life Technologies). Cholangiocytes were isolated and harvested following the method described above.

For isolation through brushings, an excised bile duct segment was placed in a 10 cm plate and cannulated using an ERCP brush. The lumen was brushed 10-20 times and the cells were harvested by washing the brush several times in a falcon tube containing 40-50 ml of William's E medium.

1.3 Generation and Culture of ECOs

Isolated primary cholangiocytes were centrifuged at 444 g for 4 minutes and re-suspended in a mixture of 66% matrigel (BD Biosciences, catalogue number: 356237) and 33% William's E medium (Gibco, Life Technologies) supplemented with 10 mM nicotinamide (Sigma-Aldrich), 17 mM sodium bicarbonate (Sigma Aldrich), 0.2 mM 2-Phospho-L-ascorbic acid trisodium salt (Sigma-Aldrich), 6.3 mM sodium pyruvate (Invitrogen), 14 mM glucose (Sigma-Aldrich), 20 mM HEPES (Invitrogen), ITS+ premix (BD Biosciences), 0.1 µM dexamethasone (R&D Systems), 2 mM Glutamax (Invitrogen),100 U/ml penicillin per 100 µg/ml streptomycin, 20 ng/ml EGF (R&D Systems), 500 ng/ml R-Spondin (R&D Systems) and 100 ng/ml DKK-1 (R&D Systems). The cell suspension was plated in 24-well plate format, at 50 µl/well, so that a small dome of matrigel was formed in the centre of each well and then incubated at 37° C. for 10-30 minutes until it solidified. 1 ml of William's E medium with supplements was added. The culture medium was changed every 48 hours.

To split the cells, the matrigel was digested by adding Cell Recovery Solution (Corning) for 30 minutes at 4° C. The resulting cell suspension was harvested, centrifuged at 444 g for 4 minutes, washed once with William's E medium and re-suspended in 66% matrigel and 33% William's E medium with supplements, as described above.

All experiments were performed using passage 20 ECOs unless otherwise stated.

1.4 Cell Line Identity

Demographic data for donor corresponding to the each ECO lines is provided in the table below. Following derivation ECO lines were authenticated by matching their karyotype to the sex of the donor of origin. The lines were tested on a regular basis and found to be negative for mycoplasma contamination.

TABLE 1

Donor Demographics

| Donor type | Blood Group | Age (years) | Gender | Site |
|---|---|---|---|---|
| DCD | O− | 33 | F | CBD |
| DBD | O+ | 56 | F | CBD |
| DCD | A− | 77 | M | CBD |
| DBD | O+ | 57 | M | CBD, GB |
| DCD | O− | 44 | M | CBD, GB |

TABLE 1-continued

Donor Demographics

| Donor type | Blood Group | Age (years) | Gender | Site |
|---|---|---|---|---|
| DCD | O+ | 48 | M | CBD |
| DBD | A+ | 36 | M | BR |
| DBD | B+ | 48 | F | BR |

DCD: Donation after 2 Circulatory Death,
DBD: Donation after Brainstem Death,
F: Female,
M: male,
CBD: 3 Common Bile Duct,
GB: Gallbladder,
BR: CBD Brushings 1.5 Immunofluorescence, RNA Extraction and Quantitative Real Time PCR IF, RNA extraction and QPCR were performed as described in Sampaziotis F. et al. (*Biotechnol.* 2015 1-11, doi: 10.1038/nbt.3275).

All QPCR data are presented as the median, interquartile range (IQR) and range (minimum to maximum) of four independent ECO lines unless otherwise stated. Values are relative to the housekeeping gene Hydroxymethylbilane Synthase (HMBS).

All IF images were acquired using a Zeiss Axiovert 200M inverted microscope or a Zeiss LSM 700 confocal microscope. Imagej 1.48k software (Wayne Rasband, NIHR, USA, http://imagej.nih.gov/ij) was used for image processing.

1.6 Microarrays

RNA for microarray analysis was collected from 3 different ECO lines (n=3). The RNA was assessed for concentration and quality using a SpectroStar (BMG Labtech, Aylesbury, UK) and a Bioanalyser (Agilent Technologies, Cheadle, UK). Microarray experiments were performed at Cambridge Genomic Services, University of Cambridge, using the HumanHT-12 v4 Expression BeadChip (Illumina, Chesterford, UK) according to the manufacturer's instructions. Briefly, 200 ng of Total RNA underwent linear amplification using the Illumina TotalPrep RNA Amplification Kit (Life Technologies, Paisley, UK) following the manufacturer's instructions. The concentration, purity and integrity of the resulting cRNA were measured by SpectroStar and Bioanalyser. Finally cRNA was hybridised to the Human HT-12 v4 BeadChip overnight followed by washing, staining and scanning using the Bead Array Reader (Illumina). Raw data was loaded into R using the lumi package from Bioconductor (Du P et al.; *Bioinformatics* 2008 24:1547-8) and divided into subsets according to the groups being compared; only the samples involved in a given comparison are used. Subsets were then filtered to remove any non-expressed probes using the detection p-value from Illumina. Across all samples probes for which the intensity values were not statistically significantly different (P>0.01) from the negative controls were removed from the analysis. Following filtering the data was transformed using the Variance Stabilization Transformation (Lin et al., *Nucliec Acids Res.* 2008, 36) from lumi and then normalised to remove technical variation between arrays using quantile normalisation. Comparisons were performed using the limma package (Smyth G K, *Stat Appl Genet Mol Biol* 2004 3) with results corrected for multiple testing using False Discovery Rate (FDR) correction. Finally the quality of the data was assessed along with the correlations between samples within groups.

Probes differentially expressed between HEP and ECOs representing the aggregate transcriptional "signature" of ECOs were selected for Euclidean hierarchical clustering using Perseus software (MaxQuant). Standard scores (z-scores) of the log 2 normalized probe expression values across the different conditions were calculated and used for this analysis. Heatmaps and Primary Component Analysis (PCA) plots were generated using the MaxQuant Perseus software (Tyanova S et al., *Nat. Methods* 2016 13:731-40). Functional annotation and gene ontology analyses were performed on the genes differentially expressed between PCs and ECOs (FIG. 1d) using the NIAID/NIH Database for Annotation, Visualization and Integrated Discovery (DAVID) v6.8 (Huang D. W. et al., *Nat. Protoc.* 2008, 4:44-57).

1.7 Western Analysis

Total protein was extracted with lysis buffer (50 mM Tris pH 8, 150 mM NaCl, 0.1% SDS, 0.5% sodium deoxycholate, 1% Trition X-100 and protease and phosphatase inhibitors). Protein concentrations were determined by BCA Protein Assay Kit (Thermo Fisher Scientific) according to the manufacturer's instructions. Samples were prepared for Western blot by adding 1× NuPAGE LDS Sample Buffer with 1% 3-mercaptoethanol and incubated for 5 minutes at 95° C. Protein (25 µg) was separated by 4-12% NuPAGE Bis-Tris protein gels (Invitrogen) and transferred onto PVDF membranes (Bio-Rad). Proteins were detected by probing with antibodies specific to Phospho-β-catenin (Ser33/37/Thr41) (Cell Signalling Technology), Active-β-catenin (Millipore), Total-β-catenin (R&D), α-tubulin (Sigma) followed by incubation with horseradish peroxidase anti-mouse, anti-goat or anti-rabbit secondary antibodies. Membranes were developed using Pierce ECL Western blotting substrate (Thermo Scientific) according to the manufacturer's instructions.

1.8 Rho Kinase Activity Analyses

Rho Kinase activity was measured using a commercially available kit (Cell Biolabs, STA-416) according to the manufacturer's instructions 1.9 Flow Cytometry Analyses ECO organoids were harvested using Cell Recovery Solution (Corning) for 30 minutes at 4° C., centrifuged at 444 g for 4 minutes and dissociated to single cells using TrypLETM Express (Gibco). The cells were fixed using 4% PFA for 20 minutes at 4° C. Cell staining and flow cytometry analyses were performed as described in Sampaziotis F. et al. (*Biotechnol.* 2015 1-11, doi: 10.1038/nbt.3275) and Bertero A. et al. (*Genes Dev.* 2015 29:702-17).

1.10 Karyotyping

ECO organoids were harvested using Cell Recovery Solution (Corning), dissociated to single cells as described above, plated in gelatin coated plates and cultured using William's E medium with supplements. When the cells were sub-confluent, usually after 72 hrs, the cultures were incubated for 3-4 hours with William's E medium with supplements containing 0.1 µg/ml colcemid (Karyomax®, Gibco). The cells were then harvested using Trypsin-EDTA (0.05%) (Gibco) for 4-5 minutes at 37° C., centrifuged at 344 g for 5 minutes and re-suspended in 5 mls of KCl hypotonic solution (0.055M). The suspension was re-centrifuged at 344 g for 5 minutes, 2 mls of a 3:1 100% methanol:glacial acetic acid solution were added and slides were prepared as described (Campos P. B. et al., *J. Vis. Exp* 2009 4-7).

1.11 Comparative Genomic Hybridization Analyses

Genomic DNA was labelled using the BioPrime DNA Labeling Kit (Invitrogen), according to the manufacturer's instructions and samples were hybridised to Agilent Sureprint G3 unrestricted CGH ISCA 8×60K human genome arrays following the manufacturer's protocol. The data was analysed using the Agilent CytoGenomics Software.

1.12 Rhodamine123 Transport Assay

The Rhodamine 123 transport assay was performed as described in Sampaziotis F. et al. (*Nat. Biotechnol.* 2015, 1-11) and images were acquired using a Zeiss LSM 700 confocal microscope. Fluorescence intensity was measured between the organoid interior and exterior and luminal fluorescence was normalized over the background of the extraluminal space. Each experiment was repeated in triplicate. Error bars represent standard deviation.

1.13 Cholyl-Lysyl-Fluorescein Transport Assay

To achieve loading with Cholyl-Lysyl-Fluorescein (CLF, Corning Incorporated), ECO organoids were split in 5 µM of CLF and incubated at 37° C. for 30 minutes. Images were acquired using a Zeiss LSM 700 confocal microscope and fluorescence intensity was measured between the organoid interior and exterior as described for the Rhodamine 123 transport assay. To demonstrate that the changes in CLF fluorescence intensity observed were secondary to active export of CLF from the organoid lumen, the experiment was repeated with 5 µM of unconjugated Fluorescein Isothiocyanate (FITC) (Sigma-Aldrich) as a control. Fluorescence intensity measurements were performed as described for the Rhodamine 123 transport assay.

1.14 GGT Activity

GGT activity was measured in triplicate using the MaxDiscovery™ gamma-Glutamyl Transferase (GGT) Enzymatic Assay Kit (Bioo scientific) based on the manufacturer's instructions. Error bars represent standard deviation.

1.15 Alkaline Phosphatase Staining

Alkaline phosphatase was carried out using the BCIP/NBT Color Development Substrate (5-bromo-4-chloro-3-indolyl-phosphate/nitro blue tetrazolium) (Promega) according to the manufacturer's instructions.

1.16 Response to Secretin and Somatostatin

Responses to secretin and somatostatin were assessed as described in Sapazoits F, et al. (*Biotechnol.* 2015 1-11).

1.17 Generation of ECOs Expressing Green Fluorescent Protein

EGFP expressing VSV-G pseudotyped, recombinant HIV-1 lentiviral particles were produced with an optimized second generation packaging system by transient co-transfection of three plasmids into HEK 293T cells (ATCC CRL-11268). EGFP expression is under control of a core EF1a-promoter. All plasmids were a gift from Didier Trono and obtained from addgene (pWPT-GFP #12255, psPAX2 #12260, pMD2. G, #12259). Viral infection of organoids was performed as described in Koo, B-K, et al. (*Curr. Protoc. Stem Cell Biol.* 2013, 27 Unit 5A.6). Infected ECOs were expanded for 2 passages, harvested as described above for flow cytometry analyses and cell sorting by flow cytometry for GFP positive cells was performed. GFP expressing single cells were plated using our standard plating method and cultured in William's E medium with supplements for 1-2 weeks until fully grown ECO organoids developed.

1.18 Generation of ECO Populated PGA Scaffolds 1 mm thick PolyGlycolic Acid (PGA) scaffolds with a density of 50 mg/cc were used for all experiments. Prior to seeding cells, the PGA scaffolds were pre-treated with a 1M NaOH for 10-30 seconds washed 3 times, decontaminated in a 70% ethanol solution for 30 minutes and then air-dried for another 30 minutes until all the ethanol had fully evaporated. All scaffolds were obtained from Biomedical Structures (Biofelt).

ECOs were harvested and dissociated to single cells as previously described for flow cytometry analyses. 5-10×106 cells were re-suspended in 100 μl of William's E medium with supplements, seeded on a scaffold surface area of 1 cm2 and incubated at 37° C. for 30-60 minutes to allow the cells to attach to the scaffold. The scaffolds were placed in wells of a 24-well plate and checked at regular intervals during this period to ensure the medium did not evaporate. If necessary, 10-20 μl of William's E medium with supplements were added. After 1 hour, 2-3 mls of William's E medium with supplements were added to the wells and the medium was changed twice weekly.

1.19 Generation of Densified Collagen Tubes

Densified collagen tubes were prepared using a novel approach. A 3D printed chamber was fabricated, consisting of a funnel piece and a base plate. A 250 μm thick metallic wire was mounted into the base plate and fed through the centre of the funnel. Absorbent paper towels were compacted between the two 3D printed parts, which were then screwed together. 5 mg mL−1 collagen gel solution, loaded with cells, was poured into the funnel and gelled at 37° C. for 30 min. After that time, the screws were loosened and, by placing the 3D printed chambers at 37° C. for 2-4 h, water was drawn out of the collagen gel. A cell-loaded densified collagen tube was thus formed with a 250 μm lumen and a wall thickness of 30-100 μm, determined by the duration of the drying phase. Upon removal from the chamber, the tube was trimmed for excess collagen and cut to the required length.

1.20 Culture of Human Mammary Epithelial Cells (HMECs)

HMECs and the required tissue culture consumables were purchased as a kit from Lonza (cat no. CC-2551B) and the cells were cultured according to the supplier's instructions 1.21 Animal Experiments All animal experiments were performed in accordance with UK Home Office regulations (UK Home Office Project License numbers PPL 80/2638 and PPL 70/8702). Immunodeficient NOD.Cg-Prkdcscid Il2rgtm1Wjl/SzJ (NSG) mice which lack B, T and NK lymphocytes (Shultz L. D. et al., *J. Immunol.* 2005 174:6477-6489) were bred in-house with food and water available ad libitum pre- and post-procedures. A mix of male and female animals were used, aged approximately 6-8 weeks. All the ECO-constructs used were populated with ECOs derived from the common bile duct.

1.22 Generation of Extra-Hepatic Biliary Injury (EHBI) Mouse Model

To generate a model of extrahepatic biliary injury, midline laparotomy was performed and the gallbladder was first mobilized by dividing the ligamentous attachment connecting its fundus to the anterior abdominal wall under isoflurane general anesthesia. A longitudinal incision was then made along ⅔ of the length of the gallbladder, from the fundus towards Hartmann's pouch (neck of gallbladder).

1.23 Biliary Reconstruction in EHBI Mice

To reconstruct the gallbladder, a scaffold section measuring approximately 1×1 mm (seeded with ECOs or without ECOs in controls) was sutured as a 'patch' to close the defect using 4-6 interrupted 10'0 non-absorbable nylon sutures under 40× magnification. The laparotomy was closed in two layers with continuous 5'0 absorbable Vicryl sutures. The animals were given buprenorphine (temgesic 0.1 mg/kg) analgesia as a bolus and observed every 15 minutes in individual cages until fully recovered.

1.24 Bile Duct Replacement

The native common bile duct was divided and a short segment excised. The populated densified collagen tube was anastomosed end-to-end, using interrupted 10'0 nylon sutures, between the divided proximal and distal common bile duct. A length of 5'0 nylon suture material (diameter 100 μm) was inserted into the collagen tube and fed into the proximal and distal common bile duct to ensure patency of the lumen during the anastomosis. After the anastomosis was complete, the 5'0 suture was pushed into the duodenum through the distal bile duct and was removed through an incision in the duodenum, which was then closed with interrupted 10'0 nylon sutures. Lumen patency was assessed at the time of transplantation through light microscopy and cannulation of the lumen with a 5'0 non-absorbable suture. Transplantation was abandoned as futile in case of fully occluded tubes due to cell infiltration. These events were considered construct/tube failure rather than surgical complications and therefore were not censored in the survival analysis.

1.25 Bile Duct Ligation

C57BL/6 mice were purchased from The Jackson Laboratory (Bar Harbor, Me.). The mice were housed and bred in a Minimal Disease Unit at the animal facility at Oslo University Hospital, Rikshospitalet, Oslo. All experiments were performed on male mice between 8 and 12 weeks of age. A median laparotomy was performed, the common bile duct exposed and ligated close to the junction of the hepatic bile ducts. Sham operated mice underwent the same procedure without ligation. Serum was harvested after 5 days. Alanine transaminase (ALT), aspartate transaminase (AST) and alkaline phosphatase (ALP) were measured in serum using an ADVIA 1800 (Siemens) at The Central Laboratory, Norwegian School of Veterinary Science. All animal experiments were approved by the Norwegian Food Safety Authority (project license no FOTS 8210/15) and all animals received human care in line with "Guide for the Care and Use of Laboratory Animals" (National Institutes of Health Publication, 8th Edition, 2011).

1.26 Blood Sample Collection & Processing

Blood was taken using a 23 g needles directly from the inferior vena cava under terminal anesthesia at the time the animals were electively culled and transferred into 1.5 ml Eppendorf tubes for further processing.

The blood samples were routinely processed by the University of Cambridge Core biochemical assay laboratory (CBAL). All of the sample analysis was performed on a Siemens Dimension EXL analyzer using reagents and assay protocols supplied by Siemens.

1.27 Light Microscopy Imaging

Light microscopy images of excised reconstructed gallbladders were acquired using a Leica MZFLIII fluorescence dissecting microscope. The images are representative of 5 animals.

1.28 Cryosectioning and Histology

Excised gallbladders were fixed in 4% PFA, immersed in sucrose solution overnight, mounted in optimal cutting temperature (OCT) compound and stored at −80° C. until sectioning. Sections were cut to a thickness of 10 μm using a cryostat microtome and mounted on microscopy slides for further analysis.

1.29 Haematoxylin and Eosin (H&E) Staining

H&E staining was performed using Sigma-Aldrich reagents according to the manufacturer's instructions. Briefly, tissue sections were hydrated, treated with Meyer's Haematoxylin solution for 5 minutes (Sigma-Aldrich), washed with warm tap water for 15 minutes, placed in distilled water for 30-60 seconds and treated with eosin solution (Sigma-Aldrich) for 30-60 seconds. The sections were dehydrated and mounted using the Eukitt® quick-hardening mounting medium (Sigma-Aldrich). Histology sections were reviewed by an independent histopathologist with a special interest in hepatobiliary histology.

1.30 TUNEL Assay

The TUNEL assay was performed using a commercially available kit (abcam, ab66110) according to the manufacturer's instructions.

1.31 Fluorescein Isothiocyanate (FITC) Cholangiography

In situ FITC cholangiography was performed in sacrificed animals after dissection of the gallbladder free from the adherent liver lobes, but before surgical interruption of the extrahepatic biliary tree. The distal bile duct was cannulated with a 23½ gauge needle and FITC injected retrogradely into the gallbladder and images taken under a fluorescent microscope.

1.32 Magnetic Resonance Cholangio-Pancreatography (MRCP)

Magnetic resonance cholangio-pancreatography was performed after sacrifice of the animals. MRCP was performed at 4.7 T using a Bruker BioSpec 47/40 system. A rapid acquisition with relaxation enhancement sequence was used with an echo train length of 40 echoes at 9.5 ms intervals, a repetition time of 1000 ms, field of view 5.84×4.18×4.18 cm3 with a matrix of 256×180×180 yielding an isotropic resolution of 230 µm. The actively-decoupled four-channel mouse cardiac array provided by Bruker was used for imaging.

For the second mouse imaged, for higher signal to noise ratio to give improved visualisation of the biliary ducts a two-dimensional sequence was used with slightly varied parameters (24 spaced echoes at 11 ms intervals to give an effective echo time of 110 ms; repetition time 5741 ms; matrix size of 256×256; field of view of 4.33×5.35 cm$^2$ yielding a planar resolution of 170×200 µm$^2$). Fifteen slices were acquired coronally through the liver and gall bladder with a thickness of 0.6 mm. For this acquisition, a volume coil was used to reduce the impact of radiofrequency inhomogeneity.

To examine the biliary ducts and gall bladder, images were prepared by maximum intensity projections. Structural imaging to rule out neoplastic growths was performed using a T1-weighted 3D FLASH (fast low-angle shot) sequence with a flip angle of 25°, repetition time of 14 ms and an echo time of 7 ms. The matrix was 512×256×256 with a field of view of 5.12×2.56×2.56 cm3 for a final isotropic resolution of 100 µm. The MRCP images were reviewed by 2 independent radiologists with a special interest in hepatobiliary radiology.

1.33 Statistical Analyses

All statistical analyses were performed using Graph Pad Prism 6. For small sample sizes where descriptive statistics are not appropriate, individual data points were plotted. For comparison between 2 mean values a 2-sided Student's t-test was used to calculate statistical significance. The normal distribution of our values was confirmed using the D'Agostino & Pearson omnibus normality test where appropriate. Variance between samples was tested using the Brown-Forsythe test. For comparing multiple groups to a reference group one-way ANOVA with Dunnett correction for multiple comparisons was used between groups with equal variance, while the Kruskal-Wallis test with Dunn's correction for multiple comparisons was applied for groups with unequal variance. Survival was compared using log-rank (Mantel-Cox) tests. Where the number of replicates (n) is given this refers to ECO lines or number of different animals unless otherwise stated.

2. Results 2.1 Human Extrahepatic Cholangiocytes Can Be Propagated as Organoids

Figure 2:
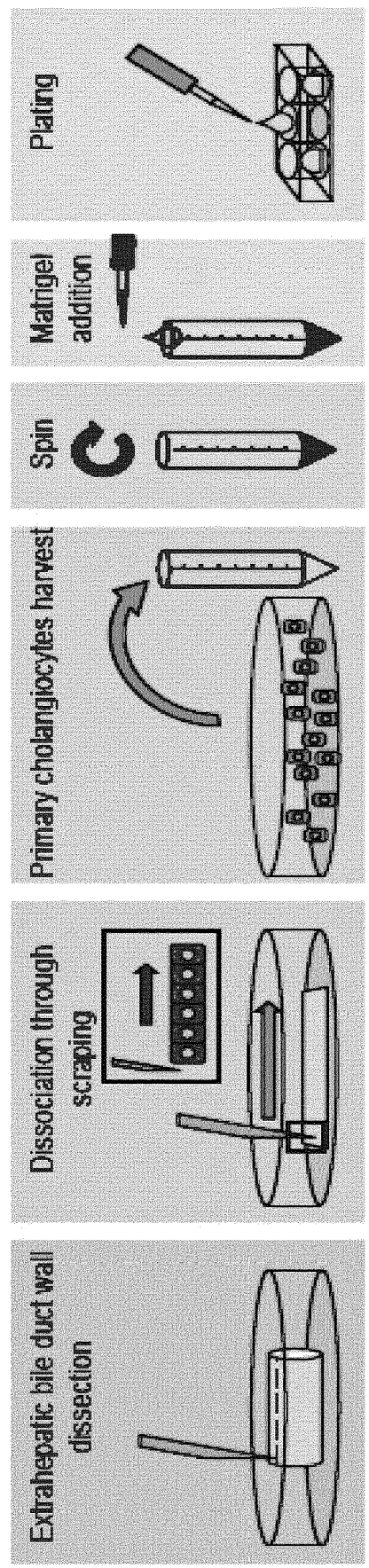
FIG. 2 depicts a schematic representation of the mechanical "scraping" method for derivation of ECOs.
Figure 3:
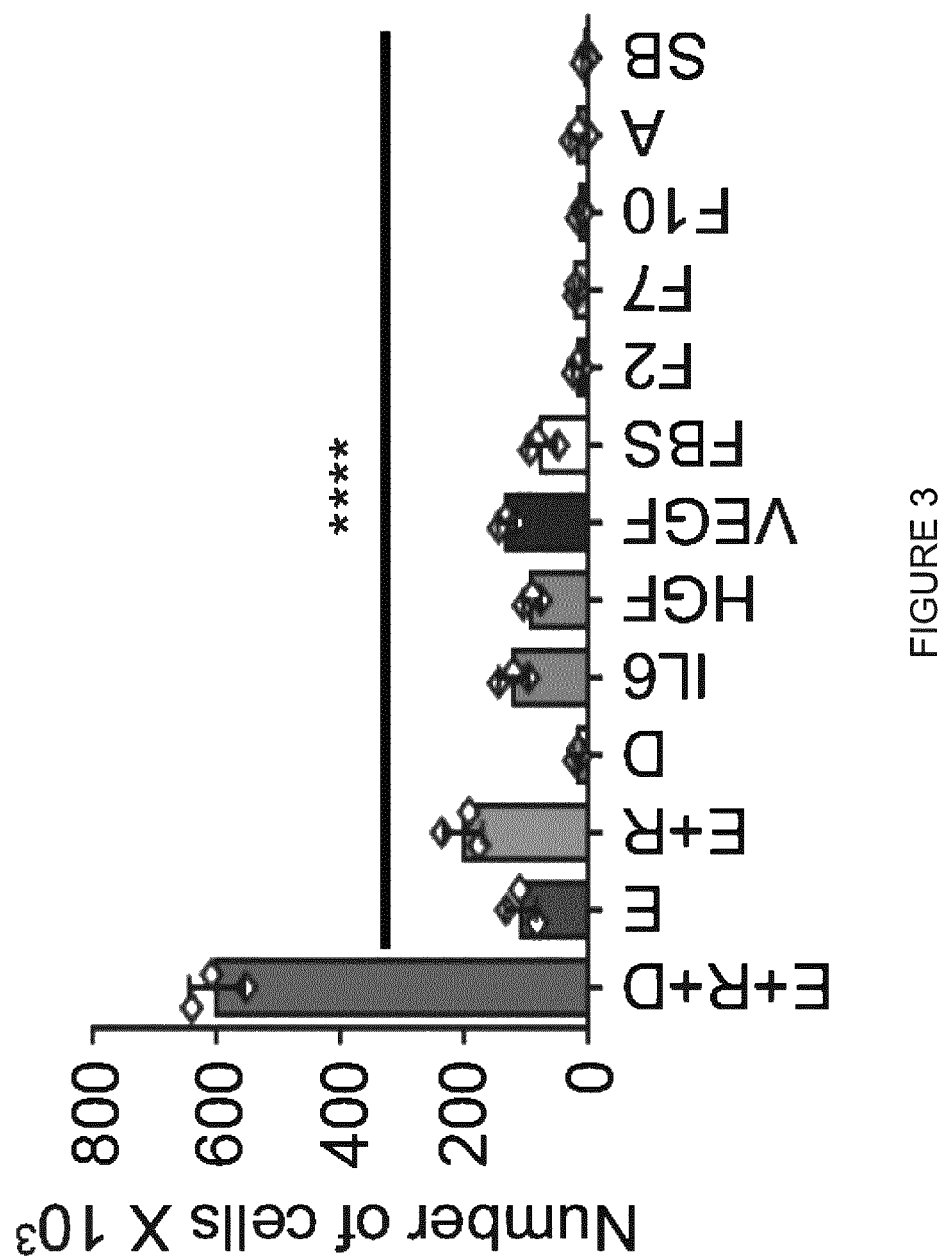
FIG. 3 shows the mean number of resulting cells following 7 days of culture with various growth factors. EGF: Epidermal Growth Factor, R: R-spondin, D: DKK-1, IL6: Interleukin-6, HGF: Hepatocyte Growth Factor, VEGF: Vascular Endothelial Growth Factor, FBS: Foetal Bovine serum, F2: Fibroblast Growth Factor (FGF) 2, F7: FGF-7, F10: FGF-10, A: Activin-A, SB: Activin inhibitor SB-431542. Error bars show standard deviation; n=3. Asterisks represent statistically significant differences in the number of resulting cells between E+R+D and other culture conditions (****P<0.0001; one-way ANOVA with Dunnett correction for multiple comparisons).

We first focused on identifying optimal conditions to isolate primary cholangiocytes from the biliary epithelium which forms a monolayer covering the luminal surface of the biliary tree (Kanno N. et al., *Hepatology* 2000 31:555-61). We tested several approaches for recovering these cells including mechanical scraping and enzymatic digestion by trypsin or collagenase and/or dispase (FIG. 1). Mechanical dissociation by brushing or scraping the bile duct lumen was associated with improved survival compared to enzymatic digestion (FIGS. 1 and 2). Furthermore, the majority of the resulting cells co-expressed the biliary markers CK7 and CK19 (94.6±2.4%, standard deviation; n=3); while no contamination from mesenchymal cell types was detected. Consequently, mechanical dissociation constitutes the optimal method for harvesting extrahepatic cholangiocytes.

Figure 4:
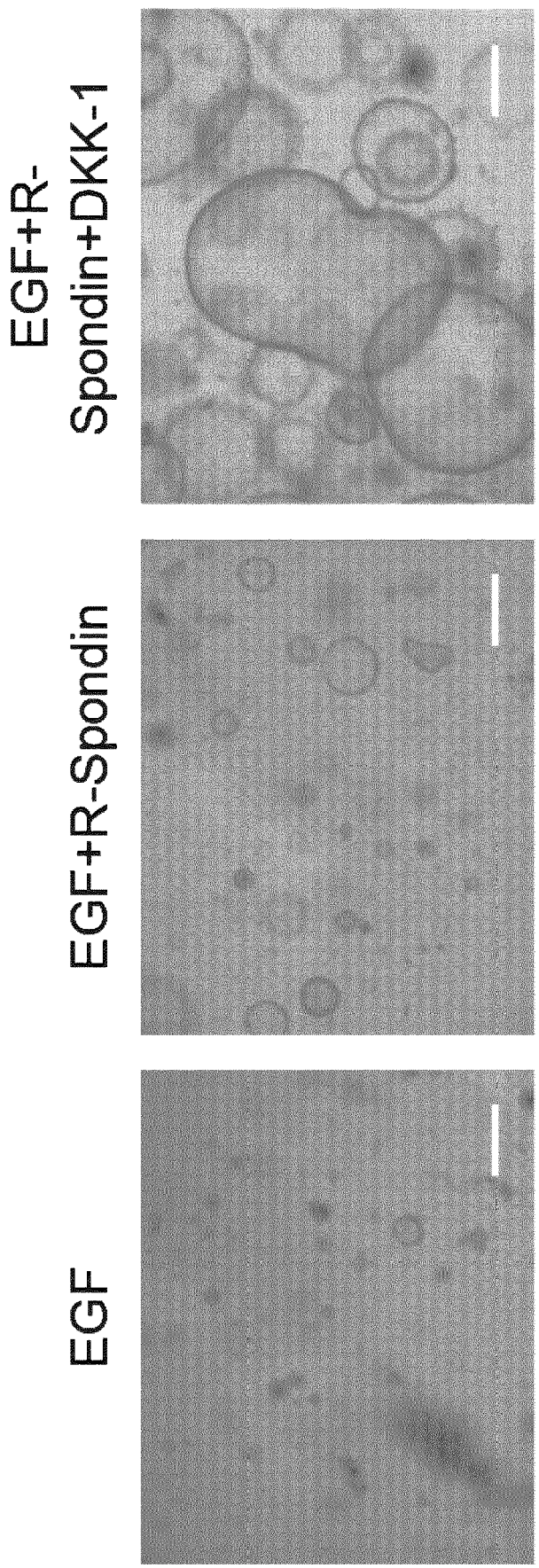
FIG. 4 shows representative live images of freshly isolated primary cholangiocytes grown under different culture conditions for 7 days. EGF: Epidermal Growth Factor. Scale bars: 500 μm.

To discern appropriate conditions for the maintenance and propagation of these cells, we optimized an established system for 3D culture of human induced pluripotent stem cell-derived intrahepatic cholangiocytes (Sampaziotis F. et al., *Biotechnol*. 2015-11; Sampaziotis F. et al., *Nat. Protoc.* 12:814-827). Screening of multiple growth factors known to support expansion of cholangiocytes and epithelial organoids (LeSage, G et al., *Liver* 2001 21:73-80; Huch M et al., *Cell* 2014 160:299-312) identified the combination of Epidermal Growth Factor (EGF), R-spondin and Dickkopf-related protein 1 (DKK-1) as sufficient to promote the growth of primary cholangiocytes into organoids (FIG. 4).

Figure 5:
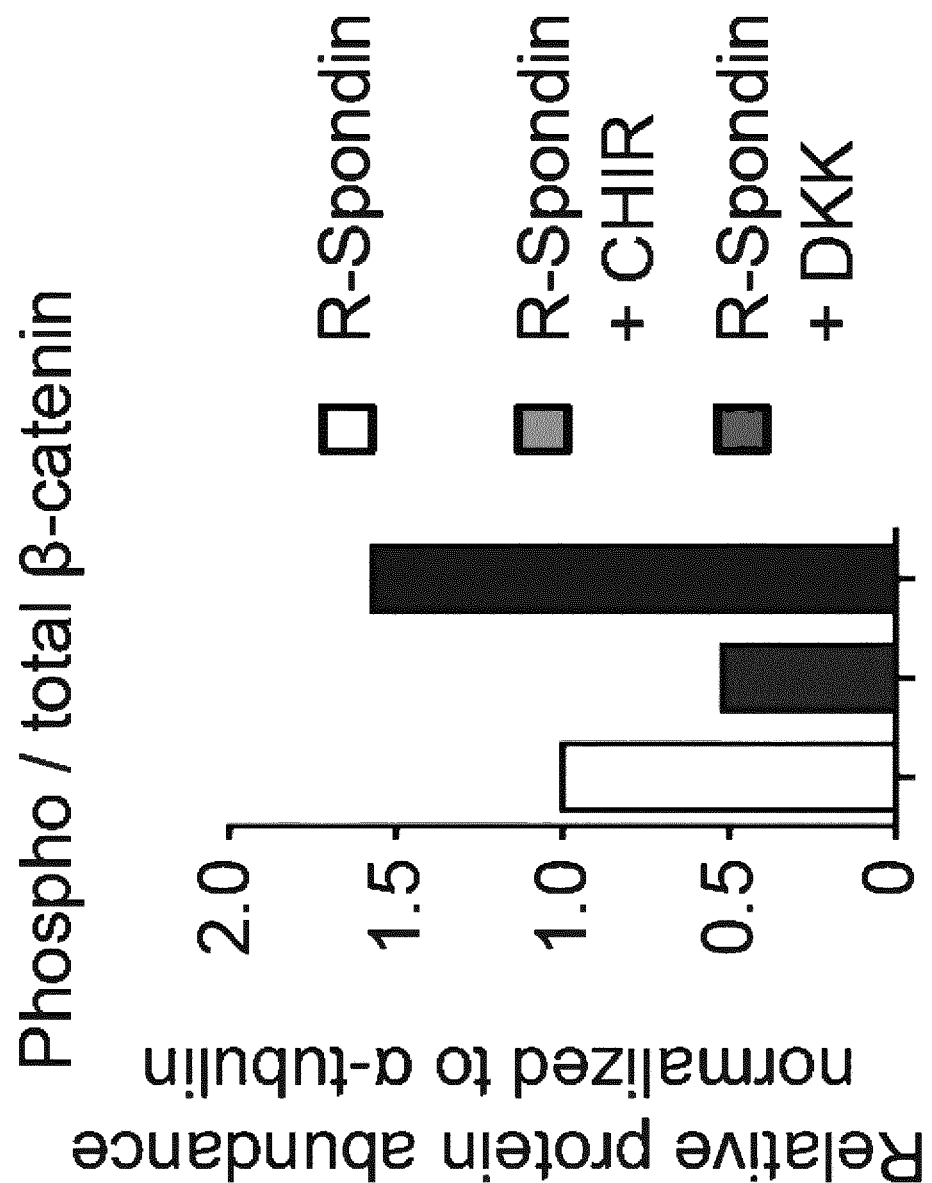
FIG. 5 shows a quantitative Western blot analysis demonstrating increased levels of phosphorylated β-catenin in ECOs treated with R-spondin and DKK when compared to R-spondin alone or R-spondin and the GSK-3 inhibitor CHIR 99021 (CHIR), used as a positive control.
Figure 6:
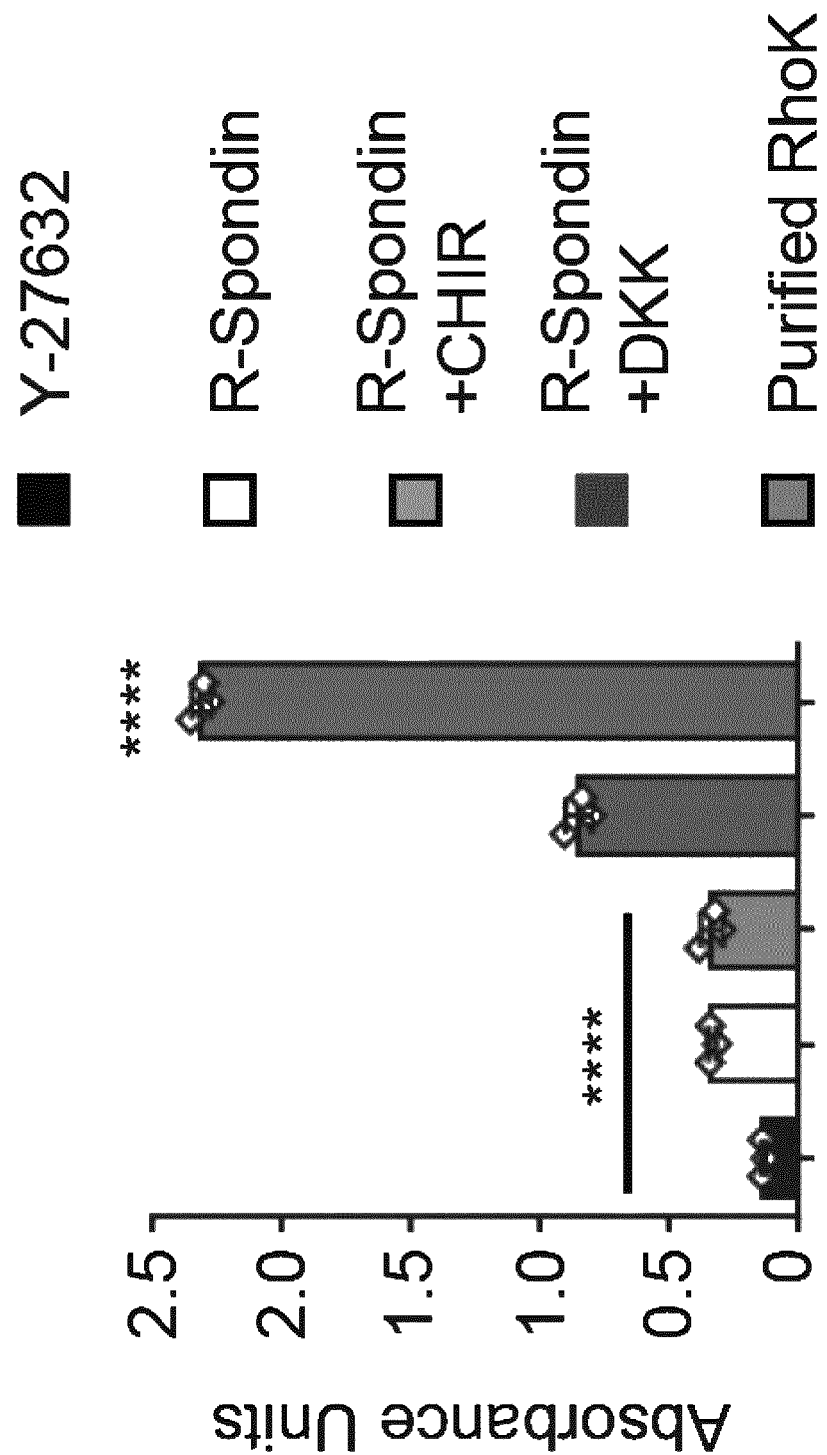
FIG. 6 depicts an assay of Rho Kinase activity in ECOs treated with Rho Kinase inhibitor Y-27632, R-spondin alone, R-spondin and the GSK-3 inhibitor CHIR 99021, or R-spondin and DKK. Purified RhoK is included for reference. This demonstrates that ECOs treated with R-spondin and DKK exhibit increased Rho Kinase activity consistent with non-canonical Wnt signalling/PCP pathway activation. Error bars show standard deviation; ****P<0.0001; one way ANOVA with Dunnett correction for multiple comparisons; n=3.

Due to the seemingly paradoxical requirement for both a Wnt potentiator (R-spondin) and an inhibitor (DKK-1), we characterized the canonical and non-canonical/PCP Wnt pathway activity in ECOs. Our results demonstrate higher β-catenin phosphorylation in ECOs compared to cells treated with R-spondin but no DKK-1 (FIG. 5), signifying lower WNT canonical pathway activity in these cells. Furthermore ECOs exhibit higher Rho Kinase activity compared to cells treated with R-spondin but no DKK-1 (FIG. 6), which is consistent with enhanced non-canonical/PCP signalling in ECOs. Thus, non-canonical Wnt signalling controls ECO expansion marking a notable difference with previous organoid culture conditions (Huch M et al.; *Cell* 2014 160:299-312).

Figure 7:
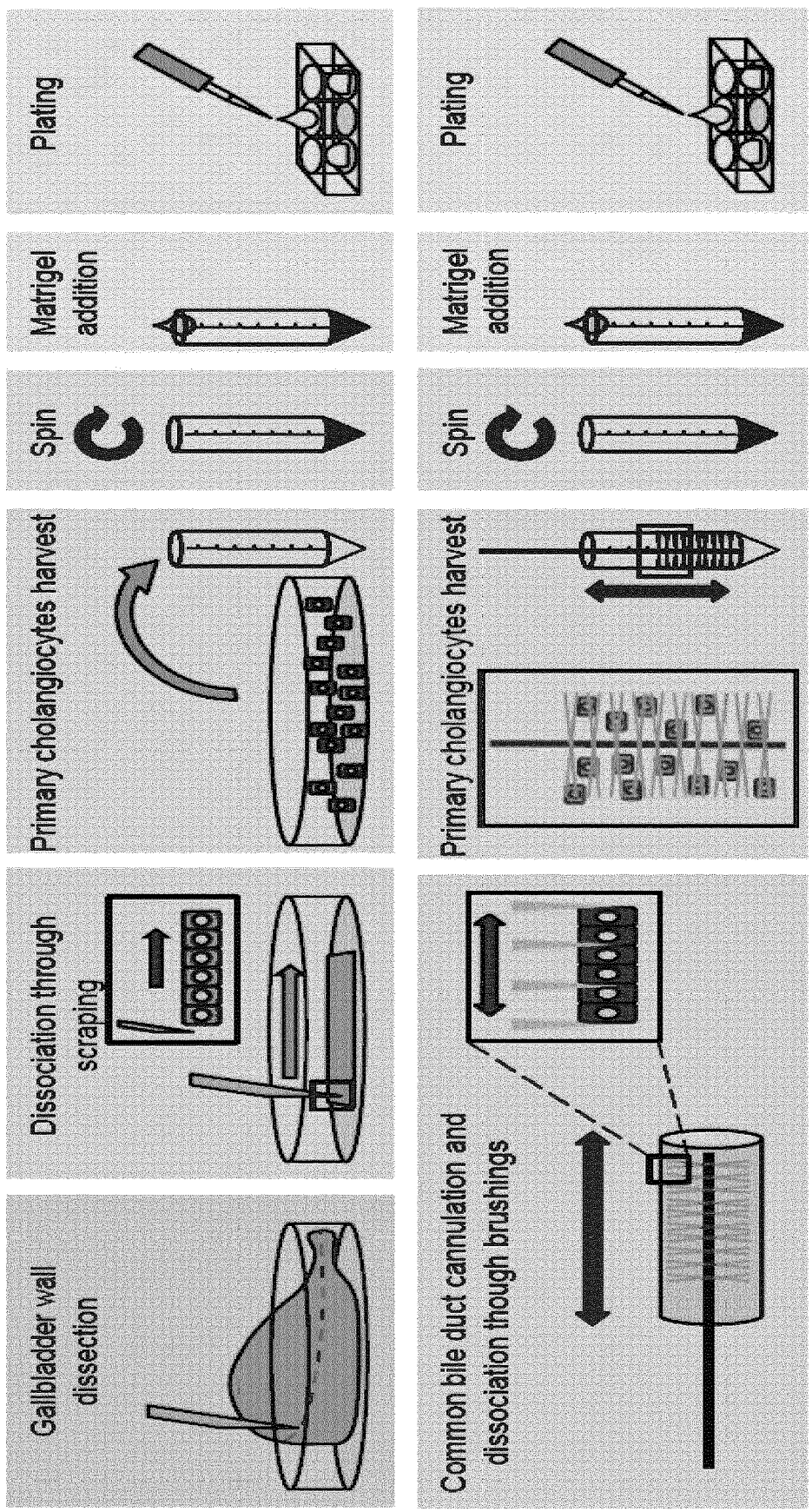
FIG. 7 shows schematic representations of the methods for the derivation of ECOs from the gallbladder and common bile duct brushings.
Figure 27:
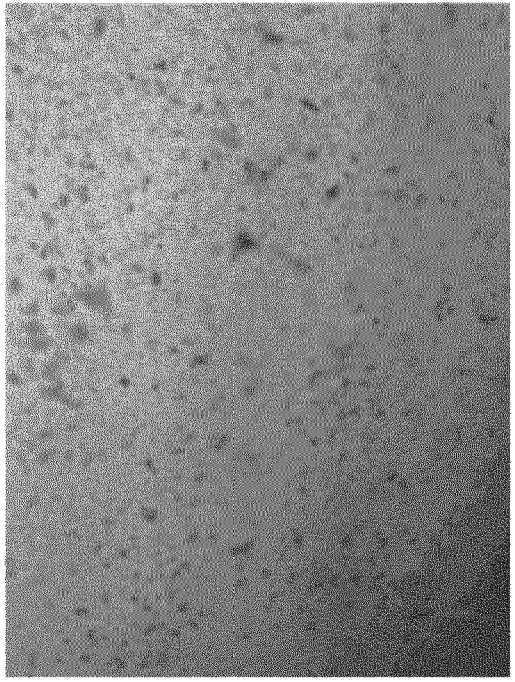
FIG. 27 shows brightfield images demonstrating that the method for generating Extra-hepatic Cholangiocyte Organoids described herein may also be used to derive Intrahepatic Cholangiocyte Organoids (ICOs) from whole liver, biopsy tissue or EPCAM sorted intrahepatic cholangiocytes. P0, P20: Passage 0, 20.
Figure 27:
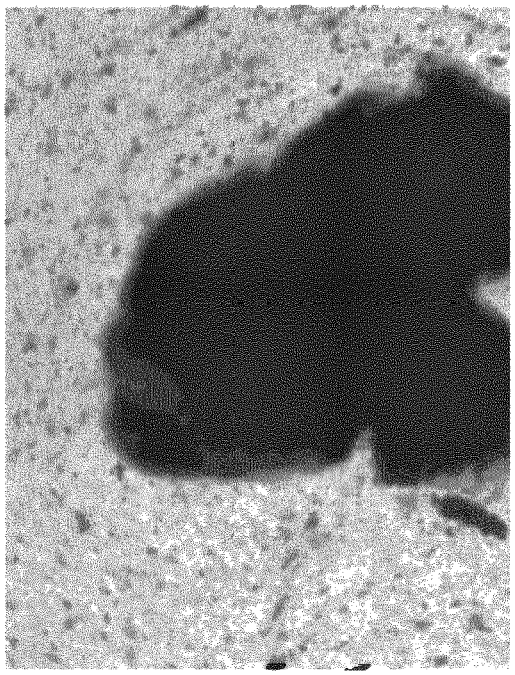
Figure 27:
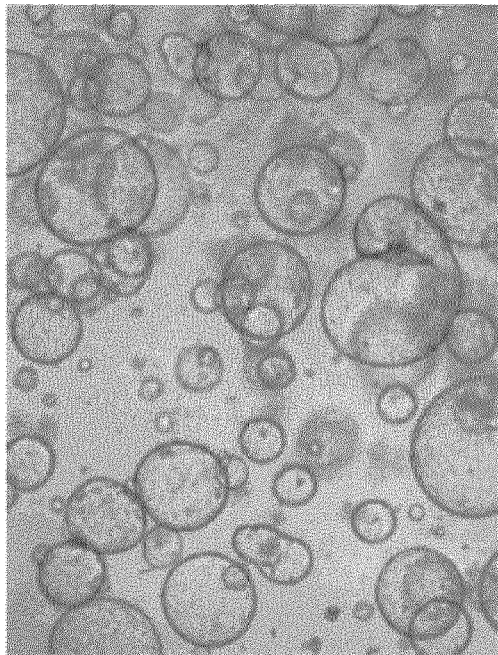

Under these conditions, we derived 8 different ECO lines from a variety of deceased donors aged from 33 to 77 years. Notably, we obtained similar results by using cholangiocytes isolated from the gallbladder or by harvesting common bile duct cholangiocytes using an Endoscopic Retrograde Cholangiopancreatography (ERCP) brush instead of scrapping the lumen (FIG. 7). Importantly, our system was also used for the derivation of intrahepatic COs (ICOs) from biopsy tissue or sorted cholangiocytes (FIG. 27). Consequently, COs can be derived from any area of the biliary tree (intra-hepatic, extra-hepatic or gallbladder) and harvested using peri-operative (dissection, scrapping or enzymatic dissociation using enzymes such as collagenase and liberase) or minimally invasive (ERCP brushings, liver biopsy) approaches.

2.2 ECOs Maintain Key Biliary Markers and Function in Culture

Figure 8:
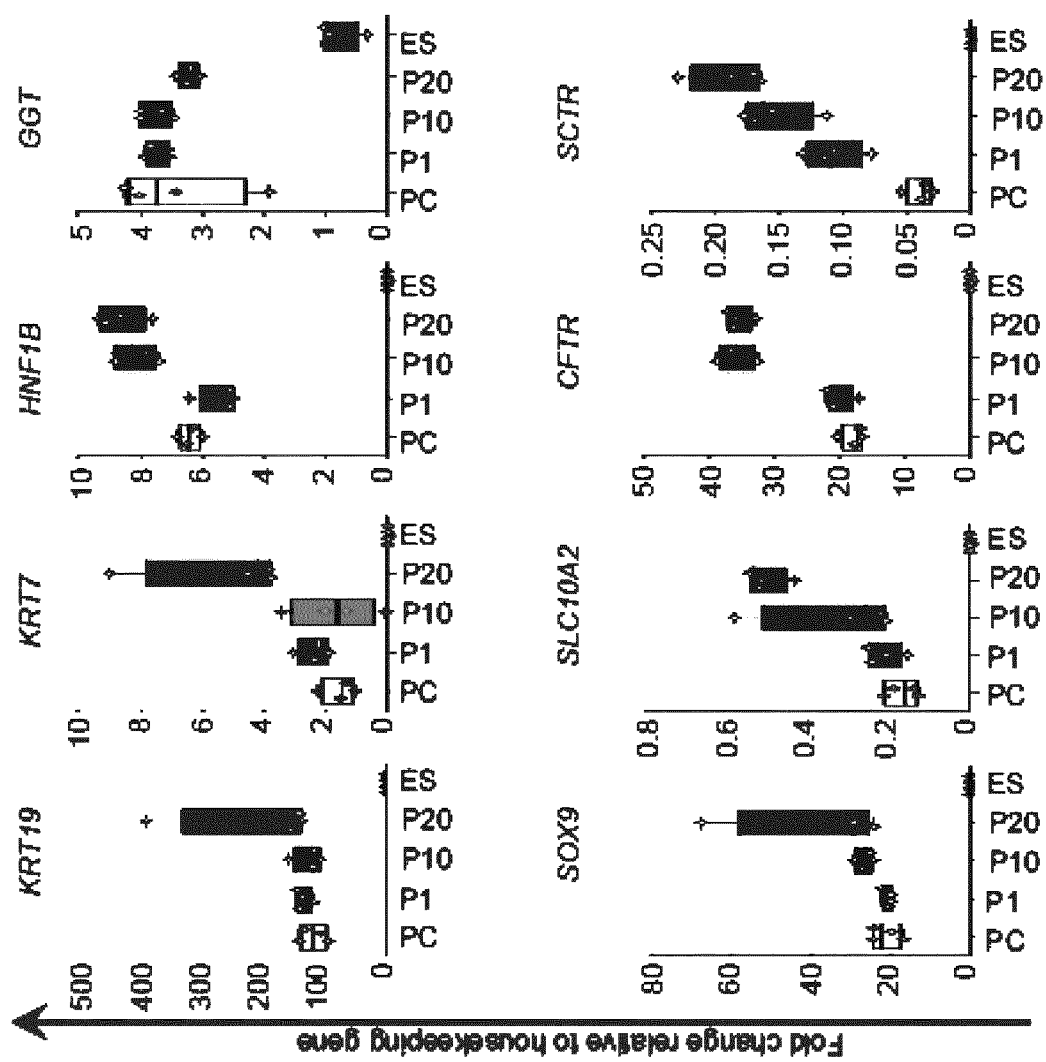
FIG. 8 shows the results of quantitative real time PCR (QPCR) of biliary markers in Passage 1 (P1), Passage 10 (P10) and Passage 20 (P20) ECOs compared to freshly isolated Primary Cholangiocytes (PC) and Embryonic Stem (ES) cells used as a negative control (n=4 ECO lines). Center line, median; box, interquartile range (IQR); whiskers, range (minimum to maximum). Values are relative to the housekeeping gene Hydroxymethylbilane Synthase (HMBS).

The resulting cells were expanded in vitro for prolonged periods of time (20 passages) while maintaining their genetic stability. Electron microscopy revealed the presence of characteristic ultrastructural features including cilia, microvilli and tight junctions, while QPCR and immunofluorescence (IF) analyses established the expression of key biliary markers such as Cytokeratin 7 (KRT7 or CK7), Cytokeratin 19 (KRT19 or CK19), Hepatocyte Nuclear Factor 1 beta (HNF1B), GGT, Secretin Receptor (SCTR), sodium-dependent bile acid transporter (ASBT/SLC10A2), Cystic fibrosis transmembrane conductance regulator (CFTR) and SRY-box 9 (SOX9) (Sampaziotis F. et al., Biotechnol. 2015 1-11) as shown in FIGS. 8 and 28. Importantly, our culture system allows only the expansion of cholangiocyte organoids. Other liver cell types such as hepatocytes are not propagated as illustrated by the downregulation of hepatic markers (see for example, FIG. 28).

Of note, stem cell markers such as POU5F1 or OCT4, NANOG, prominin 1 (PROM1), leucine rich repeat containing G protein-coupled receptor (LGR) LGR-4/5/6; markers of non-biliary lineages including albumin (ALB), α1-antitrypsin (SERPINA1 or A1AT), keratin 18 (KRT18), pancreatic and duodenal homeobox 1 (PDX1), insulin (INS) and glucagon (GCG); and EMT markers (vimentin (VIM), snail family transcriptional repressor 1 (SNAI1) and S100 calcium binding protein A4 (S100A4) were not detected. On the other hand, 98.1%±0.9% (standard deviation; n=3) of the cells co-expressed CK7 and CK19 following 20 passages thereby confirming the presence of a near homogeneous population of cholangiocytes.

Figure 9:
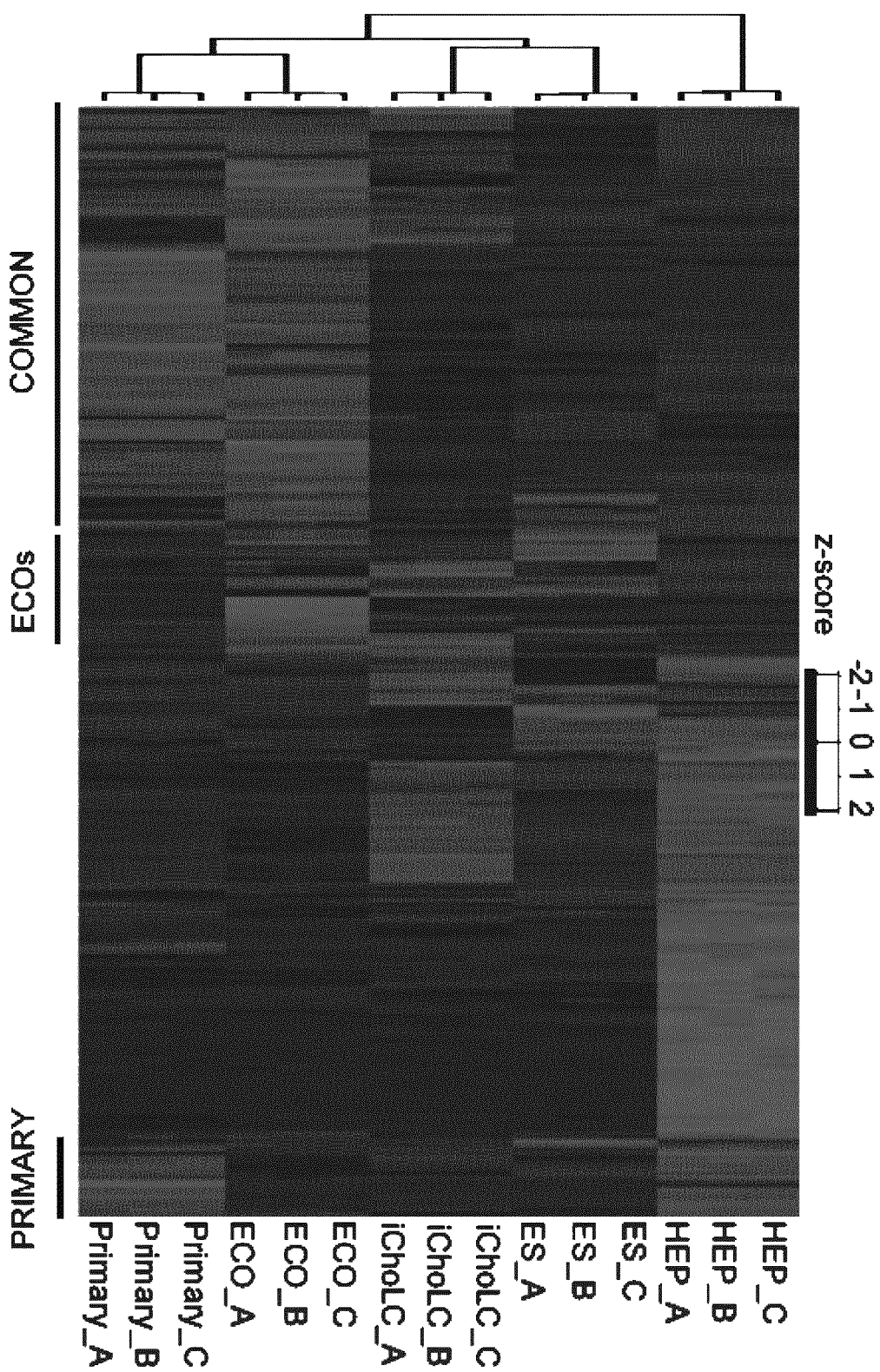
FIG. 9 depicts Euclidean hierarchical clustering analysis comparing the transcriptome of primary cholangiocytes (Primary), passage 20 ECOs (ECO), hIPSC-derived intrahepatic cholangiocyte-like-cells (iChoLC), ES cells (ES) and hepatocytes (HEP). For each probe, standard scores (z-scores) indicate the differential expression measured in number of standard deviations from the average level across all the samples. Clusters of genes expressed in ECOs, primary cholangiocytes or both cell types are indicated.
Figure 32:
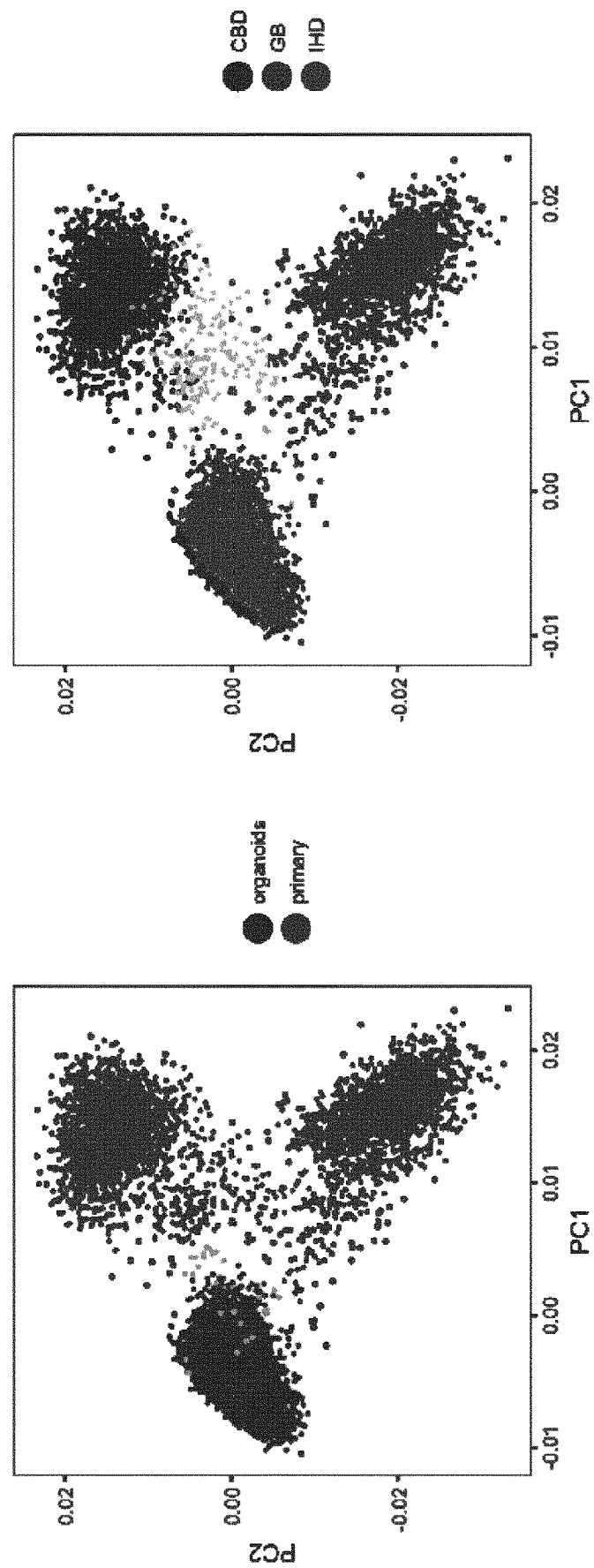
FIG. 32 shows single cell RNA sequencing characterization of COs which indicates that cholangiocytes organoids (ECOs and ICOs) differ from their tissue of origin for the expression of specific factors, including immune genes. PCA plots comparing cholangiocyte organoids from different regions of the biliary tree to primary cholangiocytes are shown. Left panel shows annotation based on cell type (organoids vs .primary). Right panel shows annotation based on region of origin CBD: Common bile duct, GB: Gallbladder, and IHD: Intrahepatic.
Figure 33:
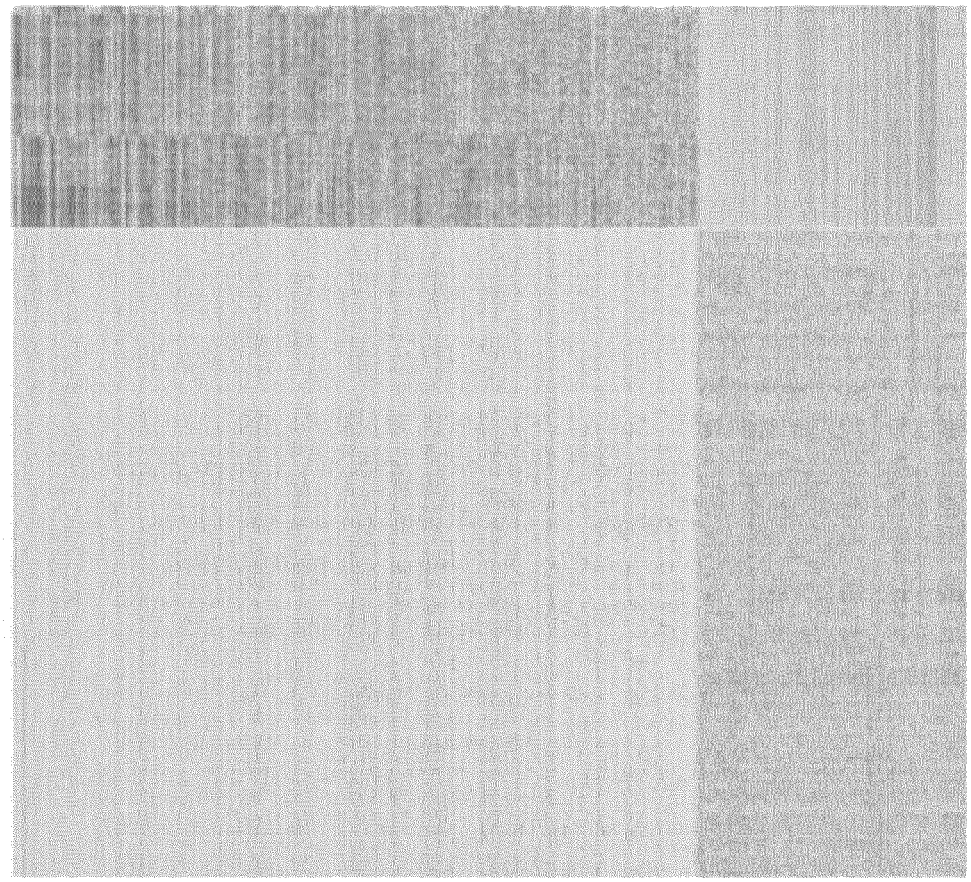
FIG. 33 shows a heat map demonstrating differences in gene expression between Cholangiocyte Organoids (COs) and primary cholangiocytes. Indicative genes are illustrated on the right.

Transcriptomic analyses (FIG. 9) revealed that ECOs maintain a stable gene expression profile over multiple passages (Pearson correlation coefficient for Passage 1 (P1) vs. Passage 20 (P20) r=0.99), express key biliary markers and cluster closely to freshly isolated cholangiocytes (Pearson correlation coefficient for Primary Cholangiocytes (PCs) vs. Passage 20 (P20) r=0.92). Gene ontology analyses confirmed enrichment of pathways characteristic for the biliary epithelium. This demonstrates that primary cholangiocytes derived from the extrahepatic biliary tree can be expanded in vitro without losing their original characteristics. Single cell RNA sequencing of cells from cholangiocyte organoids (COs) showed that the COs display a transcriptome signature that is distinct from primary cholangiocytes (FIGS. 32 and 33), in particular for the expression of markers such as the Major Histocompatibility Complex molecules and cell cycle genes.

Figure 10:
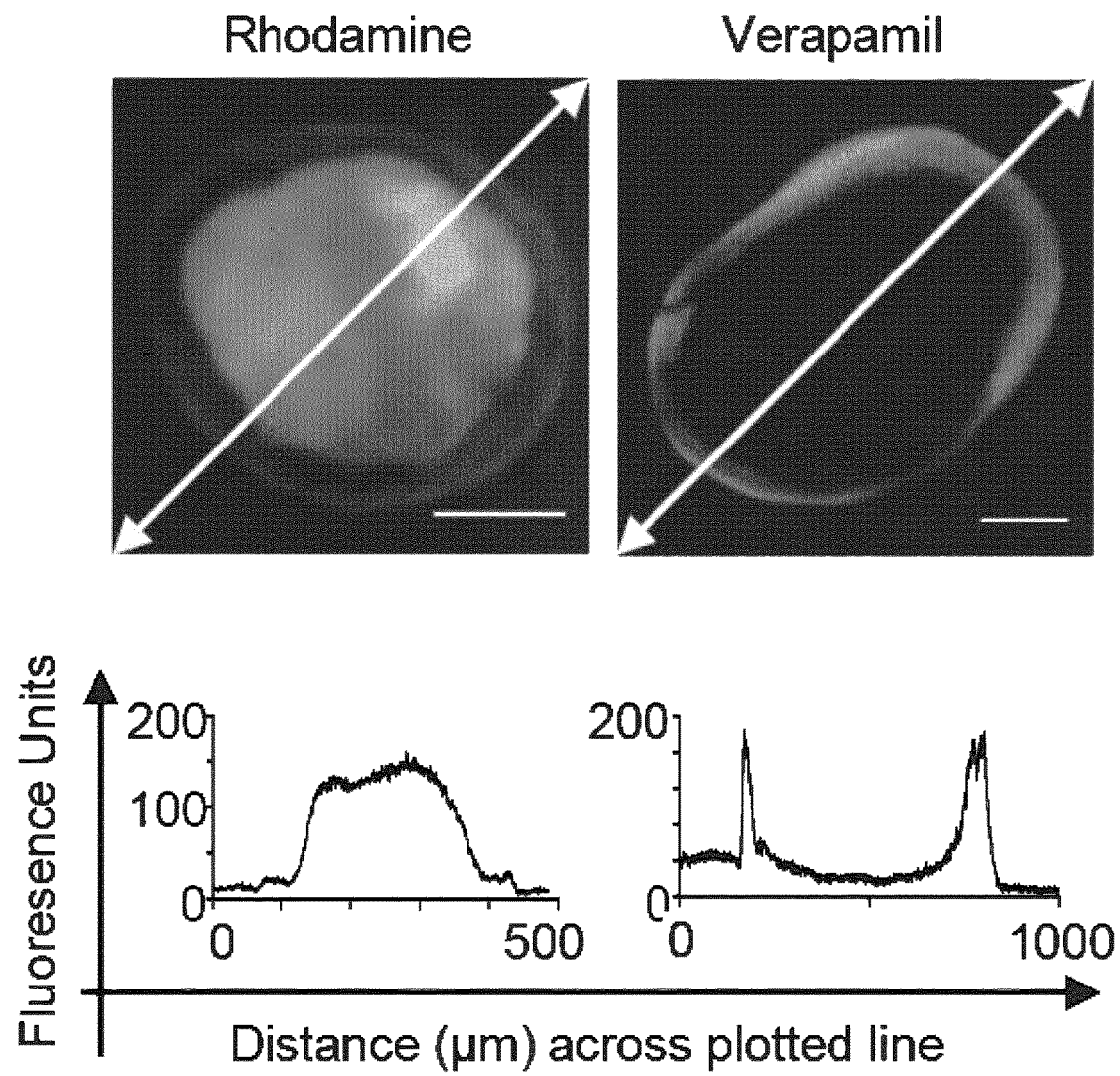
FIG. 10 shows secretion of the MDR1 fluorescent substrate rhodamine 123 in the lumen of ECOs, which is inhibited by the MDR1 inhibitor verapamil. Scale bars, 100 μm.
Figure 11:
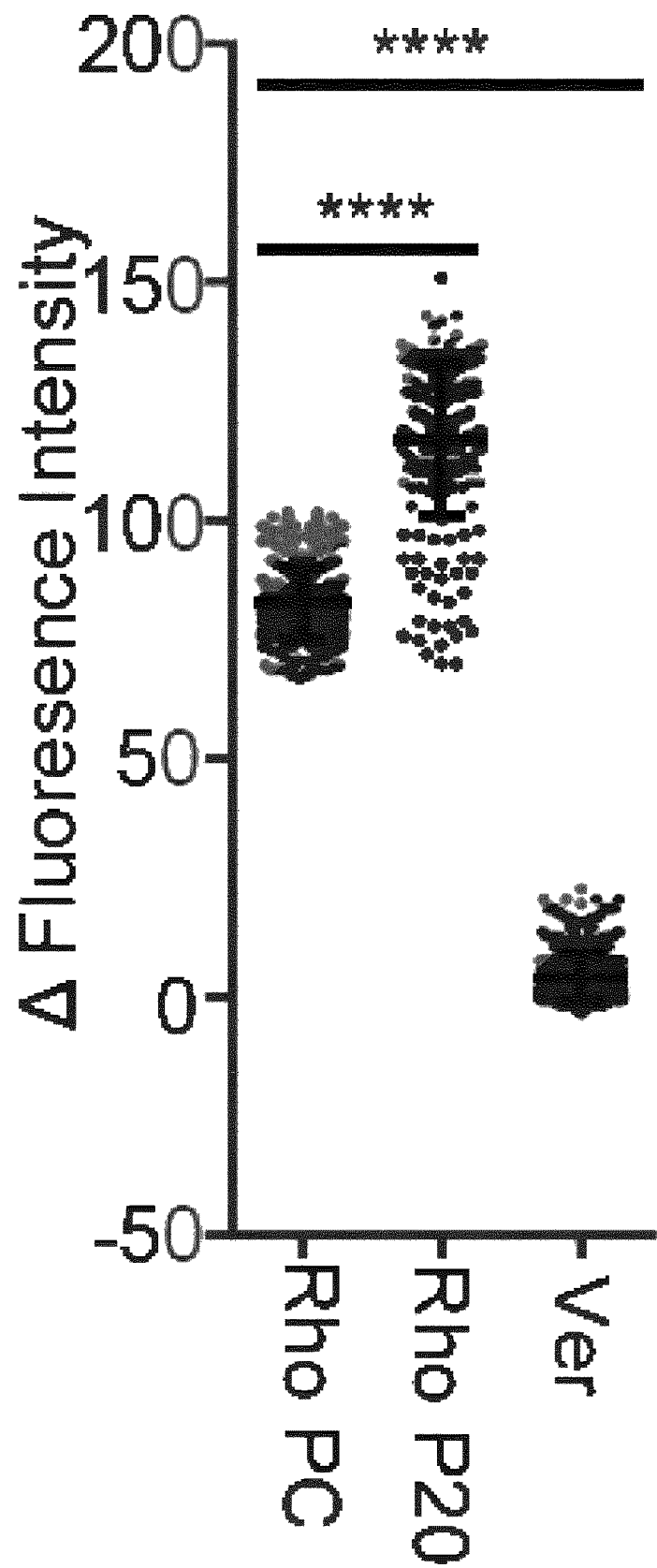
FIG. 11 shows mean intraluminal rhodamine 123 fluorescence intensity normalized to background in freshly plated Primary Cholangiocytes (Rho PC), Passage 20 ECOs (Rho P20) and P20 ECOs treated with verapamil (Ver). Error bars show standard deviation; n=1565 measurements in total. ****P<0.001, Kruskal-Wallis test with Dunn's correction for multiple comparisons
Figure 12:
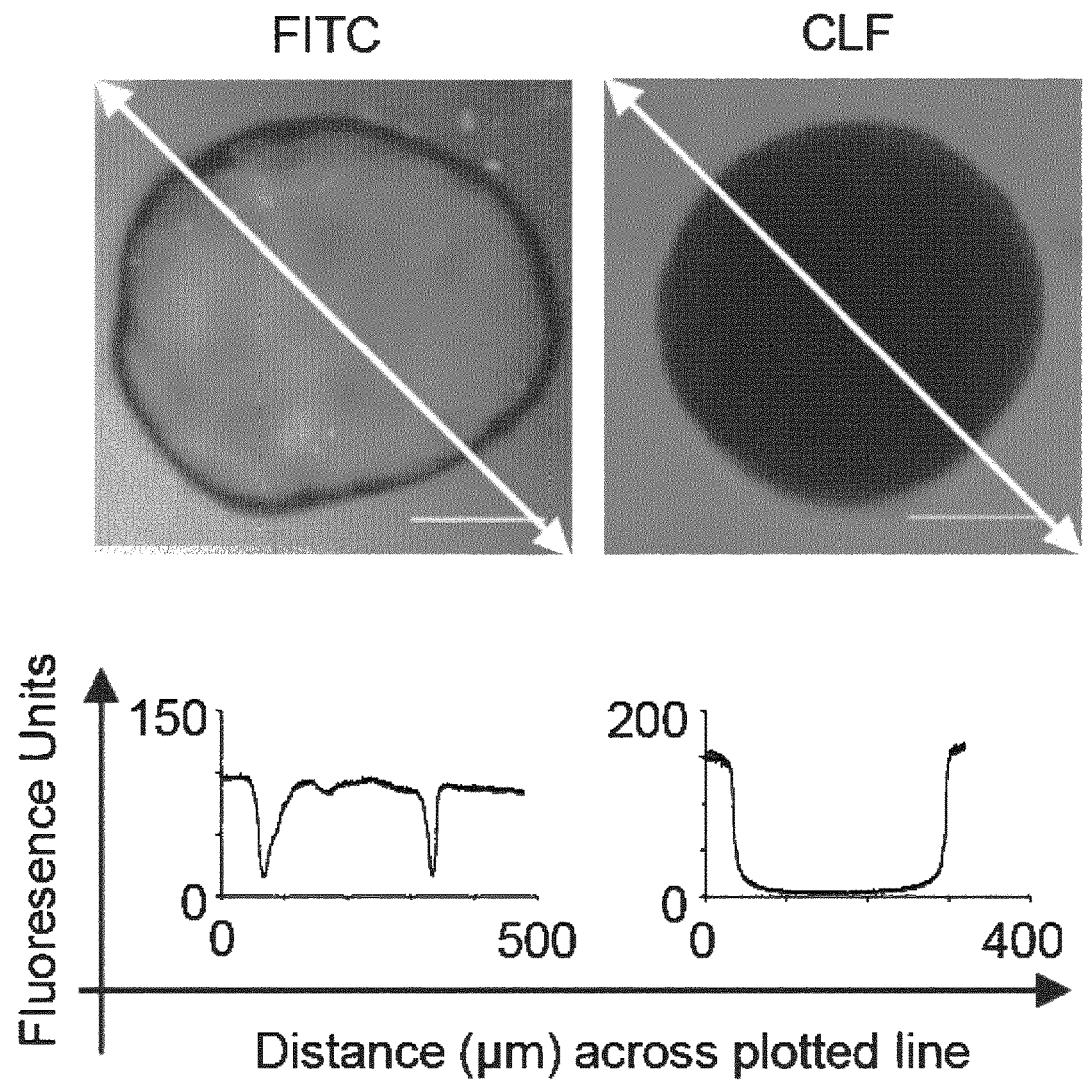
FIG. 12 shows luminal extrusion of the fluorescent bile acid Cholyl-Lysyl-Fluorescein (CLF) compared to controls loaded with Fluorescein Isothiocyanate (FITC), confirming bile acid transfer. Scale bars, 100 μm.
Figure 13:
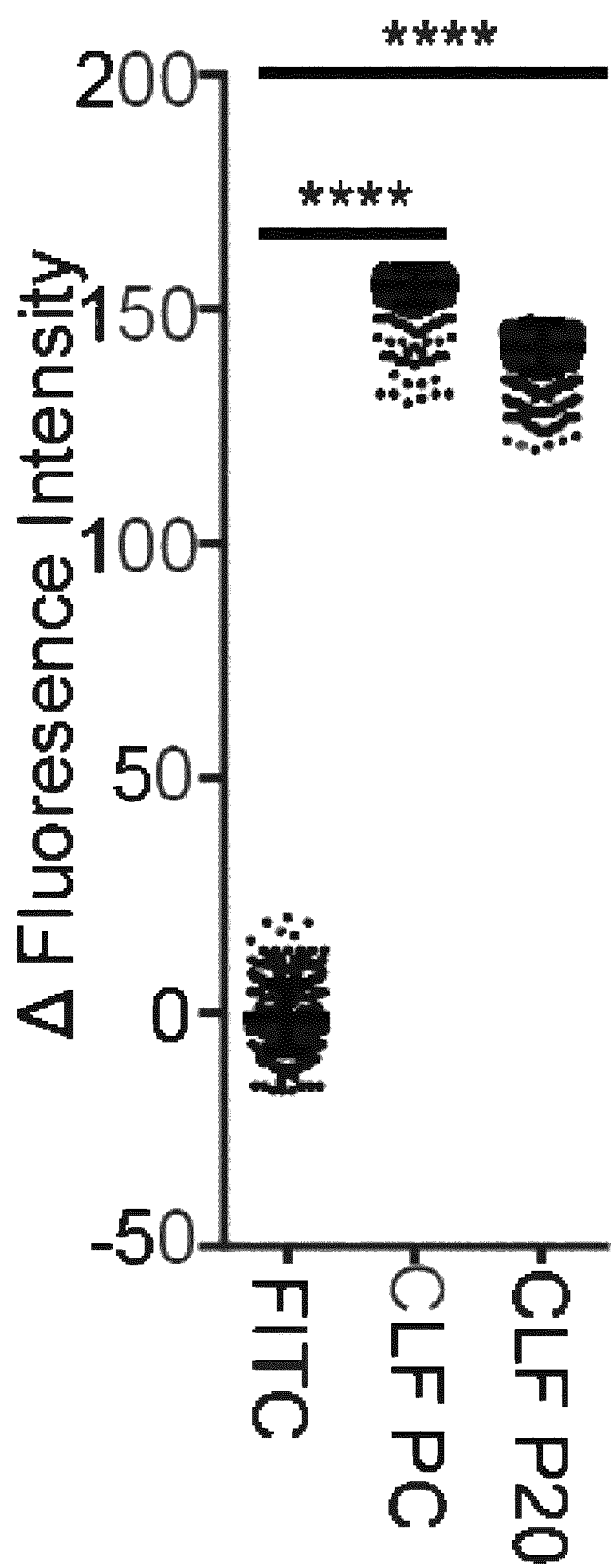
FIG. 13 shows mean intra-luminal fluorescence intensity normalized over background in freshly plated primary cholangiocytes loaded with FITC (FITC), freshly plated primary cholangiocytes loaded with CLF (CLF PC), and Passage 20 ECOs loaded with CLF (CLF PC20). n=1947 total measurements. Error bars show standard deviation; ****P<0.001, Kruskal-Wallis test with Dunn's correction for multiple comparisons.
Figure 14:
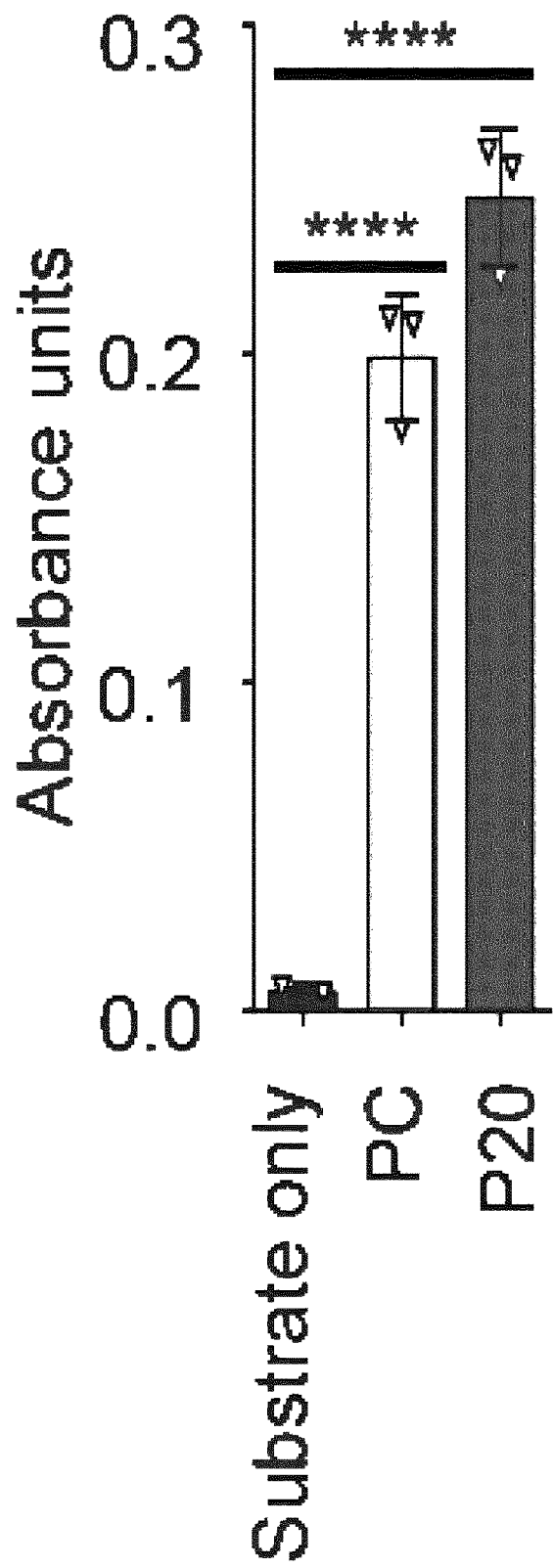
FIG. 14 shows mean Gamma Glutamyl-Transferase (GGT) activity of P20 ECOs and freshly plates PCs; Error bars show standard deviation; n=3; ****P<0.001, one-way ANOVA with Dunnett's correction for multiple comparisons.
Figure 15:
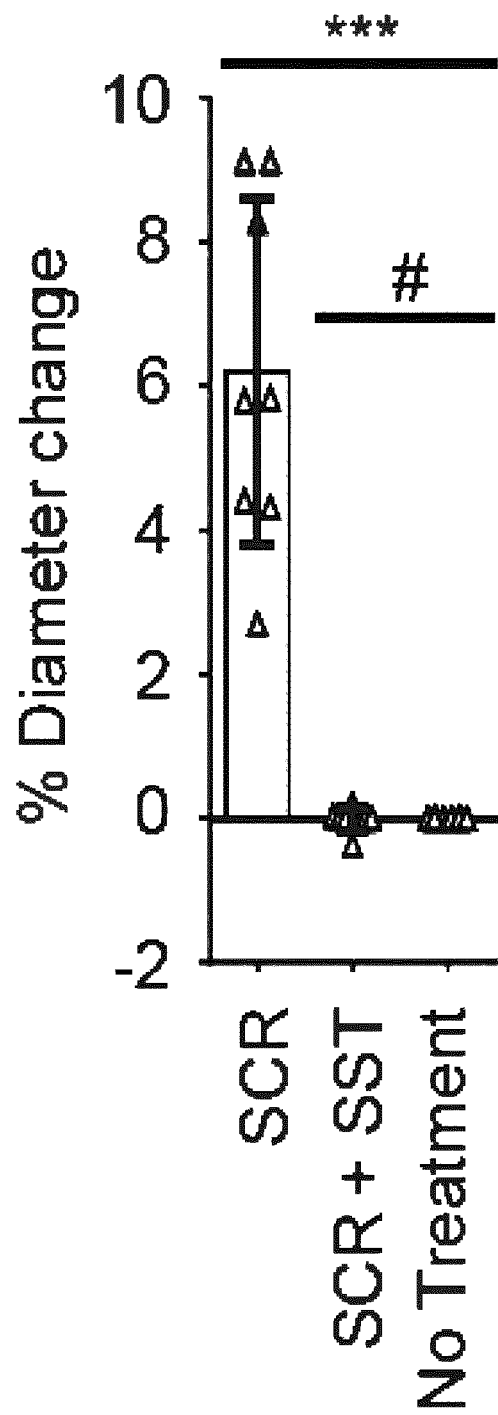
FIG. 15 shows mean diameter measurements of ECOs treated with secretin or secretin and somatostatin, n=8. Error bars show standard deviation; ***P<0.001; #P>0.05 (Kruskal-Wallis test with Dunn's correction for multiple comparisons).
Figure 29:
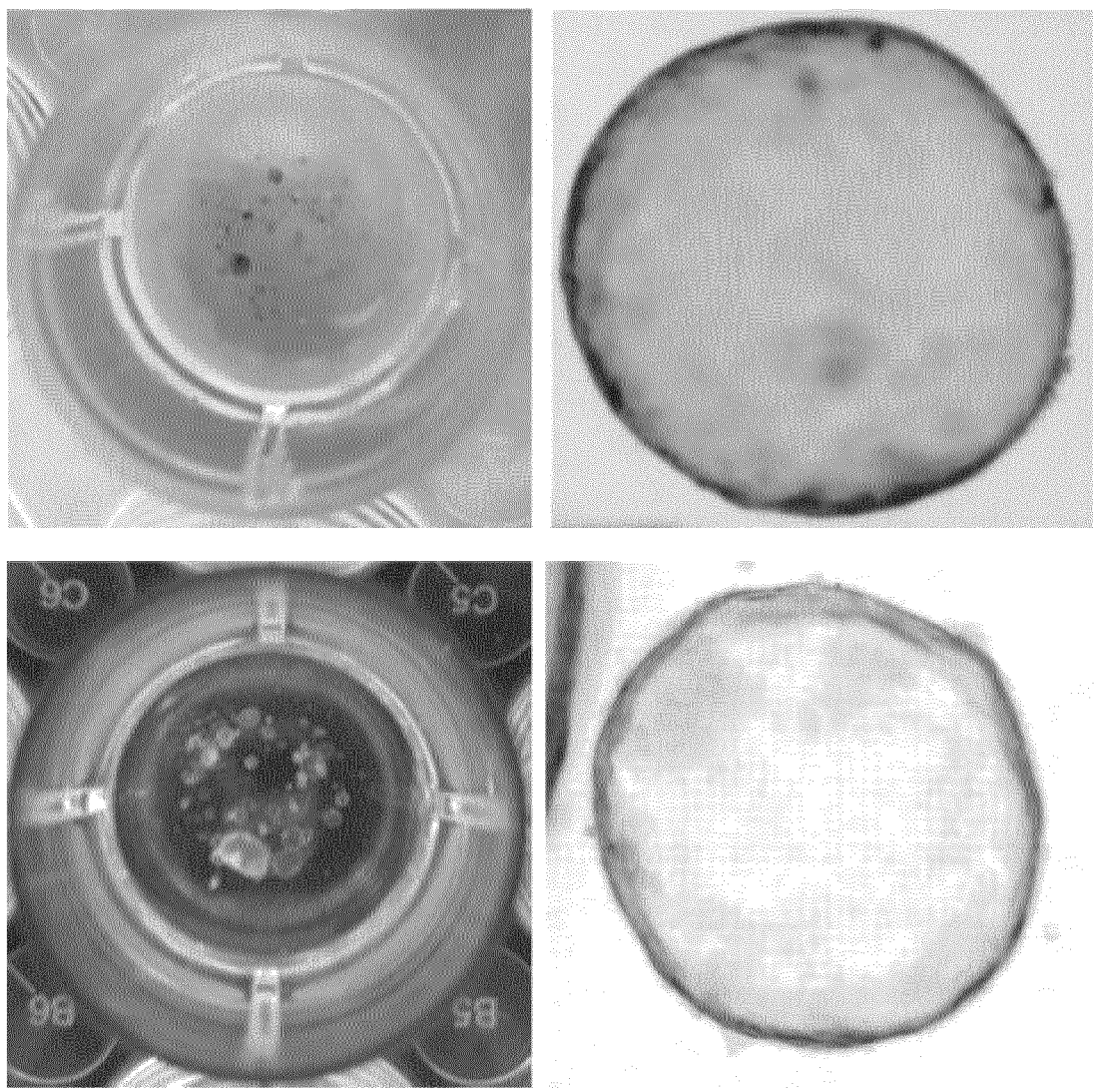
FIG. 29 shows that ICOs are functional since they display alkaline phosphatase (ALP) activity.
Figure 30:
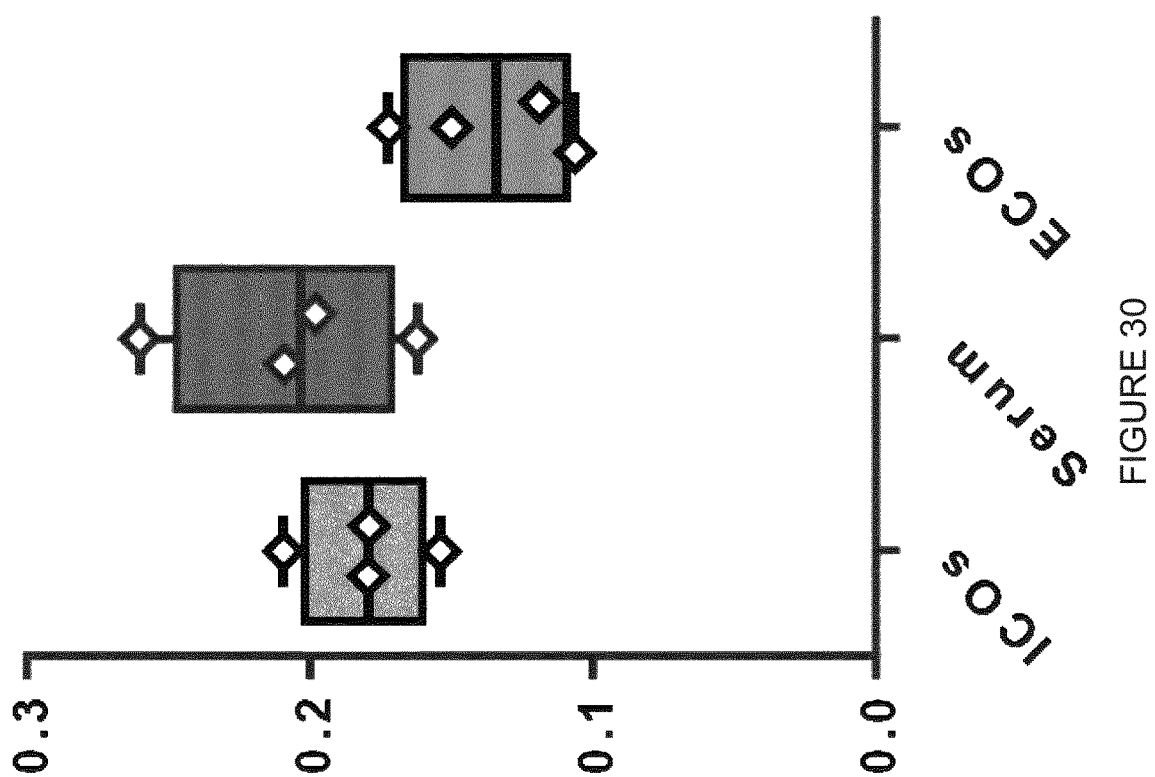
FIG. 30 shows that ICOs are functional since they display y-glutamyltransferase (GGT) activity.
Figure 31:
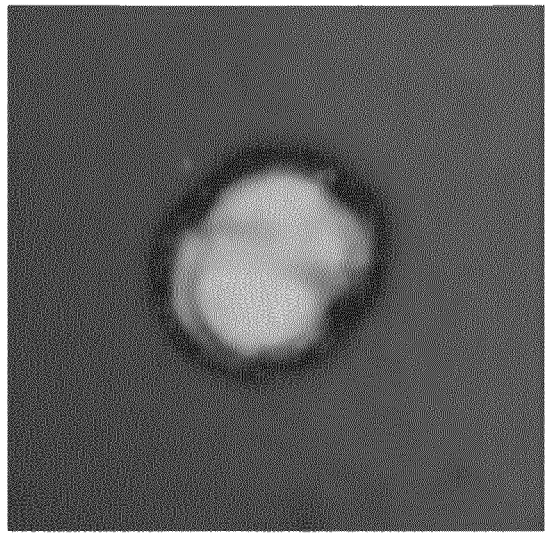
FIG. 31 demonstrate that ICOs are functional since they can transport drug as shown by the luminal accumulation of Rhodamine 123 by ICOs (top left) which is inhibited in the presence of verapamil (bottom left) and the luminal excretion of the fluorescent bile acid CLF (bottom right).
Figure 31:
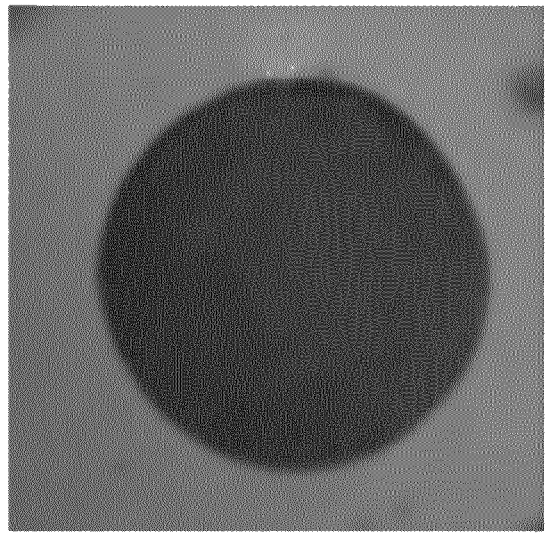
Figure 31:
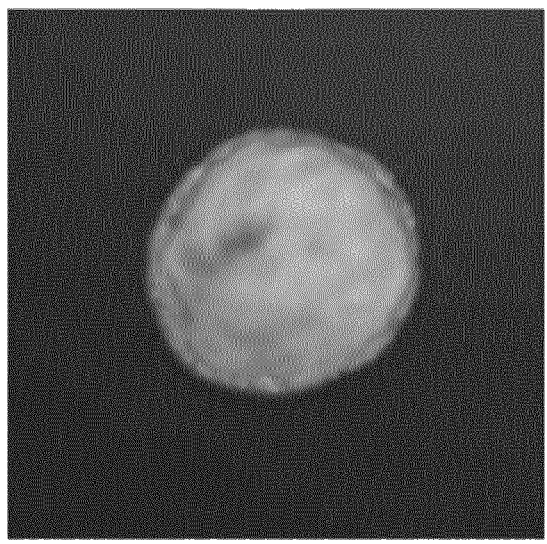
Figure 31:
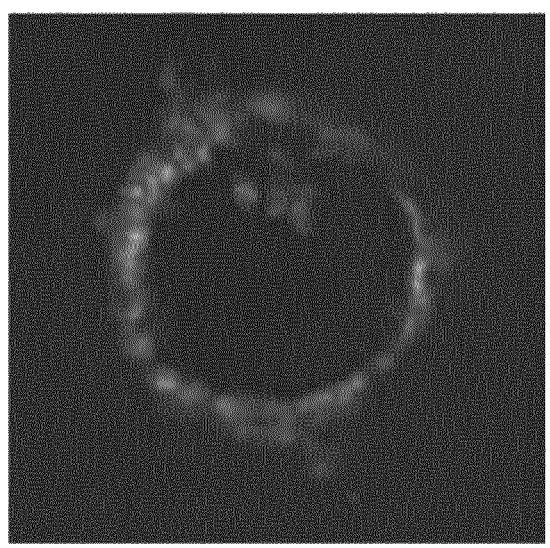

We then further characterized ECOs by focusing on their function following long-term culture (20 passages). The biliary epithelium regulates the homeostasis of bile through the transport of ions, water and bile acids. The secretory capacity of ECOs was interrogated using Rhodamine-123, a fluorescent substrate for the cholangiocyte surface glycoprotein Multidrug Resistance protein-1 (MDR1) (FIGS. 10 and 11). Rhodamine-123 accumulated in the ECO lumen only in the absence of the MDR-1 antagonist verapamil, thereby confirming active secretion through MDR-1. Luminal extrusion of bile acids was also demonstrated by showing that the fluorescent bile acid Cholyl-Lysyl-Fluorescein (CLF) was actively exported from ECOs (FIGS. 12, 13, and 31). Furthermore, ECO ALP and GGT activity was comparable to freshly plated primary cholangiocytes (FIGS. 14, 29 and 30). The response of ECOs to secretin and somatostatin was also assessed. Secretin promotes water secretion, distending the bile duct lumen, while somatostatin negates the effects of secretin. Accordingly, organoids exposed to secretin increased their diameter compared to untreated controls, while somatostatin inhibited the effect of secretin (FIG. 15).

Our data, therefore, demonstrate that ECOs maintain their functional properties even after long term culture.

2.3 ECO-Populated Scaffolds Reconstruct the Gallbladder Wall

Figure 16:
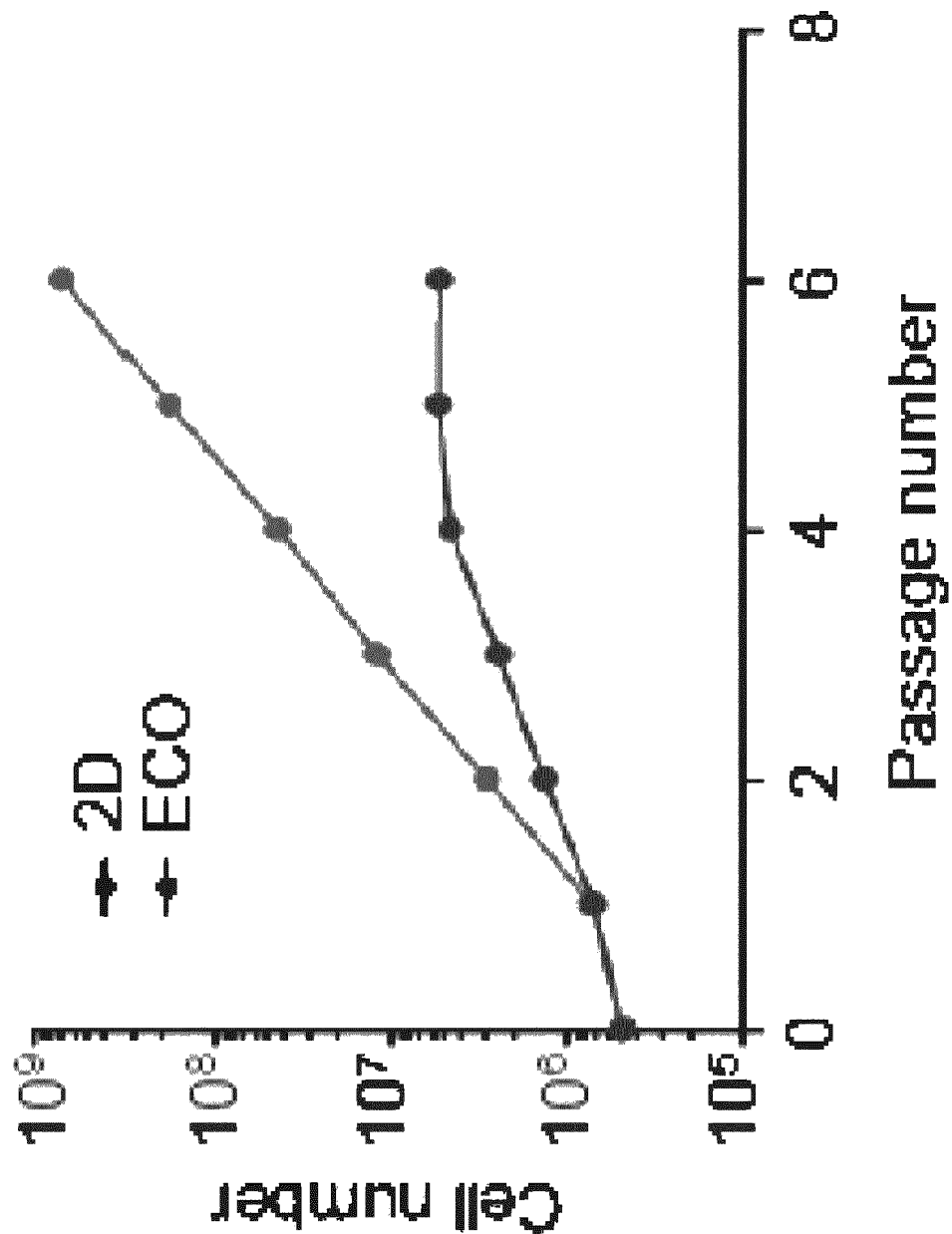
FIG. 16 shows growth curves of primary cholangiocytes plated as monolayer (2D) compared to primary cholangiocytes grown as ECOs (ECO), demonstrating that 2D cholangiocytes stop proliferating after a few passages. Starting from the same number of cells ($5 \times 10^5$), 2D cholangiocytes fail to provide the number of cells required to seed a PGA scaffold ($10^7$ cells).
Figure 17:
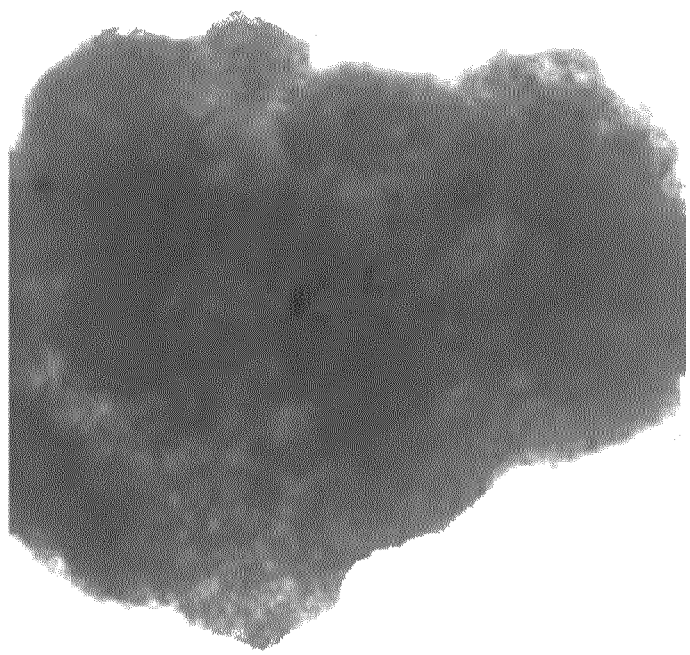
FIG. 17 shows brightfield images demonstrating that 2D cholangiocytes fail to expand and populate PGA scaffolds and remain limited to the site of injection. A brightfield image of a scaffold populated by ECOs dissociated to single cells (ECO-SC) is provided as a positive control. The scaffold was seeded with same number of cells and cultured for the same period of time as the 2D cholangiocyte scaffold. Scale bars: 100 μm.
Figure 17:
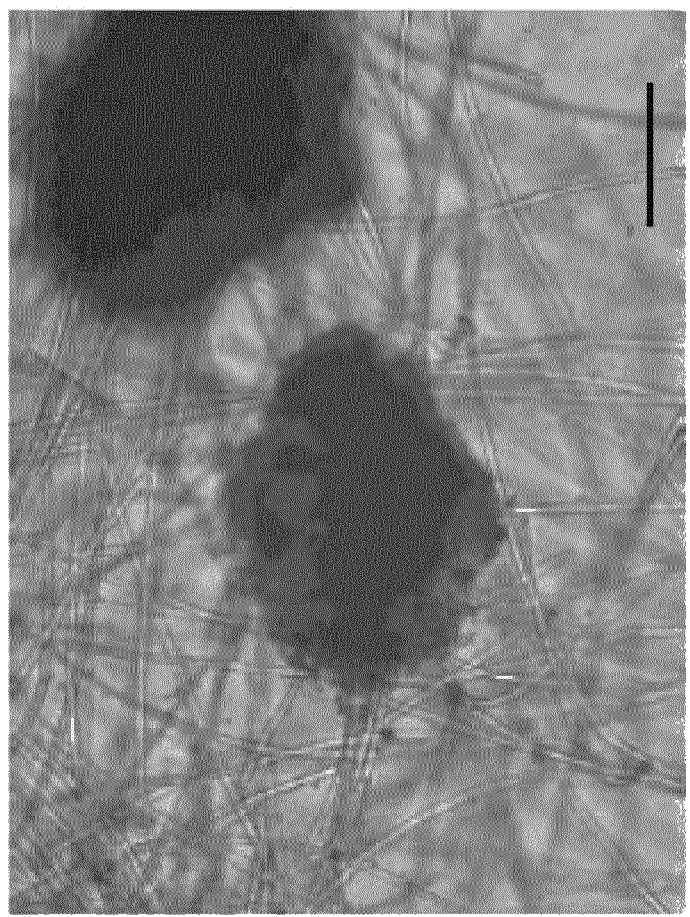

To assess the potential of ECOs for tissue engineering, we interrogated their capacity for populating polyglycolic acid (PGA) biodegradable scaffolds commonly used to provide the structural and mechanical support required for tissue reconstruction. Indeed, PGA is one of the most widely used synthetic polymers since it does not induce inflammatory responses in the surrounding tissue; it is biodegradable; and it is more flexible and easier to process compared to natural polymers such as collagen. To facilitate tracking of the cells, ECOs expressing Green Fluorescent Protein (GFP) were generated through viral transduction. The resulting cells were seeded on PGA scaffolds, attached to the PGA fibres after 24-48 hours and continued to grow for 4 weeks until the scaffold was confluent. Of note, primary cholangiocytes grown in 2D conditions demonstrated limited expansion potential (FIG. 16) and failed to reach confluency when seeded on the scaffolds (FIG. 17), suggesting that the proliferative capacity of ECOs is crucial for successful scaffold colonization. The populated PGA scaffolds were easily handled with forceps and divided into smaller pieces with a surgical blade. The cells populating the scaffolds retained expression of biliary markers such as CK7 and CK19, demonstrated no evidence of epithelial-mesenchymal transition (EMT) markers CK19 and VIM and maintained their functional properties including ALP and GGT activity. Therefore, ECOs can populate PGA scaffolds while maintaining their functionality and marker expression thereby providing a bioengineered tissue resembling the biliary epithelium.

Figure 18:
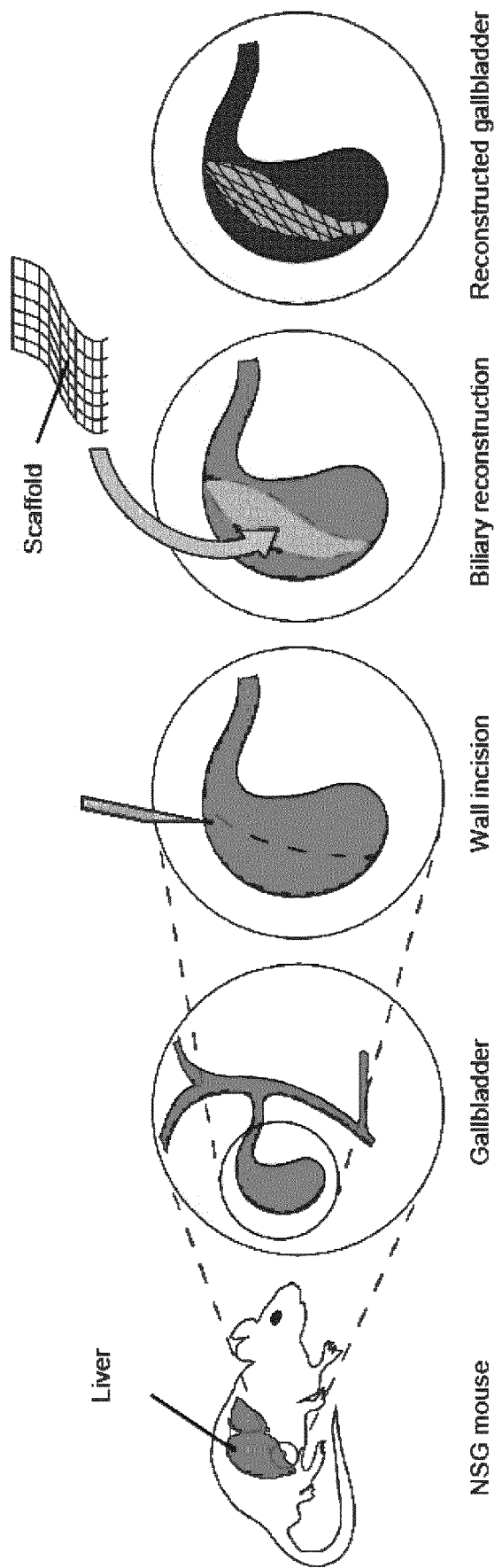
FIG. 18 shows a schematic representation of the method used for biliary reconstruction in an extrahepatic biliary injury (EHBI) mouse model using ECOs.
Figure 19:
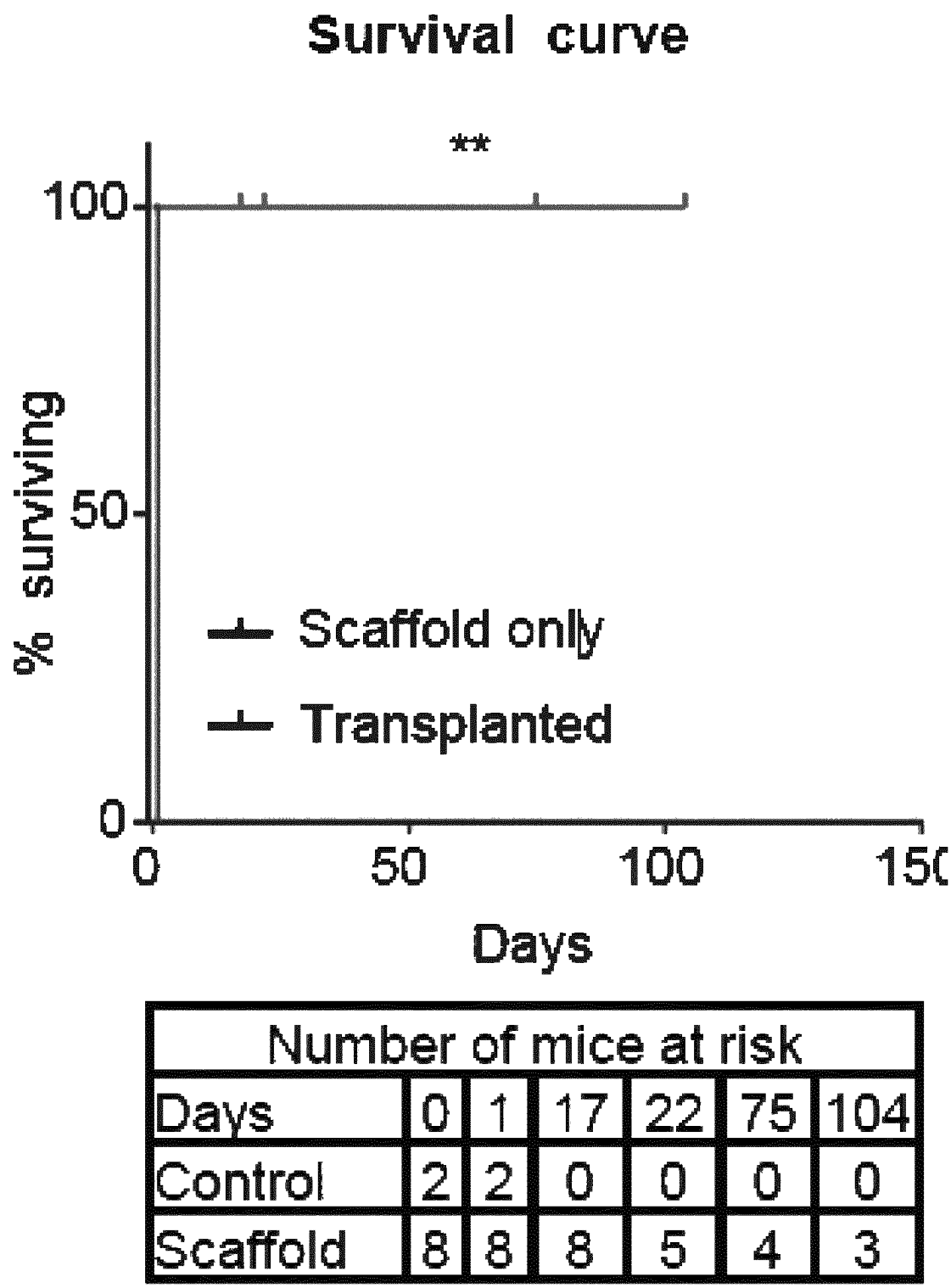
FIG. 19 shows a Kaplan-Meier survival analysis following biliary reconstruction in the EHBI mouse model using ECOs, demonstrating rescue of EHBI mice following biliary reconstruction with ECO-populated scaffolds (Transplanted) but not with acellular scaffolds (Scaffold only). **P<0.01 (log-rank test).
Figure 20:
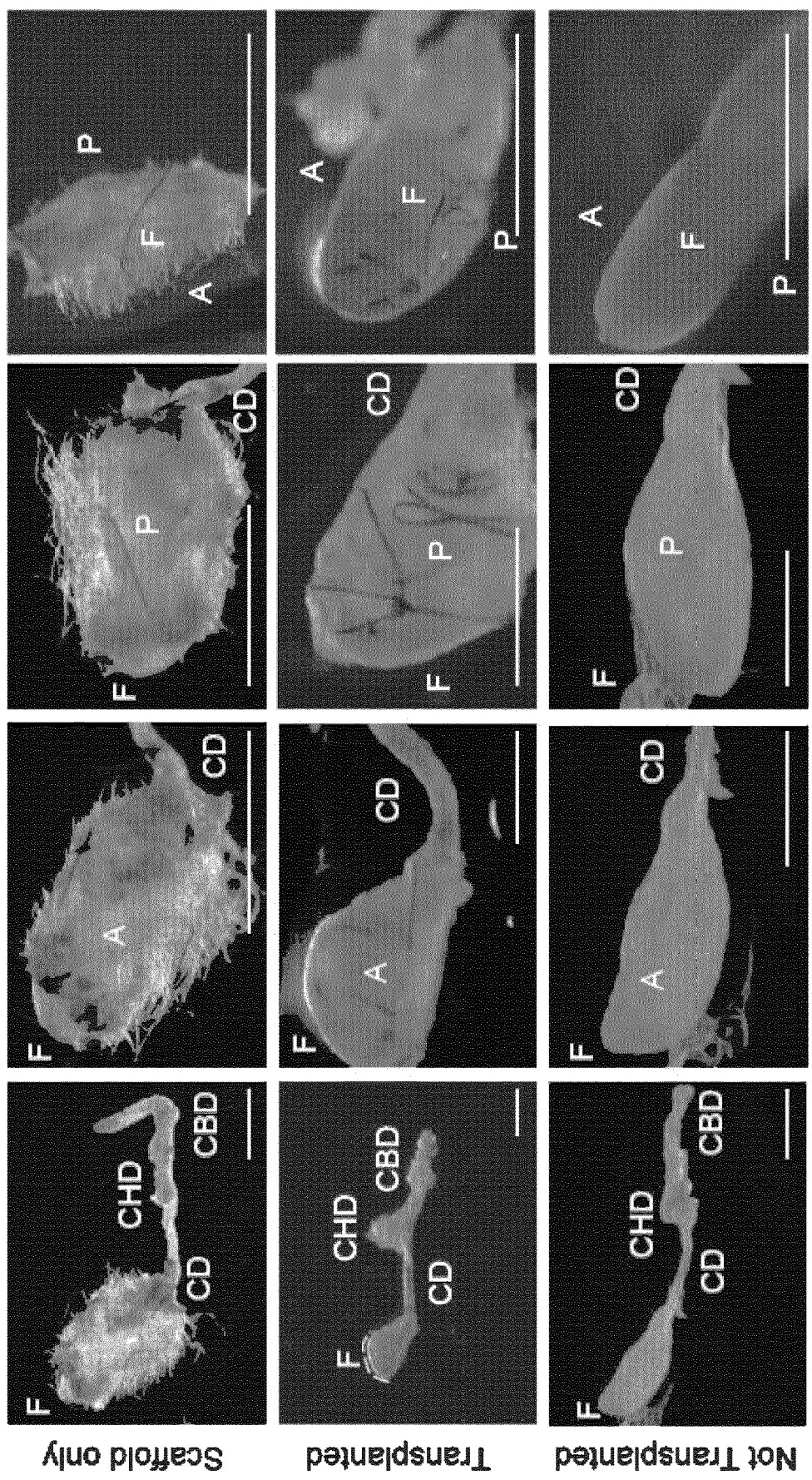
FIG. 20 shows gallbladders reconstructed with acellular PGA scaffolds (scaffold only), PGA scaffolds populated with ECOs (transplanted) and native un-reconstructed gallbladder controls (not transplanted), demonstrating full reconstruction with ECO populated scaffolds. CD: cystic duct, CBD: common bile duct, CHD: common hepatic duct, F: fundus, A: anterior surface, P: posterior surface. Scale bars, 500 μm.

We then decided to define the capacity of ECOs to repair the biliary epithelium in a mouse model of extrahepatic biliary injury (EHBI). To simulate biliary tree wall defects requiring biliary reconstruction, the biliary tree of healthy NSG mice was compromised through a longitudinal incision in the gallbladder wall (FIG. 18). The surgical defect in the gallbladder wall was subsequently repaired by transplanting PGA scaffolds populated with GFP-ECOs into the injured animals. Acellular PGA scaffolds and scaffolds populated with GFP-expressing fibroblasts were used as a negative controls. Animals receiving acellular scaffolds died within 24 hours of the operation (FIG. 19) and post-mortem examination revealed yellow pigmentation of the peritoneal cavity and seminal vesicles consistent with bile leak; while all animals in the fibroblast-scaffold group failed to reconstruct their gallbladder which was replaced by fibrotic tissue incompatible with bile transport or storage. In contrast, animals transplanted with scaffolds containing ECOs survived for up to 104 days without complications and were culled electively. Notably, the reconstructed gallbladders in the ECO group were fully remodelled resembling the morphology of their native counterparts (FIG. 20). Histology, IF and QPCR analyses of the ECO-reconstructed gallbladders unveiled integration of GFP-positive ECOs expressing biliary markers, such as KRT19, KRT7, HNF1B, SOX9, CFTR and a human-specific epitope for Ku80. Of note, these IF analyses also showed the presence of mouse mesenchymal cells expressing vimentin and endothelial cells expressing CD31 in the reconstructed biliary epithelium, indicating that the scaffold is colonized by endogenous cells after transplantation.

Figure 21:
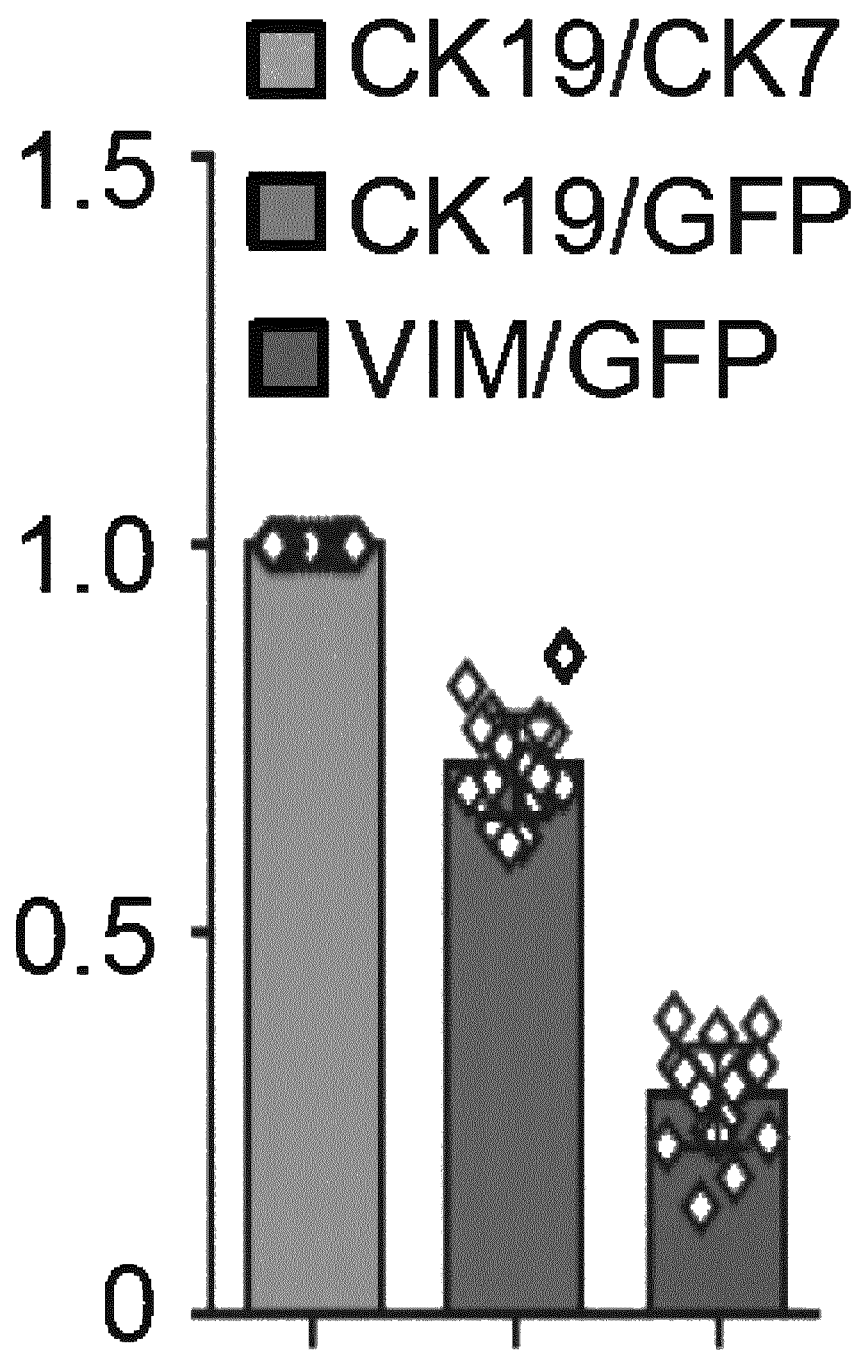
FIG. 21 shows the ratio of CK19+/CK7+, CK19+/GFP+ and VIM/GFP+ cells quantified in randomly selected sections of transplanted ECO-populated scaffolds; n=18. Error bars represent standard deviation.

Furthermore, we also identified a population of GFP+/vimentin+/CK19– cells, suggesting that ECOs also contributes to the scaffold stroma in vivo; possibly through EMT (FIG. 21).

The integrity of the reconstructed gallbladder lumen and its exposure to bile through continuity with the biliary tree were demonstrated using magnetic resonance cholangiopancreatography (MRCP) imaging prior to removal of the organ and was further confirmed with FITC cholangiograms. Post mortem surgical examination and full body magnetic resonance imaging 104 days post transplantation revealed no evidence of tumor formation while IF analyses revealed no GFP+ cells in the adjacent liver tissue. On the contrary, gallbladders reconstituted with fibroblast controls exhibited obliteration of the gallbladder lumen and replacement of the lumen and biliary epithelium by fibroblasts expressing Fibroblast Specific Antigen S100A4. Considered collectively, this demonstrates the capacity of ECOs to colonize their physiological niche and regenerate part of the biliary tree without any complications.

2.4 Bioengineered Bile Ducts Replace the Native Mouse Bile Duct

Figure 22:
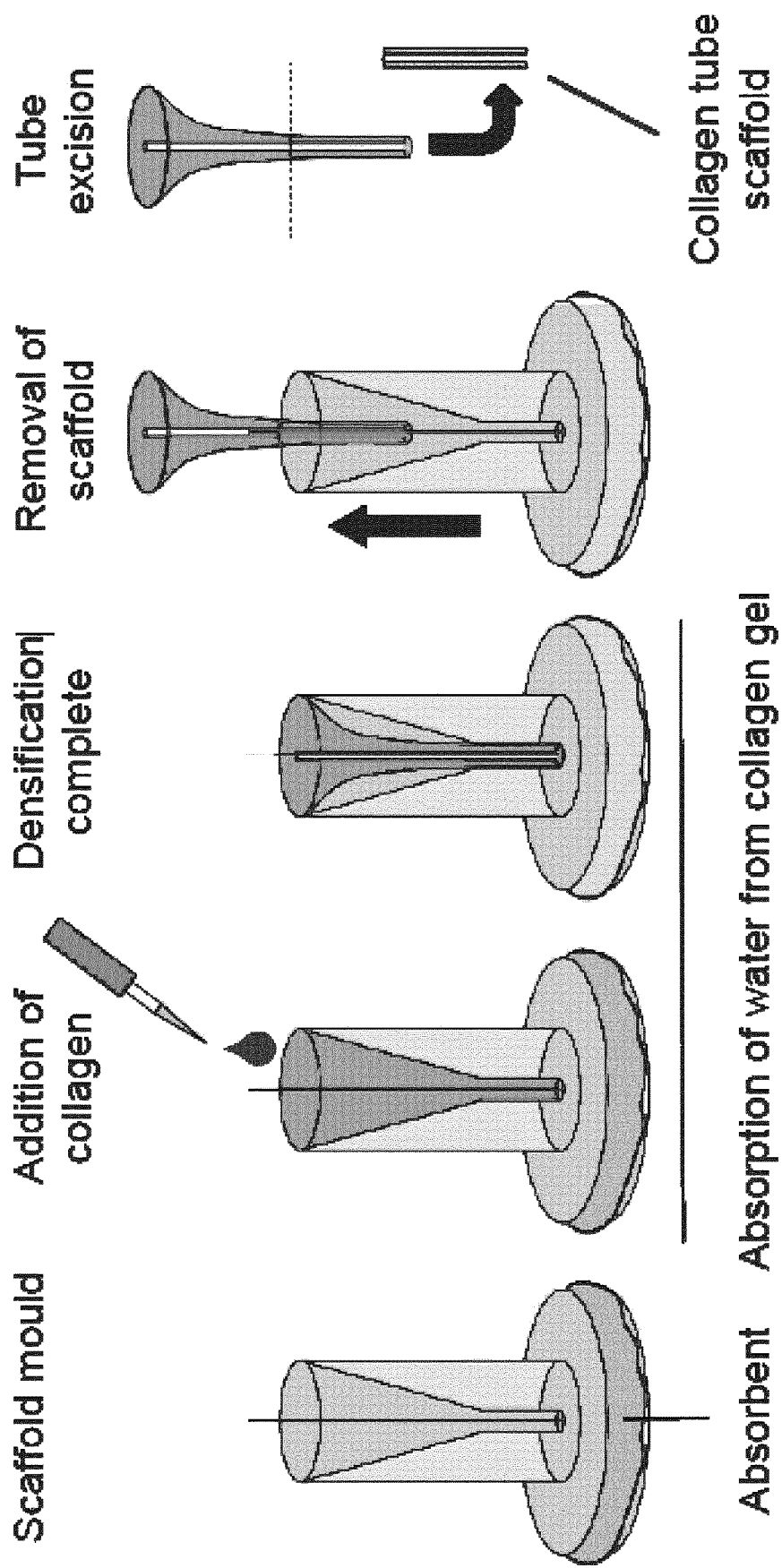
FIG. 22 shows a schematic representation of the method used for the generation of densified collagen tubular scaffolds for ECO population.
Figure 23:
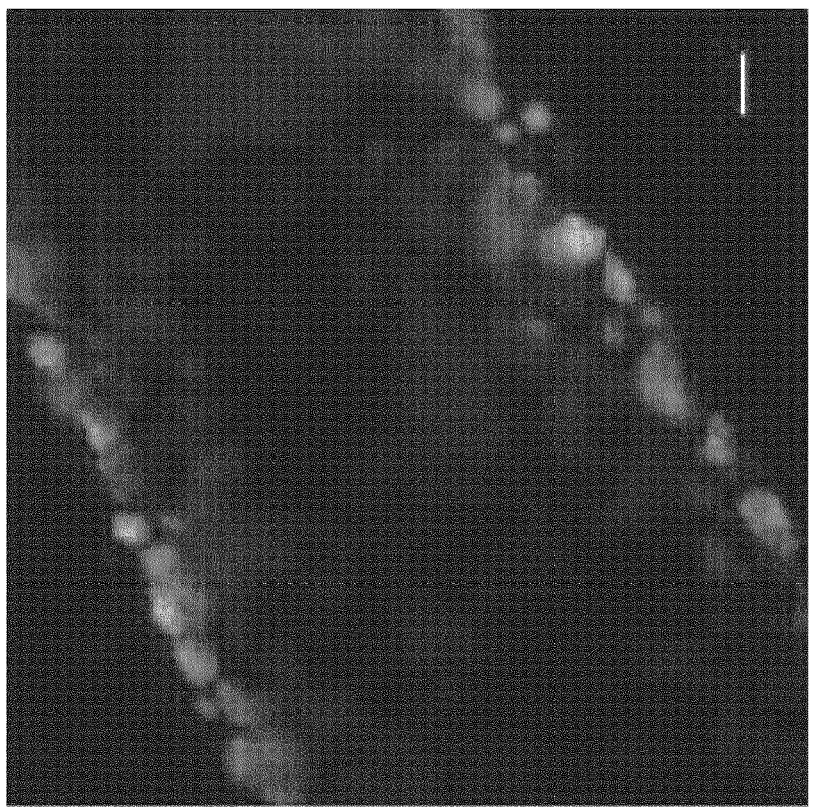
FIG. 23 shows a maximum intensity projection image of GFP+ ECO-populated tube after its generation (left), and confocal microscopy demonstrating lumen patency of an ECO-populated collagen tube (right). Scale bar, 30 μm.
Figure 23:
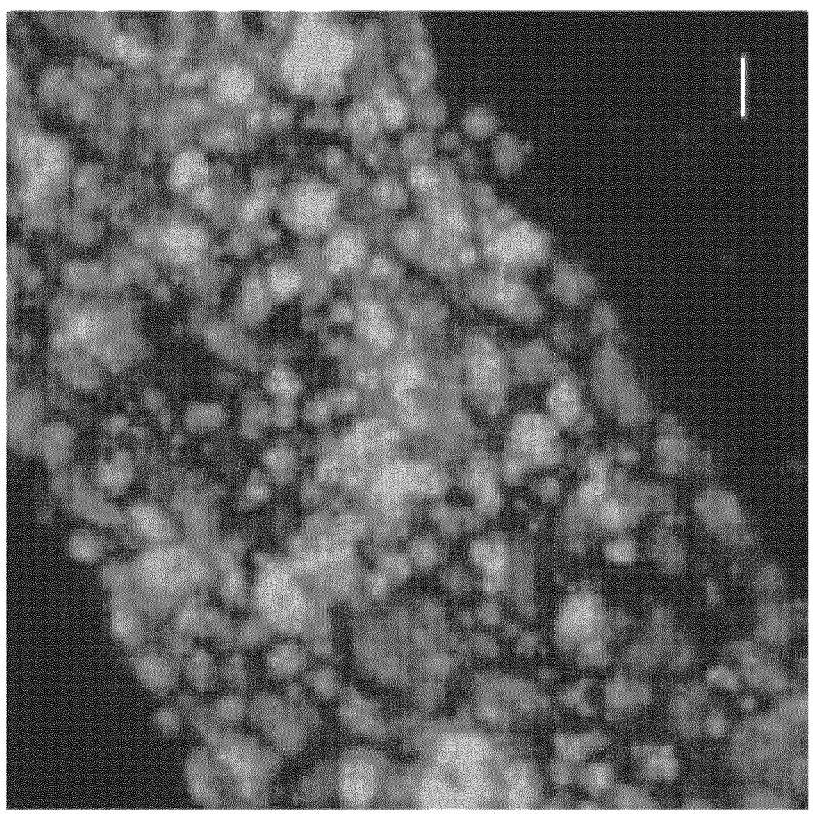

Reconstruction of the gallbladder wall provided proof-of-principle for the capacity of ECOs to repair the biliary epithelium after injury; however, the majority of extrahepatic bile duct disorders affect the common bile duct (CBD). Therefore, we focused on the generation of a tubular ECO-populated scaffold, which could be used for bile duct replacement surgery. The internal diameter of the mouse CBD is approximately 100 μm with a wall thickness of less than 50 μm, which precluded the use of a PGA scaffold due to mechanical properties. Instead, we generated densified collagen tubular scaffolds (FIG. 22) which were populated with GFP-expressing ECOs (FIG. 23). The use of densified collagen enabled the generation of constructs with an external diameter ranging from 250 to 600 μm and adequate strength to maintain a patent lumen. Notably, the cells populating the collagen scaffolds maintained expression of biliary markers such as KRT19, KRT7, HNF1B, SOX9 and CFTR and exhibited GGT and ALP enzymatic activity. Primary epithelial cells of different origin (human mammary epithelial cells; HMEC) failed to survive and adequately populate densified collagen tubes under the same conditions. Moreover, plated HMECs failed to survive in a 10% (vol/vol) bile solution, further confirming the unique capacity of ECOs for generating bile resistant bio-engineered bile ducts. Collectively, these results demonstrate the capacity of ECOs for populating tubular densified collagen scaffolds without losing their original characteristics.

Figure 24:
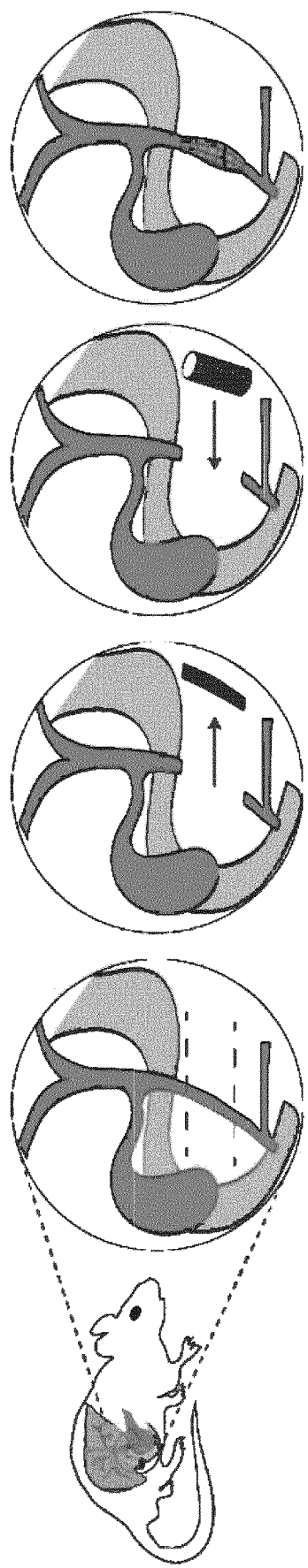
FIG. 24 shows a schematic representation of a method of bile duct replacement using ECO-populated densified collagen tubes.
Figure 25:
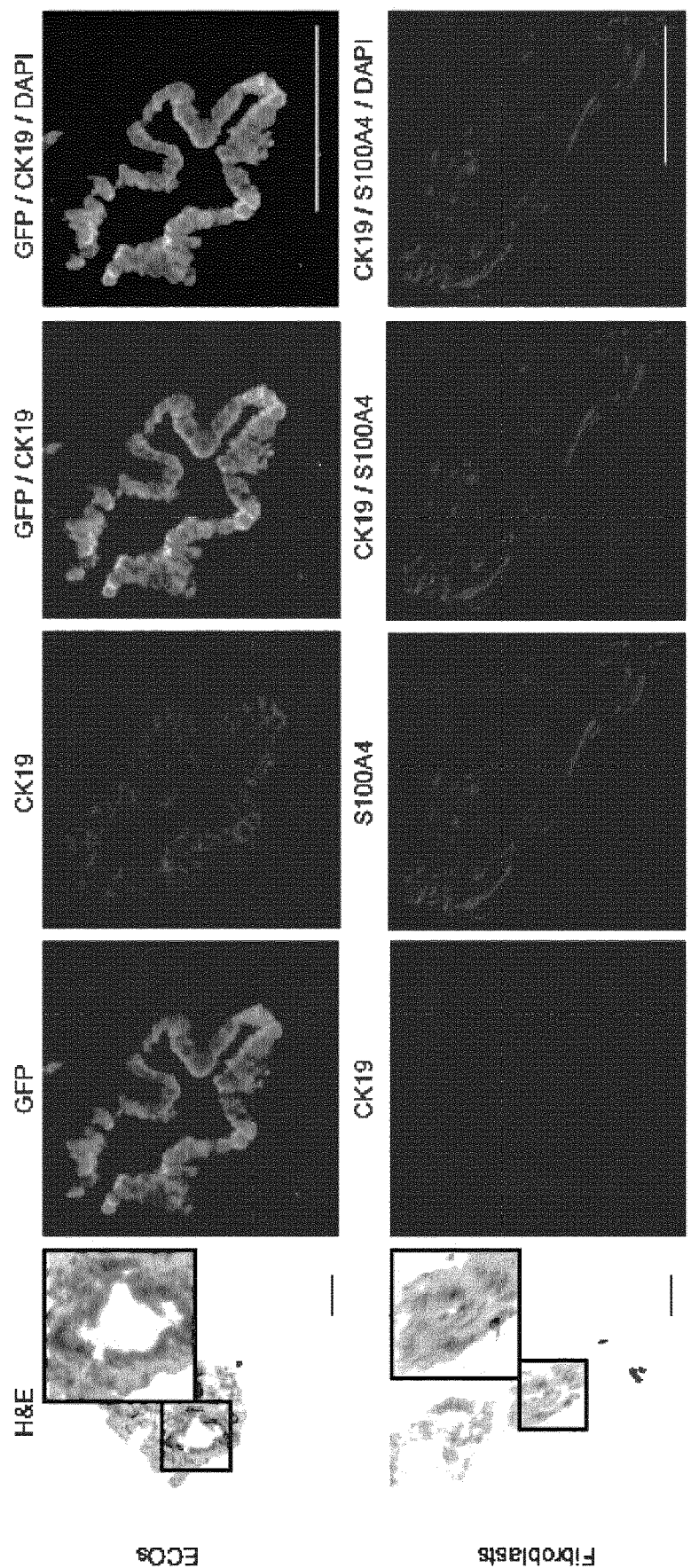
FIG. 25 shows Haematoxylin and Eosin staining and immunofluorescence analyses of ECO- and fibroblast-populated densified collagen tubes demonstrating the presence of a biliary epithelium lined by a GFP+/CK19+ epithelium and a patent lumen in ECO-tubes but not fibroblast constructs, in which the lumen is obliterated.
Figure 26:
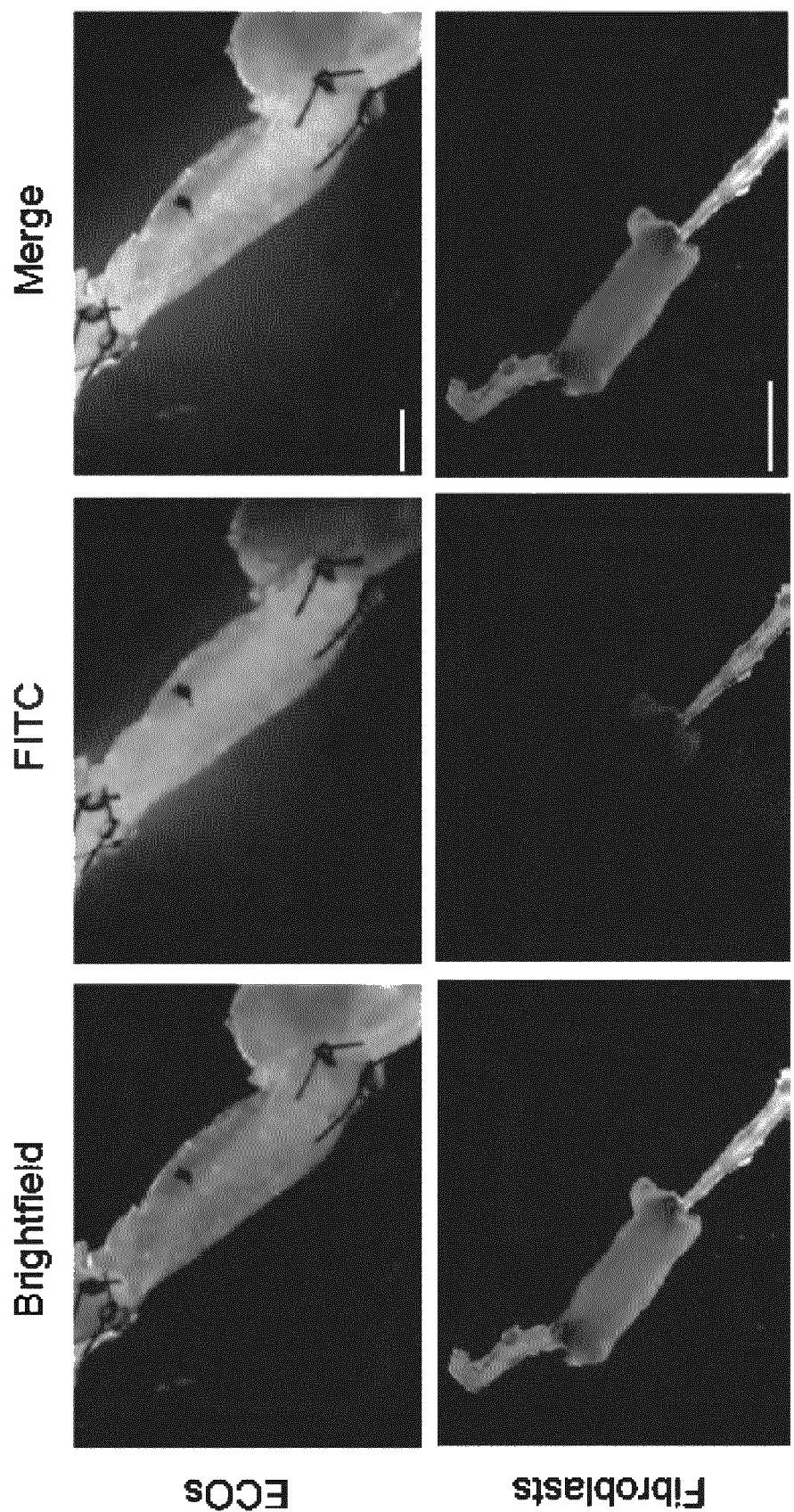
FIG. 26 shows a FITC cholangiogram of bile duct replacements using ECO- and fibroblast-populated densified collagen tubes, demonstrating lumen patency in ECO-tubes compared to lumen occlusion in fibro-constructs. Scale bars, 100 μm (ECO) and 500 μm (Fibroblasts)

We then decided to replace the native CBD of NGS mice with a bioengineered duct consisting of an ECO-populated densified collagen tube as described above. A mid-portion of the native CBD was removed and an ECO-populated collagen tube was anastomosed end-to-end to the proximal and distal duct remnants (FIG. 24). Fibroblast populated tubes were used as a negative control. Biliary reconstruction was achieved in all animals transplanted with ECO-populated tubes, which were followed up for up to a month post transplantation. Histology and IF and QPCR analyses revealed a patent lumen, with formation of a biliary epithelium by the transplanted GFP+ cells (FIG. 25); confirmed the expression of biliary markers, such as KRT19, KRT7, HNF1B, CFTR, SOX9 by the engrafted cells; but also illustrated the presence of mouse stromal and endothelial cells. Moreover, we observed minimal apoptosis and proliferation in the transplanted tubes 1 month after transplantation, confirming the stability and integrity of the reconstituted biliary epithelium. Lumen patency was further confirmed by Fluorescein Isothiocyanate (FITC) cholangiogram, MRCP and serum cholestasis marker measurements (FIG. 26). Accordingly animals receiving ECO-populated tubes exhibited no elevation in serum cholestasis markers (Bilirubin, ALP) and a patent lumen on imaging; while the bio-artificial common bile ducts retained their ALP activity in vivo. On the contrary, all fibroblast-populated collagen tubes failed due to lumen occlusion, resulting in high biliary pressures and bile leak through the site of anastomosis.

In conclusion, our results demonstrate the capacity of ECO-populated collagen tubes to replace the native CBD in vivo.

In addition, we generated ductopenia in NOD-SCID mice by administration of 4, 4'-methylenedianiline (MDA). The presence of duct damage following MDA administration was confirmed by H&E staining. Human ECOs engineered to express RFP were then injected into the mice and engraftment and the formation of neo-ducts by the RFP expressing ECOs assessed by immunofluorescence analysis. The formation of neo-ducts of different sizes in the mice and the retention of biliary marker expression (e.g. KRT19) was observed. These experiments demonstrate that expanded populations of cholangiocytes as described herein may be useful in cell based therapy against diseases affecting the liver, such as intrahepatic cholangiopathies, in addition to extra-hepatic cholangiopathies.

Disclosed herein is a method for the isolation and propagation of primary human cholangiocytes from the extrahepatic and intrahepatic biliary trees that is compatible with regenerative medicine applications. The resulting ECOs and ICOs express key biliary markers such as KRT7, KRT19, GGT, and CFTR and maintain their functional properties in vitro including ALP, GGT activity and responses to secretin and somatostatin. The suitability of ECOs and ICOs for tissue engineering and clinical applications is further illustrated by their capacity to populate biodegradable scaffolds, organize into a functional biliary epithelium and rescue a murine model of extrahepatic biliary injury.

We have demonstrated that epithelial cells from the extrahepatic and intrahepatic biliary tree can be expanded and propagated in vitro while maintaining their cholangiocyte transcriptional signature and functional characteristics. In addition, our results show that primary cholangiocytes expanded in vitro as organoids have a surprising and unique potential for organ regeneration. Indeed, our system provides the first proof-of-principle for the application of regenerative medicine in the context of common bile duct pathology. The capacity to replace a diseased common bile duct with an in vitro bio-engineered CO-tube has a considerable impact for the management of disorders such as biliary atresia, which constitutes the leading cause for pediatric liver transplantation (Murray & Carithers, *Hepatology* 2005 41:1407-1432); or ischemic strictures which are one of the most common complications following transplantation (Skaro A I et al., *Surgery* 2009 146:543-553).

Consequently CO-populated scaffolds constitute a novel system with high clinical relevance in the field of cholangiopathies.

Studies of the extrahepatic biliary epithelium have been limited by technical challenges in long-term culture and large-scale expansion of primary cholangiocytes. The capacity of ECOs and ICOs for large scale expansion addresses this challenge. Indeed, we demonstrate that starting from 105 extrahepatic cholangiocytes we can generate between 1020-1025 cells after 20 passages. Therefore, COs not only represent a novel source of cells for cell-based therapy but also provide a unique model system for studying the physiology and modelling disorders of the extrahepatic biliary tree in vitro.

Access to human tissue constitutes a considerable limitation for systems based on primary cells. However, we show that ECOs can be obtained not only from the common bile duct but also from the gallbladder. Gallbladder tissue is easily accessible and routinely discarded following liver transplantation and cholecystectomy, one of the most common surgical procedures performed. Furthermore, in individuals not having surgery the common bile duct can be accessed using minimally invasive procedures, such as endoscopic retrograde cholangio-pancreatography (ERCP) and we demonstrate that cholangiocytes can be obtained through brushings, which are routinely performed to acquire histology specimens. Notably, no morphological or functional differences were observed between organoids obtained with these different methods. Moreover, due to the scalability of our system only a small amount of starting material is required. These approaches effectively address the challenges of tissue availability and enable autologous as well as allogeneic cell based therapy.

Despite the association between organoids and adult stem cells (Koo B K & Clevers H, Gastroent. 2014 147:289-302), we never observed the expression of hepatocyte or pancreatic markers during our experiments either in vitro or after transplantation, demonstrating that the differentiation capacity of ECOs is limited to their lineage of origin. Moreover, canonical WNT signaling, which is crucial for the expansion of adult stem cell organoids (Farin H F et al.; Gastroent. 2012, 143:1518-1529. e7) is blocked in our culture conditions through the use of DKK-1. These observations show that our culture system does not include a stem cell population.

Although hIPSCs provide a source of cells capable of generating almost any tissue, initial derivation/characterization of hIPSC lines remains time consuming; while variability in capacity of differentiation still constitutes a challenge. ECOs and ICOs can be derived in less than 24 hours with a very high efficiency and can be expanded for multiple passages without losing their original characteristics. Consequently, COs and CLCs are comparable in terms of scalability and complementary in terms of applications, with the mature phenotype of COs providing a unique advantage for regenerative medicine applications in the context of tissue repair.

In summary, the present disclosure opens up novel avenues for the use of intra- and extrahepatic primary biliary tissue as a novel platform for in vitro studies, disease modelling and cell based therapy applications.

REFERENCES

Murray, K. F. & Carithers, R. L. AASLD practice guidelines: Evaluation of the patient for liver transplantation. *Hepatology* 41, 1407-1432 (2005).

Perkins, J. D. Are we reporting the same thing?: Comments. *Liver Transplant.* 13, 465-466 (2007).

Skaro, A. I. et al. The impact of ischemic cholangiopathy in liver transplantation using donors after cardiac death: The untold story. *Surgery* 146, 543-553 (2009).

Enestvedt, C. K. et al. Biliary complications adversely affect patient and graft survival after liver retransplantation. *Liver Transpl.* 19, 965-72 (2013).

Gallo, A. & Esquivel, C. O. Current options for management of biliary atresia. *Pediatr. Transplant.* 17, 95-98 (2013).

Felder, S. I. et al. Hepaticojejunostomy using short-limb Roux-en-Y reconstruction. *JAMA Surg* 148, 253-7-8 (2013).

Sampaziotis, F., Segeritz, C.-P. & Vallier, L. Potential of human induced pluripotent stem cells in studies of liver disease. *Hepatology* 62, 303-311 (2015).

Kanno, N., LeSage, G., Glaser, S., Alvaro, D. & Alpini, G. Functional heterogeneity of the intrahepatic biliary epithelium. Hepatology 31, 555-61 (2000).

Sampaziotis, F. et al. Cholangiocytes derived from human induced pluripotent stem cells for disease modeling and drug validation. *Nat. Biotechnol.* 1-11 (2015). doi: 10.1038/nbt.3275

Huch, M. et al. Long-Term Culture of Genome-Stable Bipotent Stem Cells from Adult Human Liver. *Cell* 160, 299-312 (2014).

Lin, S. M., Du, P., Huber, W. & Kibbe, W. A. Model-based variance-stabilizing transformation for Illumina microarray data. *Nucleic Acids Res.* 36, (2008).

LeSage, G., Glaser, S. & Alpini, G. Regulation of cholangiocyte proliferation. *Liver* 21, 73-80 (2001).

Bertero, A. et al. Activin/Nodal signaling and NANOG orchestrate human embryonic stem cell fate decisions by controlling the H3K4me3 chromatin mark. *Genes Dev.* 29, 702-17 (2015).

Campos, P. B., Sartore, R. C., Abdalla, S. N. & Rehen, S. K. Chromosomal spread preparation of human embryonic stem cells for karyotyping. *J. Vis. Exp.* 4-7 (2009). doi: 10.3791/1512

Koo, B.-K., Sasselli, V. & Clevers, H. Retroviral gene expression control in primary organoid cultures. *Curr. Protoc. Stem Cell Biol.* 27, Unit 5A.6. (2013).

Shultz, L. D. et al. Human lymphoid and myeloid cell development in NOD/LtSz-scid IL2R gamma null mice engrafted with mobilized human hemopoietic stem cells. *J. Immunol.* 174, 6477-6489 (2005).

Du, P., Kibbe, W. & Lin, S. M. Iumi: a pipeline for processing Illumina microarray. *Bioinformatics* 24, 1547-8 (2008).

Smyth, G. K. Linear models and empirical bayes methods for assessing differential expression in microarray experiments. *Stet Appl Genet Mol Biol* 3 (2004).

Koo, B. K. & Clevers, H. Stem cells marked by the r-spondin receptor LGR5. *Gastroenterology* 147, 289-302 (2014).

Farin, H. F., Van Es, J. H. & Clevers, H. Redundant sources of Wnt regulate intestinal stem cells and promote formation of paneth cells. *Gastroenterology* 143, 1518-1529. e7 (2012).

The invention claimed is:

1. A method for expanding human primary cholangiocytes in vitro comprising:
   (i) providing a population of isolated human primary cholangiocytes;
   (ii) forming cholangiocyte organoids from the population of isolated human primary cholangiocytes and;
   (iii) culturing the cholangiocyte organoids in an expansion medium in conditions sufficient for expanding human primary cholangiocytes, to produce an expanded population of human primary cholangiocytes,
   wherein the expansion medium is a nutrient medium supplemented with growth factors comprising epidermal growth factor (EGF), a canonical Wnt signaling inhibitor and R-spondin; and
   the canonical Wnt signaling inhibitor increases the phosphorylation of B-catenin in the cholangiocyte organoids.

2. The method according to claim 1 wherein the canonical Wnt signalling inhibitor is Dickkopf-related protein 1 (DKK-1).

3. The method according to claim 1 wherein the expansion medium comprises a scaffold matrix and the nutrient medium supplemented with EGF, the canonical Wnt inhibitor and R-spondin.

4. The method according to claim 1 wherein the human primary cholangiocytes in the expanded population express CK7, CK18, CK19, HNF1B, Gamma Glutamyl-Transferase (GGT), Jagged 1 (JAG1), NOTCH2, CFTR, SCR, SSTR2, Apical Salt and Bile Transporter (ASBT), Aquaporin 1 and Anion Exchanger 2.

5. The method according to claim 1 wherein the human primary cholangiocytes in the expanded population display ALP activity, GGT activity, MDR1 mediated secretion, physiological responses to secretin and somatostatin, export of bile acids, CFTR mediated chloride transfer, physiological responses to ATP and acetylcholine and increased proliferation in response to VEGF.

6. The method according to claim 1 wherein the human primary cholangiocytes in the expanded population do not express MHC antigens.

7. The method according to claim 1 wherein the human primary cholangiocytes are cultured in the expansion medium for 20 or more passages.

8. The method of claim 1 further comprising
   (iv) seeding the expanded population of human primary cholangiocytes into a biocompatible scaffold.

9. The method according to claim 8 comprising culturing the biocompatible scaffold in an expansion medium comprising EGE, a canonical Wnt signalling inhibitor and R-spondin in conditions sufficient for expanding human primary cholangiocytes, such that the human primary cholangiocytes populate the scaffold.

* * * * *